United States Patent
Aicher et al.

(10) Patent No.: US 7,858,646 B2
(45) Date of Patent: Dec. 28, 2010

(54) POTENTIATORS OF GLUTAMATE RECEPTORS

(75) Inventors: Thomas Daniel Aicher, Superior, CO (US); Dana Rae Benesh, Westfield, IN (US); Maria-Jesus Blanco-Pillado, Indianapolis, IN (US); Guillermo S. Cortez, Indianapolis, IN (US); Todd Michael Groendyke, Ann Arbor, MI (US); Albert Khilevich, Westfield, IN (US); James Allen Knobelsdorf, Fishers, IN (US); Fredrik Pehr Marmsäter, Longmont, CO (US); Jeffrey Michael Schkeryantz, Fishers, IN (US); Tony Pisal Tang, Longmont, CO (US)

(73) Assignee: Eli Lilly and Company, Indianapolis, IN (US)

( * ) Notice: Subject to any disclaimer, the term of this patent is extended or adjusted under 35 U.S.C. 154(b) by 777 days.

(21) Appl. No.: 11/718,446

(22) PCT Filed: Nov. 15, 2005

(86) PCT No.: PCT/US2005/041367
§ 371 (c)(1),
(2), (4) Date: Aug. 27, 2007

(87) PCT Pub. No.: WO2006/057860
PCT Pub. Date: Jun. 1, 2006

(65) Prior Publication Data
US 2008/0096930 A1    Apr. 24, 2008

Related U.S. Application Data

(60) Provisional application No. 60/630,060, filed on Nov. 22, 2004.

(51) Int. Cl.
C07D 401/04 (2006.01)
C07D 213/79 (2006.01)
A61K 31/41 (2006.01)
A61K 31/4439 (2006.01)

(52) U.S. Cl. .......... 514/340; 514/345; 514/352; 514/381; 546/268.4; 546/301; 546/310; 348/253

(58) Field of Classification Search .......... None
See application file for complete search history.

(56) References Cited

U.S. PATENT DOCUMENTS

| 4,853,398 A | 8/1989 | Carr et al. |
| 5,977,177 A | 11/1999 | Englert et al. |
| 6,194,432 B1 | 2/2001 | Sheftell et al. |

FOREIGN PATENT DOCUMENTS

| EP | 0028063 | 6/1984 |
| EP | 0174770 | 3/1988 |
| EP | 0288189 | 10/1988 |
| EP | 0516069 | 5/1991 |
| JP | 61-130271 | 6/1986 |
| WO | WO0156990 | 8/2001 |
| WO | WO2004018386 | 3/2004 |
| WO | WO2006014918 | 2/2006 |
| WO | WO2006015158 | 2/2006 |
| WO | WO2006049968 | 5/2006 |
| WO | WO2006057869 | 6/2006 |
| WO | WO2006057870 | 6/2006 |

OTHER PUBLICATIONS

Brown et al., Hydroxyacetophenone-Derived Antagonists of the Peptidoleukotrienes, *J. Med. Chem.*, 1989, 807-826, 32.
Pinkerton et al., Allosteric potentiators of the metabotropic glutamate receptor 2 (mGlu2). Part 1: Identification and synthesis of phenyl-tetrazolyl acetophenones, *Bioorganic & Medicinal Chemistry Letters*, 2004, 5329-5332, 14.
Pinkerton et al., Allosteric potentiators of the mteabotropic glutamate receptor 2 (mGlu2). Part 2: 4-Thiopyridyl acetophenones as non-tetrazole containing mGlu2 receptor potentiators, *Bioorganic & Medicinal Chemistry Letters*, 2004, 5867-5872, 14.

*Primary Examiner*—Zinna N Davis
(74) *Attorney, Agent, or Firm*—Mark A. Winter

(57) ABSTRACT

The present invention provides compounds of formula (I); pharmaceutical compositions thereof, and methods of using the same, processes or preparing the same, and intermediates thereof.

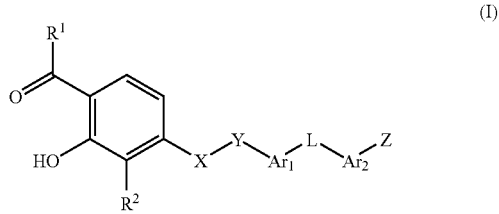

(I)

23 Claims, No Drawings

POTENTIATORS OF GLUTAMATE RECEPTORS

This application is a United States national phase entry, pursuant to 35 U.S.C. 371, of PCT/US2005/041367, filed Nov. 15, 2005, which claims the benefit of U.S. provisional application Ser. No. 60/630,060, filed Nov. 22, 2004.

The present invention provides a compound of formula I, pharmaceutical compositions thereof, and methods of using the same, as well as processes for preparing the same, and intermediates thereof.

BACKGROUND OF THE INVENTION

The excitatory amino acid L-glutamate (at times referred to herein simply as glutamate) through its many receptors mediates most of the excitatory neurotransmission within the mammalian central nervous system (CNS) and has been implicated in numerous peripheral nervous system (PNS) pathways. The excitatory amino acids, including glutamate, are of great physiological importance, playing a role in a variety of neurological, physiological and psychiatric processes, such as synaptic plasticity, motor control, respiration, cardiovascular regulation, sensory perception, and emotional responses.

Glutamate acts via at least two distinct classes of receptors. One class is composed of the ionotropic glutamate (iGlu) receptors that act as ligand-gated ion channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGlu) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The mGlu receptors belong to the Class C G-protein coupled receptor (GPCR) family. This family of GPCR's, including the calcium-sensing receptors, $GABA_B$ receptors and sensory receptors, are unique in that effectors bind to the amino-terminus portion of the receptor protein translating a signal via the transmembrane segments to the intracellular matrix through receptor/G-protein interactions. Ozawa, Kamiya and Tsuzuski, Prog. Neurobio., 54, 581 (1998). It has been demonstrated that the receptors are localized either pre- and/or post-synapticly where they can regulate neurotransmitter release, either glutamate or other neurotransmitters, or modulate the post-synaptic response of neurotransmitters, respectively.

At present, there are eight mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGlu receptors, which include the mGlu1 and mGlu5, are known to activate phospholipase C(PLC) via $G\alpha q$-proteins thereby resulting in the increased hydrolysis of phosphoinositides and intracellular calcium mobilization. There are several compounds that are reported to activate the Group I mGlu receptors including DHPG, (+/−)-3,5-dihydroxyphenylglycine. Schoepp, Goldworthy, Johnson, Salhoff and Baker, J. Neurochem., 63, 769 (1994); Ito, et al., Neurorep., 3, 1013 (1992). The Group II mGlu receptors consist of the two distinct receptors, mGlu2 and mGlu3 receptors. Both receptors are negatively coupled to adenylate cyclase via activation of $G\alpha i$-protein. These receptors can be activated by a group-selective compound such as (1S,2S,5R,6S)-2-aminobicyclo[3.1.0]hexane-2,6-dicarboxylate. Monn, et al., J. Med. Chem., 40, 528 (1997); Schoepp, et al., Neuropharmacol., 36, 1 (1997). Similarly, the Group III mGlu receptors, including mGlu4, mGlu6, mGlu7 and mGlu8, are negatively coupled to adenylate cyclase via $G\alpha i$ and are potently activated by L-AP4 (L-(+)-2-amino-4-phosphonobutyric acid). Schoepp, Neurochem. Int., 24, 439 (1994).

It should be noted that many of the available pharmacological tools are not ideal in that they cross react not only on the receptors within a group of mGlu receptors but also often have some activity between groups of mGlu receptors. For instance, compounds such as 1S,3R-ACPD, (1S,3R)-1-aminocyclopentane-trans-1,3-dicarboxylic acid, are believed to activate all of the Group I, II and III mGlu receptors depending upon the dose utilized while others, such as 1S,3S-ACPD, (1S,3S)-1-aminocyclopentane-trans-1,3-dicarboxylic acid, are more selective for the Group II receptors (mGlu2/3) than the Group I (mGlu1/5) or Group III (mGlu4/6/718). Schoepp, Neurochem. Int., 24, 439 (1994). To date, there are very few examples of selective agents for the mGlu receptors. Schoepp, Jane, and Monn, Neuropharmacol., 38, 1431 (1999).

It has become increasingly clear that there is a link between modulation of excitatory amino acid receptors, including the glutamatergic system, through changes in glutamate release or alteration in postsynaptic receptor activation, and a variety of neurological, psychiatric and neuroinflammatory disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

Leukotrienes are potent local mediators, playing a major role in inflammatory and allergic responses including arthritis, asthma, psoriasis, and thrombotic disease. Leukotrienes are straight chain eicosanoids produced by the oxidation of arachidonic acid by lipoxygenases in several cell types including: eosinophils, neutrophils, mast cells, leukocytes, and macrophages. At the present time, there are two established Class A GPCR receptors for the cysteinyl-leukotrienes (CysLT1 and CysLT2) which the leukotrienes LTC4, LTD4 and LTE4 activate, mediating their proinflammatory effects. Each of the CysLT receptors has distinct tissue distributions and associations with physiological responses. Also, the leukotriene LTD4 has a higher affinity for the CysLT1 receptor than the other leukotrienes. Back, M. Life Sciences 71, 611-622, (2002). The leukotrienes, especially LTD4 and its receptor CysLT1, have been implicated in the pathogenesis of airway and allergic diseases such as asthma by contributing to bronchoconstriction, mucus secretion, and eosinophil migration. Thus, leukotrienes have been shown to play an important role in the pathology of asthma. Rigorous proof for the role of leukotrienes in asthma has been provided by several pivotal clinical trials in which orally administered LTD4 receptor antagonists produce clear therapeutic benefit in asthma patients. These benefits include reduction in the use of classic asthma therapies such as corticosteroids. Kemp, J. P., Amer. J. Resp. Medi. 2, 139-156, (2003).

Numerous investigations confirm the importance of the leukotrienes in allergic disorders as well. Thus, after allergen provocation, a marked increase in the LT concentration in the nasal lavage fluid of patients with allergic rhinitis was detected both in the early phase and in the late phase. Creticos, P. S., S. P. Peters, N. F. Adkinson, R. M. Naclerio, E. C. Hayes, P. S, Norman, L. M. Lichtenstein, N. Eng. J. Med. 310:1626 (1984). In addition, treatment with clinically efficacious antihistamines, such as azelastine, has shown a reduction in the formation of the cysteinyl-leukotrines, establishing a correlative relationship of allergic reaction symptoms to the degree of leukotriene formation and, thus, CysLT receptor activation. Achterrath-Tuckermann, U., Th. Simmet, W. Luck, I. Szelenyi, B. A. Peskar, Agents and Actions 24:217, 1988; Shin, M. H., F. M. Baroody, D. Proud, A. Kagey-Sobotka, L. M. Lichtenstein, M. Naclerio, Clin. Exp. Allergy 22:289, 1992.

U.S. Pat. No. 6,194,432 B1 discloses a method for using leukotriene antagonist drugs to prevent and treat recurrent primary headaches including migraine headaches.

U.S. Pat. No. 5,977,177 discloses certain substituted phenyl derivative compounds are modulators of endothelin and, as such, are useful in treating many different conditions including asthma.

U.S. Pat. No. 4,853,398 discloses certain benzene derivative compounds are selective antagonists of leukotrienes and, as such, are useful in treating allergic disorders such as asthma.

European Patent Application No. EP 28063 A1 and UK Patent Application No. GB 2058785 disclose certain phenol derivative compounds are antagonists of slow reacting substance of anaphylaxis and, as such, are useful in treating asthma, hay fever and skin afflictions.

Brown, F. J. et al J. Med. Chem. 32, p. 807-826 (1989) discloses certain hydroxyacetophenone derivative compounds are antagonists of leukotrienes and, as such, play a role in treating asthma.

International Patent Application Publication No. WO 2001056990 A2 and U.S. Pat. No. 6,800,651 B2 disclose certain pyridine derivative compounds are potentiators of metabotropic glutamate receptor function, specifically; potentiators of mGlu2 receptor function and, as such, are useful in the treatment of many different conditions including anxiety and migraine headache.

International Patent Application Publication No. WO 2004018386 and Pinkerton, A. B. et al Bioorg. Med. Chem. Lett., 14, p. 5329-5332 (2004) disclose certain acetophenone derivative compounds are potentiators of glutamate receptor function, specifically; potentiators of mGlu2 receptor function and, as such, are useful in the treatment of many different conditions including anxiety, schizophrenia and migraine headache.

Recently, Pinkerton, A. B. et al Bioorg. Med. Chem. Lett., 14, p. 5867-5872 (2004) disclose certain 4-thiopyridyl acetophenone derivative compounds are potentiators of glutamate receptor function, specifically; potentiators of mGlu2 receptor function and, as such, may be useful in the treatment of CNS disorders including anxiety, schizophrenia and epilepsy.

The present invention provides compounds of formula I that are potentiators of the mGlu2 receptor and antagonists of the CysLT1 receptor. As such, compounds of formula I would provide a means to treat disorders associated with glutamate or leukotrienes. In addition, it is anticipated that in disorders with a glutamate and leukotriene component to the onset, propagation and/or symptoms, the compounds of formula I will provide an effective treatment for the patient. The medical consequences of such glutamate dysfunction make the abatement of these neurological processes an important therapeutic goal.

SUMMARY OF THE INVENTION

The present invention provides a compound of formula I:

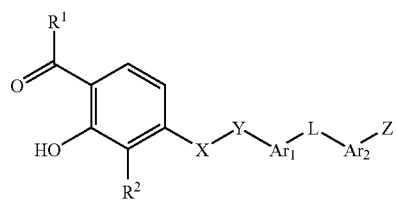

wherein $R^1$ is selected from the group consisting of C1-C5 alkyl, C3-C7 cycloalkyl, C4-C8 cycloalkylalkyl, phenyl and substituted phenyl;

$R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazloyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl, and substituted pyridazinyl;

X is selected from the group consisting of O, $S(O)_m$, and $NR^3$;

Y is selected from the group consisting of C1-C3 alkanediyl and substituted C1-C3 alkanediyl;

$Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;

L is selected from the group consisting of -G-O-J-, -G-S$(O)_p$-J-, and -G-N($R^4$)-J-;

G and J are independently selected from the group consisting of a bond and C1-C3 alkanediyl;

$R^3$ is independently hydrogen or C1-C5 alkyl;

$R^4$ is independently selected from the group consisting of hydrogen, C1-C5 alkyl, C(=O)$R^3$, C(=O)N$R^3R^3$ and SO$_2R^3$;

Z is selected from the group consisting of $(CH_2)_n$COOH,

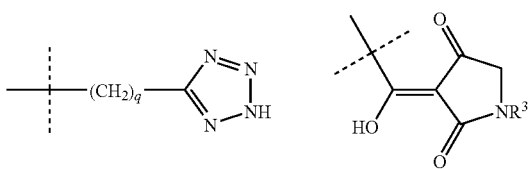

-continued

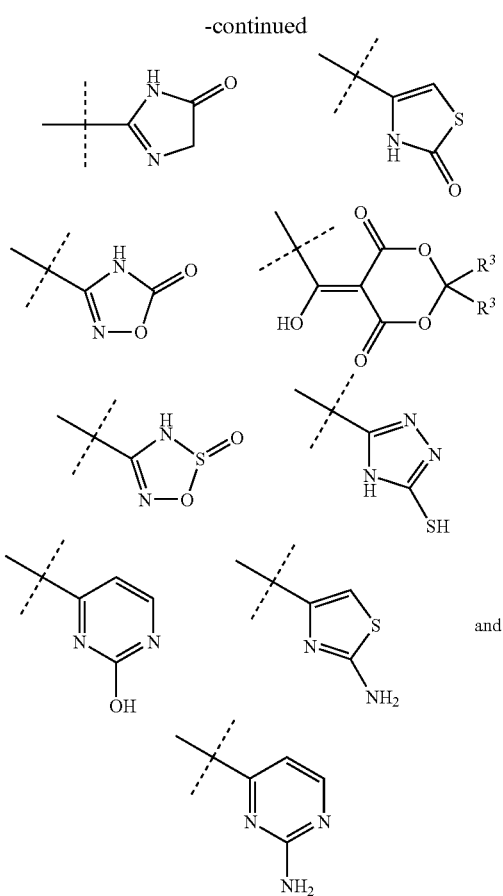

m and p are independently 0, 1, or 2;
n and q are independently 0, 1, 2 or 3; and pharmaceutically acceptable salts thereof.

The present invention also provides for novel pharmaceutical compositions, comprising a compound of the formula I and a pharmaceutically acceptable diluent.

Because the compounds of formula I are potentiators of the mGlu2 receptor, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

In another embodiment the present invention provides methods of treating neurological and psychiatric disorders associated with glutamate dysfunction, comprising administering to a patient in need thereof an effective amount of a compound of formula I. That is, the present invention provides for the use of a compound of formula I or pharmaceutical composition thereof for the treatment neurological and psychiatric disorders associated with glutamate dysfunction.

Of the disorders above, the treatment of migraine, anxiety, schizophrenia, and epilepsy are of particular importance.

In a preferred embodiment the present invention provides a method of treating migraine, comprising administering to a patient in need thereof an effective amount of a compound of formula I.

In another preferred embodiment the present invention provides a method of treating anxiety, comprising administering to a patient in need thereof an effective amount of a compound of formula I. Particularly preferred anxiety disorders are generalized anxiety disorder, panic disorder, and obsessive compulsive disorder.

In another preferred embodiment the present invention provides a method of treating schizophrenia, comprising administering to a patient in need thereof an effective amount of a compound of formula I.

In yet another preferred embodiment the present invention provides the use of a compound of formula I for the manufacture of a medicament for the treatment of neurological and psychiatric disorders associated with glutamate dysfunction.

In yet another preferred embodiment the present invention provides a compound of formula I for use as a medicament.

In yet another preferred embodiment the present invention provides the use of a compound of formula I for the manufacture of a medicament for the treatment of migraine.

In yet another preferred embodiment the present invention provides a pharmaceutical composition for the treatment of neurological and psychiatric disorders associated with glutamate dysfunction containing as an active ingredient a compound of formula I.

In yet another preferred embodiment the present invention provides a method of treating epilepsy, comprising administering to a patient in need thereof an effective amount of a compound of formula I.

Because such potentiators, including the compounds of formula I, positively modulate metabotropic glutamate receptor response to glutamate, it is an advantage that the present methods utilize endogenous glutamate.

Because such potentiators positively modulate metabotropic glutamate receptor response to glutamate agonists it is understood that the present invention extends to the treatment of neurological and psychiatric disorders associated with glutamate dysfunction by administering an effective amount of a metabotropic glutamate potentiator, including the compounds of formula I, in combination with a potentiated amount of a metabotropic glutamate receptor agonist. Such a combination may be advantageous in that it may augment the activity and selectivity of an agonist of metabotropic glutamate receptors, in particular a potentiator of mGlu2 receptors.

Because many the compounds of formula I are antagonists of the CysLT1 receptor, many of the compounds of formula I are useful for the treatment of a variety of disorders mediated by one or more leukotrienes such as inflammatory and allergic disorders associated with leukotriene mediation including inflammatory bowel syndrome, inflammatory bowel disease, arthritis, asthma, psoriasis, and thrombotic disease.

In another embodiment the present invention provides methods of treating a variety of disorders mediated by one or more leukotrienes, comprising administering to a patient in need thereof an effective amount of a compound of formula I. That is, the present invention provides for the use of a compound of formula I or pharmaceutical composition thereof for the treatment inflammatory and allergic disorders associated with leukotriene mediation.

In a preferred embodiment the present invention provides a method of treating asthma, comprising administering to a patient in need thereof an effective amount of a compound of formula I.

In another embodiment the present invention provides a process for preparing a compound of formula I or a pharmaceutically acceptable salt thereof.

DETAILED DESCRIPTION OF THE INVENTION

This invention provides methods of potentiating metabotropic glutamate receptors, in particular mGlu2 receptors. In the present methods an effective amount of a potentiator of metabotropic glutamate 2 receptors, including a compound of formula I, is administered which positively modulates the effect of glutamate or glutamate agonists on the subject receptor.

Before describing the present invention in greater detail, it is understood that the invention in its broadest sense is not limited to particular embodiments described herein, as variations of the particular embodiments described herein are within the scope of the claimed invention.

Thus, compounds useful in the present invention are those which are potentiators of metabotropic glutamate receptors, particularly, those that potentiate the effects of glutamate and glutamate agonists at mGlu2 metabotropic glutamate receptors, and even more particularly, those that potentiate the effects of glutamate and glutamate agonists at mGlu2 receptors. Useful compounds are varied in structure, and so long as they embrace the above properties, they are suitable for use in the present invention. Preferred compounds include, but are not limited to, those described herein.

The compounds of formula I potentiate the function of glutamate receptors. Specifically, the compounds of formula I are potentiators of the mGlu2 receptor.

Compounds of in the present invention also include those which are modulators of leukotriene receptors, particularly, those that antagonize the CysLT1 receptor.

As used herein, the following terms have the meanings indicated:

The term "C1-C5 alkyl" refers to a straight or branched alkyl chain having from one to five carbon atoms, and includes methyl, ethyl, propyl, iso-propyl, butyl, iso-butyl, sec-butyl, t-butyl, pentyl and the like. Particular values of "C1-C5 alkyl" are methyl, ethyl, n-propyl and iso-propyl.

The term "alkyl" refers to a monovalent aliphatic hydrocarbon. Within the meaning of "alkyl" is the term "C1-C3 alkyl".

The term "C1-C3 alkyl" refers to a straight or branched alkyl chain having from one to three carbon atoms, and includes methyl, ethyl, propyl, iso-propyl, and the like.

The term "substituted C1-C5 alkyl" refers to a straight or branched alkyl chain having from one to five carbon atoms, and includes methyl, ethyl, propyl, iso-propyl, butyl, iso-butyl, sec-butyl, t-butyl and pentyl having from 1 to 3 substituents selected from the group consisting of hydroxy, halogen, azido, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, substituted benzyloxy, pyridyl, substituted pyridyl, thienyl, and substituted thienyl.

The term "C1-C5 alkanediyl" refers to a straight or branched divalent alkyl chain having from one to five carbon atoms, and includes methylene and ethane-1,1-diyl.

The term "substituted C1-C5 alkanediyl" refers to a straight or branched divalent alkyl chain having from one to five carbon atoms, and includes methylene having a substituent selected from the group consisting of hydroxyl, fluoro, azido, methoxy, amino, acetylamino and methylsulfonamide. Particular values of "substituted C1-C5 alkanediyl" are CH(OH), CH(F), CHN$_3$, CH(OCH$_3$), CHNH$_2$, CHNH(C=O)CH$_3$, CHNH(SO$_2$)CH$_3$.

The term "C1-C3 alkanediyl" refers to a straight or branched divalent alkyl chain having from one to three carbon atoms, and includes methylene.

The term "substituted C1-C3 alkanediyl" refers to a straight or branched alkyl chain having from one to three carbon atoms, and includes methylene, having from 1 or 2 substituents selected from the group consisting of hydroxy, halogen, azido, alkoxy, acyloxy, carboxy, alkoxycarbonyl, amido, substituted amido, amino, acylamino, sulfonylamido, sulfonamide, phenyl, substituted phenyl, pyridyl, substituted pyridyl, thienyl, and substituted thienyl The term "halogen or halo" refers to chloro, fluoro, bromo or iodo.

The term "C1-C3 fluoro alkyl" refers to an alkyl chain having from one to three carbon atoms substituted with one or more fluorine atoms, and includes fluoromethyl, difluoromethyl, trifluoromethyl, 2,2,2-trifluoroethyl, 3,3,3-trifluoropropyl and the like. A particular value of "C1-C3 fluoro alkyl" is trifluoromethyl.

The term "alkoxy" refers to a straight or branched alkyl chain attached to an oxygen atom. Within the meaning of "alkoxy" is the term "C1-C4 alkoxy".

The term "C1-C4 alkoxy" refers to straight or branched alkyl chain having from one to four carbon atoms attached to an oxygen atom, and includes methoxy, ethoxy, propoxy, iso-propoxy, butoxy, iso-butoxy, sec-butoxy, t-butoxy, and the like.

The term "substituted alkoxy" refers to a straight or branched alkyl chain attached to an oxygen atom having from 1 to 3 substituents. Within the meaning of "substitiuted alkoxy" is the term "substituted C1-C4 alkoxy".

The term "substituted C1-C4 alkoxy" refers to straight or branched alkyl chain having from one to four carbon atoms attached to an oxygen atom, and includes methoxy, ethoxy, propoxy, iso-propoxy, butoxy, iso-butoxy, sec-butoxy, t-butoxy, and the like, having from 1 to 3 substituents selected from the group consisting of hydroxy, halogen, alkoxy, carboxy, amido, substituted amido, amino, acylamino, sulfonylamido, sulfonamide, phenyl, and substituted phenyl; and when one or more of the substituents is hydroxy, halogen, alkoxy, amino, acylamino, and sulfonamide, then those substituents are not attached to the same carbon as the alkoxy oxygen atom.

The term "C3-C7 cycloalkyl" refers to saturated cyclic alkyl group having from three to seven carbon atoms and includes cyclopropyl, cyclobutyl, cyclopentyl, cyclohexyl, and cycloheptyl.

The term "C4-C8 cycloalkylalkyl" refers to saturated cyclic alkyl group having from three to seven carbon atoms linked to the point of substitution by a divalent unsubstituted saturated straight-chain or branched-chain hydrocarbon radical having at least 1 carbon atom and includes, cyclopropylmethyl, cyclopropyl-2-propyl, cyclobutylethyl, cyclopentylmethyl, cyclohexylmethyl, cycloheptylmethyl and the like.

The terms "phenyl and substituted phenyl" or "phenylene and substituted phenylene" refer to a monovalent or divalent radical, repectively, of the formula

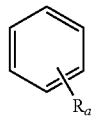

wherein $R_a$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. Particular values of $R_a$ are hydrogen, methoxy and fluoro. Particular values of $R_a$ are hydrogen, methoxy, fluoro and trifluoromethyl.

The terms "thiophenyl and substituted thiophenyl" or "thiophenediyl and substituted thiophenediyl" refer to a monovalent or divalent radical, repectively, of the formula

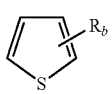

wherein $R_b$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_b$ is hydrogen.

The terms "pyridinyl and substituted pyridinyl" or "pyridinediyl and substituted pyridinediyl" refer to a monovalent or divalent radical, repectively, of the formula

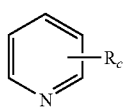

wherein $R_c$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_c$ is hydrogen.

The terms "thiazolyl and substituted thiazolyl" or "thiazolediyl and substituted thiazolediyl" refer to a monovalent or divalent radical, repectively, of the formula

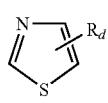

wherein $R_d$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_d$ is hydrogen.

The terms "furanyl and substituted furanyl" or "furanediyl and substituted furanediyl" refer to a monovalent or divalent radical, repectively, of the formula

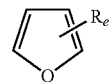

wherein $R_e$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_e$ is hydrogen.

The terms "isothiazolyl and substituted isothiazoyl" or "isothiazolediyl and substituted isothiazolediyl" refer to a monovalent or divalent radical, repectively, of the formula

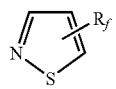

wherein $R_f$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_f$ is hydrogen.

The terms "isoxazolyl and substituted isoxazolyl" or "isoxazolediyl and substituted isoxazolediyl" refer to a monovalent or divalent radical, repectively, of the formula

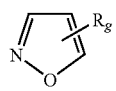

wherein $R_g$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_g$ is hydrogen.

The terms "1,2,4-oxadiazolyl and substituted 1,2,4-oxadiazolyl" or "1,2,4-oxadiazole-3,5-diyl" refer to a monovalent radical or divalent radical lacking $R_h$, repectively, of the formula

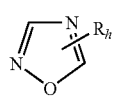

wherein $R_h$ is independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_h$ is hydrogen.

The terms "pyrimidinyl and substituted pyrimidinyl" or "pyrimidinediyl and substituted pyrimidinediyl" refer to a monovalent or divalent radical, repectively, of the formula

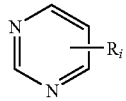

wherein $R_i$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_i$ is hydrogen.

The terms "pyridazinyl and substituted pyridazinyl" or "pyridazinediyl and substituted pyridazinediyl" refer to a monovalent or divalent radical, repectively, of the formula

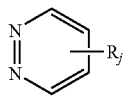

wherein $R_j$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_j$ is hydrogen.

The terms "oxazolyl and substituted oxazolyl" or "oxazolediyl and substituted oxazolediyl" refer to a monovalent or divalent radical, repectively, of the formula

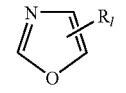

wherein $R_l$ is 1 or 2 groups independently selected from the group consisting of hydrogen, alkyl, substituted alkyl, cycloalkyl, alkoxy, substituted alkoxy, halogen, carboxy, alkoxycarbonyl, aimido, substituted amido, amino, acylamino, sulfonylamido, sulfonamide, cyano, nitro, phenyl, and substituted phenyl. A particular value of $R_l$ is hydrogen.

The term "carboxy" refers to a radical of the formula

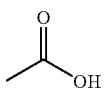

The term "alkoxycarbonyl" refers to a radical of the formula

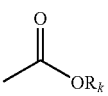

wherein $R_k$ is selected from the group consisting of alkyl, substituted alkyl, phenyl and substituted phenyl. Particular values of $R_k$ are methyl and ethyl.

The term "amido" refers to a radical of the formula

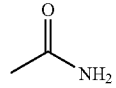

The term "substituted amido" refers to a radical of the formula

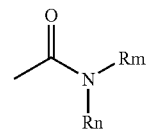

wherein $R_m$ is selected from the group consisting of alkyl and $R_n$ is selected from the group consisting of hydrogen, alkyl, phenyl and substituted phenyl. A particular value for $R_m$ is methyl. Particular values for $R_n$ are hydrogen and methyl.

The term "acylamino" refers to a radical of the formula

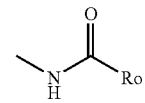

wherein $R_o$ is selected from the group consisting of alkyl, phenyl, and substituted phenyl. A particular value of $R_o$ is methyl.

The term "sulfonylamido" refers to a radical of the formula

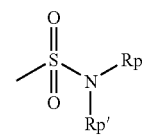

wherein $R_p$ is selected from the group consisting of alkyl, phenyl, and substituted phenyl; and $R_{p'}$ is selected from the group consisting of hydrogen and alkyl. A particular value for $R_p$ is methyl. Particular values for $R_{p'}$ are hydrogen and methyl.

The term "sulfonamide" refers to a radical of the formula

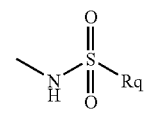

wherein $R_q$ is selected from the group consisting of alkyl, phenyl, and substituted phenyl. A particular value of $R_q$ is methyl.

As is readily apparent to those skilled in the art, the compounds of formula I may exist as tautomers. Where tautomers exist, each tautomeric form and mixtures thereof, are contemplated as included in the present invention. When any reference in this application to one of the specific tautomers of the compounds of formula I is given, it is understood to encompass every tautomeric form and mixtures thereof. For example, where the group Z is tetrazolyl, a compound of formula I exists as tautomer I and tautomer II. As such, it is understood any reference to a compound of formula I where the group Z is tetrazolyl as tautomer I encompasses tautomer II as well as mixtures of tautomer I and tautomer II.

pyridazinediyl and 1,2,4-oxadiazole-3,5-diyl. It is understood that $Ar_1$ and $Ar_2$ being at least bi-radical may be attached in a 1-2, 1-3 or 1-4 regioisomeric position depending on the nature of the ring and the number and location of substituents. It is further understood that the present invention encompasses all possible regioisomeric combinations of attachment to $Ar_1$ and $Ar_2$. For example, where $Ar_1$ is phenylene there exists three possible regioisomers, designated as 1-2 (ortho or o-), 1-3 (meta or m-) and 1-4 (para or p-), all of which are encompassed in the present invention for a compound of formula I where $Ar_1$ is phenylene.

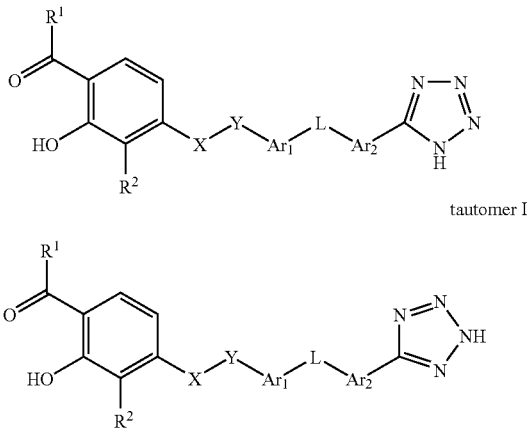

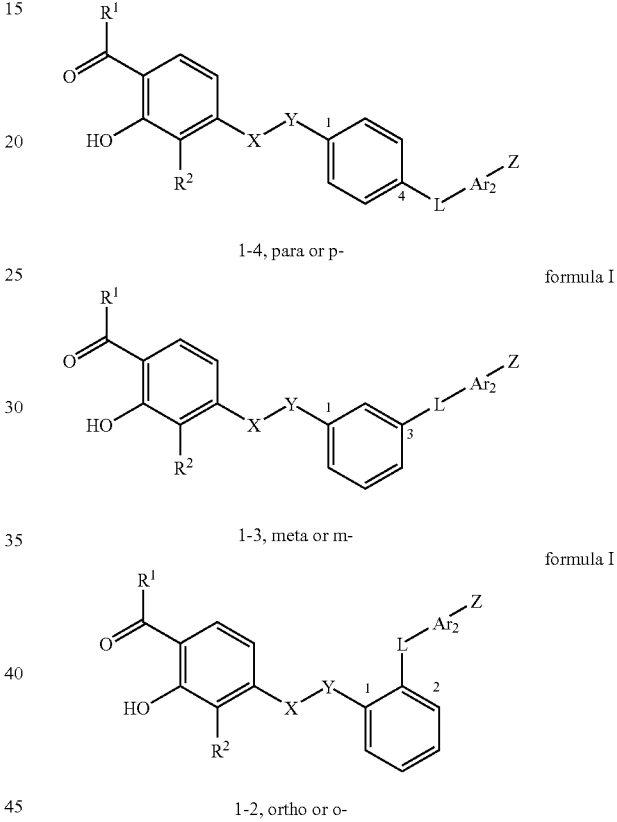

It is understood that compounds of the present invention may exist as stereoisomers. All enantiomers, diastereomers, and mixtures thereof, are contemplated within the present invention. Where specific stereochemistries are identified in this application, the Cahn-Ingold-Prelog designations of (R)- and (S)- and the cis- and trans-designation of relative stereochemistry are used to refer to specific isomers and relative stereochemistry. Known optical rotations are designated by (+) and (−) for dextrorotatary and levorotatary, respectively. Where a chiral compound is resolved into its enantiomers, but absolute configurations are not determined, the isomers are designated as isomer 1, isomer 2, etc.

Specific stereoisomers can be prepared by stereospecific synthesis using enantiomerically pure or enriched starting materials. The specific stereoisomers of either starting materials or compounds of formula I can be resolved by techniques well known in the art, such as those found in *Stereochemistry of Organic Compounds*, E. I. Eliel and S. H. Wilen (Wiley 1994) and *Enantiomers, Racemates, and Resolutions*, J. Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts.

While all enantiomers, diastereomers, and mixtures thereof, are contemplated within the present invention, preferred embodiments are single enantiomers and single diastereomers.

The terms "$Ar_1$ and $Ar_2$" refer to five or six member aryl or heterocyclic rings independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted The term "pharmaceutically acceptable salt" refers to an addition salt that exists in conjunction with the acidic and/or basic portion of a compound of formula I. Such salts include the pharmaceutically acceptable salts listed in *Handbook of Pharmaceutical Salts: Properties, Selection and Use*, P. H. Stahl and C. G. Wermuth (Eds.), Wiley-VCH, New York, 2002 which are known to the skilled artisan. Pharmaceutically acceptable salts that are acid addition are formed when a compound of formula I and the intermediates described herein containing a basic functionality are reacted with a pharmaceutically acceptable acid. Pharmaceutically acceptable acids commonly employed to form such acid addition salts include inorganic acids, such as hydrochloric, hydrobromic, nitric, sulphuric or phoshoric acids, and organic acids such as acetic, citric, esylic, fumaric, glycolic, glucuronic, glutaric, lactic, maleic, malic, mandelic, mesylic, napadisylic, oxalic, succinic, tartaric, salicyclic, o-acetoxybenzoic, or p-toluene-sulphonic. Pharmaceutically acceptable salts that are base addition are formed when a compound of formula I and the intermediates described herein containing a acidic functionality are reacted with a pharmaceutically acceptable base. Pharmaceutically acceptable bases commonly employed to form base addition salts include organic bases such as ammonia, arginine, benethamine, benzathine, benzylamine, betaine, butylamine, choline, dicyclohexylamine, diethanolamine, diethylamine, ethylenediamine, glucosamine, imidazole, lysine, piperazine, procaine, and inorganic bases such as calcium, potassium, sodium and zinc salts of hydroxide, carbonate or bicarbonate and the like.

In addition to pharmaceutically acceptable salts, other salts are included in the invention. They may serve as intermediates in the purification of compounds or in the preparation of other, for example pharmaceutically-acceptable, acid addition salts, or are useful for identification, characterization or purification.

The term "protecting group or Pg," as used herein, refers to those groups intended to protect or block functional groups against undesirable reactions during synthetic procedures. In the case of an amino or hydroxyl functional group, the suitable protecting group used will depend upon the conditions that will be employed in subsequent reaction steps wherein protection is required. For example, it may be desirable to employ the protection of multiple functional groups, such as amino and hydroxyl, and control their protection and deprotection independently. Commonly used amino and hydroxyl protecting groups are disclosed in *Protective Groups In Organic Synthesis*, T. W. Greene and P. G. M. Wuts 3rd Ed. (John Wiley & Sons, New York (1999)). Suitable amino protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p)-biphenylyl)-1-methylethoxycarbonyl, alpha, alpha-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable amino protecting groups are acetyl, methyloxycarbonyl, benzoyl, pivaloyl, allyloxycarbonyl, t-butylacetyl, benzyl, t-butyloxycarbonyl (Boc) and benzyloxycarbonyl (Cbz). Suitable hydroxyl protecting groups include ethers such as methoxymethyl, 1-ethoxyethyl, tert-butyl, allyl, benzyl, tetrahydropyranyl and the like; silyl ethers such as trimethylsilyl, triethylsilyl, triisopropylsilyl, tert-butyldimethylsilyl and the like; esters such as formate, acetate, pivaloate, benzoate and the like; and sulfonates such as mesylate, benzylsulfonate, tosylate and the like. Preferred suitable hydroxyl protecting groups are acetyl, trimethylsilyl, triisopropylsilyl, tert-butyldimethylsilyl and benzyl.

As with any group of pharmaceutically active compounds, some groups are preferred in their end use application. Preferred embodiments for a compound of formula I of the present invention are given below.

Compounds in which $R^1$ is C3-C7 cycloalkyl or C4-C8 cycloalkylalkyl are preferred. Compounds in which $R^1$ is C1-C5 alkyl are more preferred. Compounds in which $R^1$ is methyl are even more preferred.

Compounds in which $R^2$ is phenyl, substituted phenyl, thiophenyl, substituted thiophenyl, thiazolyl, substituted thiazolyl, pyridinyl, or substituted pyridinyl are preferred. Compounds in which $R^2$ is C1-C5 alkyl, halo or C1-C3 fluoroalkyl are more preferred. Compounds in which $R^2$ is methyl, propyl, trifluoromethyl, or chloro are even more preferred.

Compounds in which X is $S(O)_m$ where m is 0, 1 or 2 are preferred. Compounds in which X is O are more preferred.

Compounds in which Y is C1-C3 alkanediyl are preferred. Compounds in which Y is methylene are more preferred.

Compounds in which $Ar_1$ is substituted phenylene, 1,2,4-oxadiazol-3,5-diyl or substituted pyridinediyl are preferred. Compounds in which $Ar_1$ is phenylene or pyridinediyl, either attached in the 1-3 position, are more preferred. Compounds in which $Ar_1$ is phenylene or pyridinediyl, either ring attached in the 1-4 position, are even more preferred.

Compounds in which $Ar_2$ is substituted phenylene or substituted pyridinediyl are preferred. Compounds in which $Ar_2$ is phenylene or pyridinediyl are more preferred.

Compounds in which $Ar_2$ is pyridinediyl attached in the 1-4 or 1-3 position are even more preferred.

Compounds in which $Ar_1$ and $Ar_2$ are independently phenylene or pyridinediyl are preferred.

Compounds in which $Ar_1$ is phenylene are preferred.

Compounds in which $Ar_2$ is pyridinediyl are preferred.

Compounds in which $Ar_2$ is attached at the 1-4 position are preferred.

Compounds in which $Ar_2$ is attached at the 1-3 position are preferred.

Compounds in which $Ar_1$ is attached at the 1-3 position or 1-4 position are preferred.

Compounds in which L is $S(O)_p$ are preferred. Compounds in which L is S are more preferred. Compounds in which L is O are more preferred.

Compounds in which Z is

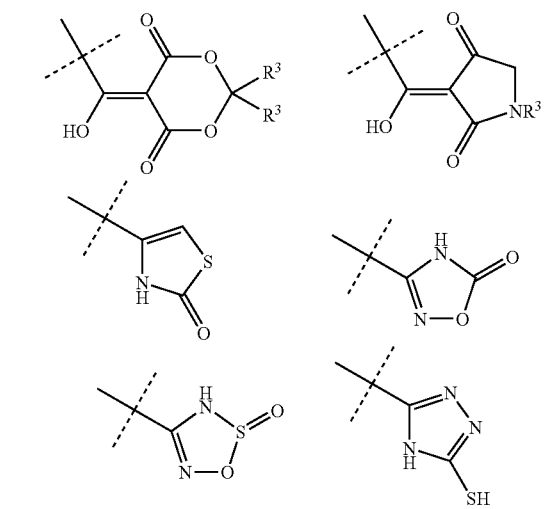

-continued

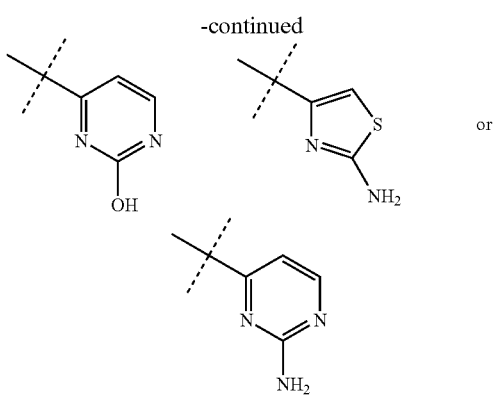

are preferred. Compounds in which Z is

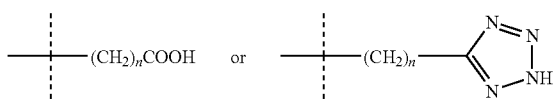

are more preferred. Compounds in which Z is

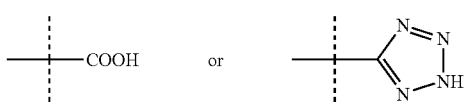

are even more preferred.

A compound of formula I as described above wherein $R^1$ is methyl or ethyl;

$R^2$ is selected from the group consisting of hydrogen, methyl, ethyl, propyl, fluoro, chloro, trifluoromethyl, and COOH;

X is O;

Y is methylene;

$Ar_1$ is phenylene or pyridinediyl;

$Ar_2$ is selected from the group consisting of phenylene, trifluoromethylphenylene, and pyridinediyl;

L is selected from the group consisting of O, S, SO, $SO_2$ and NH; and

Z is COOH or

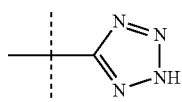

is preferred.

A compound of formula I selected from the group consisting of 1-(2-hydroxy-3-methyl-4-{4-[4-(1H-tetrazol-5-yl)-pyridin-2-yloxy]-benzyloxy}-phenyl)-ethanone, 1-(2-hydroxy-3-methyl-4-{4-[3-(1H-tetrazol-5-yl)-phenoxy]-benzyloxy}-phenyl)-ethanone and 1-(2-hydroxy-4-{3-[4-(2H-tetrazol-5-yl)-pyridin-2-yloxy]-benzyloxy}-3-trifluoromethyl-phenyl)-ethanone is preferred.

A compound of formula I which is 6-(3-((4-acetyl-3-hydroxy-2-propyl-phenoxy)methyl)phenylthio)isonicotinic acid is more preferred.

Further embodiments of the invention include a process for preparing the compound of formula I, or a pharmaceutically acceptable salt thereof, comprising (A) for a compound of formula I where Z is tetrazolyl,

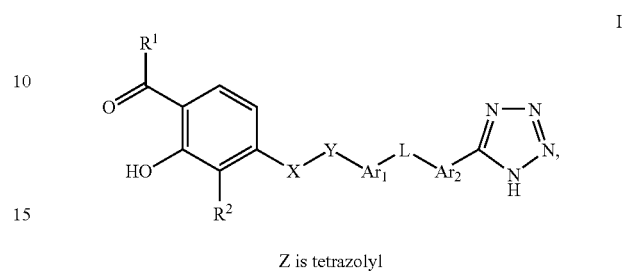

Z is tetrazolyl cycloaddition of a compound of formula II where $R^{10}$ is cyano with an azide reagent;

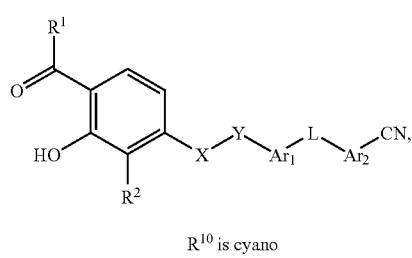

$R^{10}$ is cyano (B) for a compound of formula I where Z is COOH,

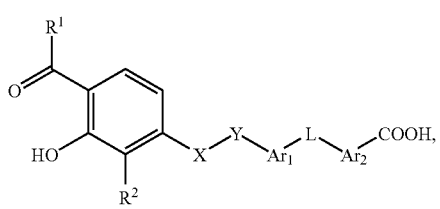

Z is COOH hydrolysis of a compound of formula II where $R^{10}$ is carboxylic acid ester;

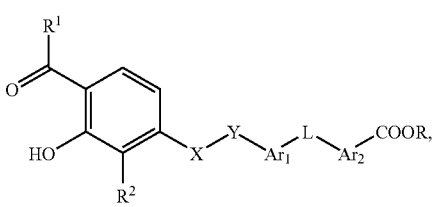

$R^{10}$ is COOR (C) for a compound of formula I where Z is COOH,

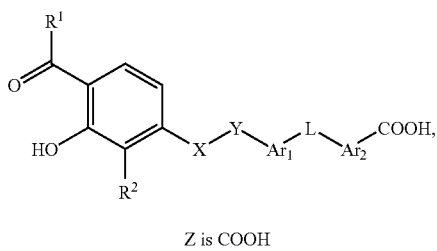

Z is COOH hydrolysis of a compound of formula II where $R^{10}$ is cyano; and

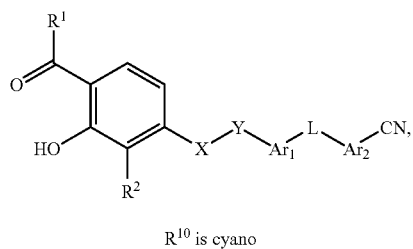

$R^{10}$ is cyano whereafter, when a pharmaceutically acceptable salt of the compound of formula I is required, it is obtained by reacting the acid of formula I with a physiologically acceptable base or by reacting a basic compound of formula I with a physiologically acceptable acid or by any other conventional procedure.

Chemical Abstracts discloses 5-[[6-[(4-acetyl-3-hydroxy-2-propylphenoxy)-methyl]-2-pyridinyl]methoxy]-2-butoxybenzoic acid ethyl ester.

A further embodiment of the present invention provides intermediate compounds useful for the preparation of a compound of formula I. More specifically, the present invention provides a compound of formula II

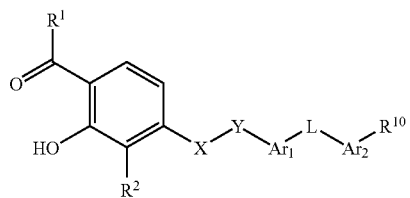

wherein $R^1$, $R^2$, X, Y, $Ar_1$, $Ar_2$ and L are defined as above; and $R^{10}$ is CN or $COOR^{14}$ in which $R^{14}$ is selected from the group consisting of C1-C5 alkyl, phenyl and benzyl; other than 5-[[6-[(4-acetyl-3-hydroxy-2-propylphenoxy)-methyl]-2-pyridinyl]methoxy]-2-butoxybenzoic acid ethyl ester. A particular value of $R^{14}$ is methyl.

Compounds of the present invention may be made by a process which is analogous to one known in the chemical art for the production of structurally analogous compounds or by a novel process described herein. Such processes useful for the manufacture of a compound of formula I as defined above are provided as further features of the invention and are illustrated by the following procedures in which, unless otherwise specified, the meanings of the generic radicals are as defined above and all reagents are well known and appreciated in the art.

Generally, a compound of formula I may be prepared from a compound of formula II where $R^{10}$ represents a precursor to Z (Reaction Scheme A, step a). More specifically, a compound of formula II where $R^{10}$ is carboxylic acid ester or nitrile is reacted with a suitable base such as potassium hydroxide in a suitable solvent such as water to provide a compound of formula I where Z is carboxylic acid. Additionally, a compound of formula II where $R^{10}$ is cyano is reacted with an azide reagent to provide a compound of formula I where Z is tetrazolyl. Azide reagents include $HN_3$ wherein $HN_3$ is provided from the reaction of sodium azide and a protic acid such as triethylamine hydrochloride and ammonium chloride. The reaction is conveniently in a solvent such solutions of water and an organic co-solvent wherein the organic cosolvent is an alcohol such as isopropyl alcohol or a tertiary amide such as N-methylpyrrolidinone. Other examples of azide reagents include transition metal azide complexes such as provided from the reaction of zinc bromide and sodium azide, as well as the trialkylsilylazides such as trimethylsilylazide. A compound of formula II where $R^{10}$ is an acid halide is reacted in one or more steps with cyclocondensating agents to provide a compound of formula I where Z is

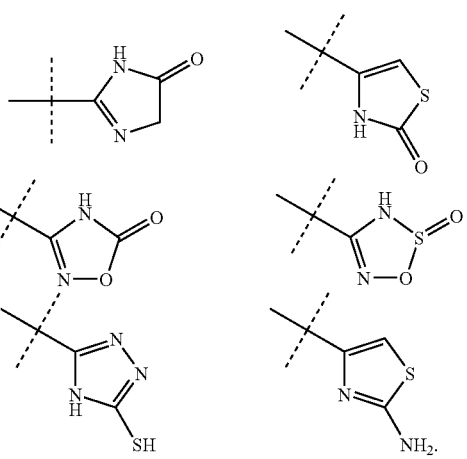

A compound of formula of II may be prepared from a compound of formula III (Reaction Scheme A, step b) or, alternatively, from a compound of formula V (Reaction Scheme A, step c). More specifically in step b, a compound of formula III where X is O is reacted under Mitsunobu conditions with a compound of formula IV where $R^{11}$ is OH in the presence of an organophosphine such as tributylphosphine and an appropriate azodicarbonyl reagent such as 1,1'-(azodicarbonyl)dipiperidine to provide a compound of formula II. Suitable solvents include toluene and dichloromethane. In step b, a compound of formula II may also be prepared by reacting a compound of formula III where X is O, S, NH with a compound of formula IV where $R^{11}$ is a leaving group in the presence of a suitable base such as cesium carbonate and a suitable solvent such as acetone. Suitable leaving groups include halides such as iodide, and sulfonate esters such as methanesulfonate ester.

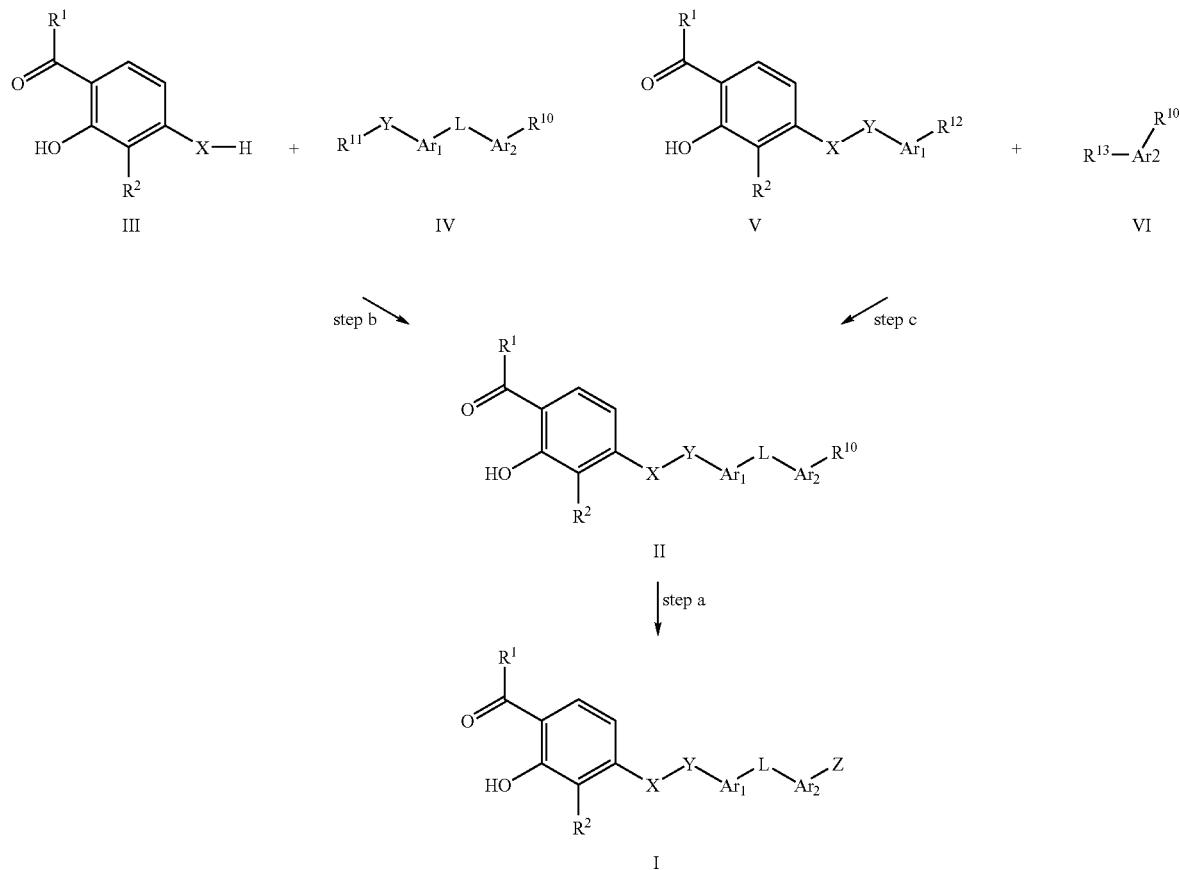

Reaction Scheme A

Alternatively, a compound of formula of II may be prepared from a compound of formula V (Reaction Scheme A, step c) where $R^{12}$ is an appropriate precursor to the group L. More specifically, a compound of formula V where $Ar_1$ is pyridinediyl and $R^{12}$ is a leaving group is reacted with a compound of formula VI where $R^{13}$ is thiol in a solvent such dimethylformamide to provide a compound of formula II where L is S. Suitable leaving groups include a halide such as chloride.

A compound of formula III where $R^2$ is halo, phenyl, substituted phenyl, thiophenyl, substituted thiophenyl and the like maybe prepared from a compound of formula VII (Reaction Scheme B). More specially, a compound of formula VII where X is O is reacted under the appropriate halogenation conditions to provide a compound of formula III where X is O and $R^2$ is a halogen such as chloro, bromo or iodo. A compound of formula III where X is O and $R^2$ is a halogen such as chloro, bromo or iodo is reacted with a boronic acid of phenyl, substituted phenyl, thiophenyl, substituted thiophenyl and the like in the presence of a transition metal catalyst such as $Pd(dppf)_2Cl_2$ and a base such as cesium hydroxide to provide a compound of formula III where $R^2$ is the corresponding phenyl, substituted phenyl, thiophenyl, substituted thiophenyl and the like. The reaction is conveniently carried out in a solvent such as solutions of tetrahydrofuran and water.

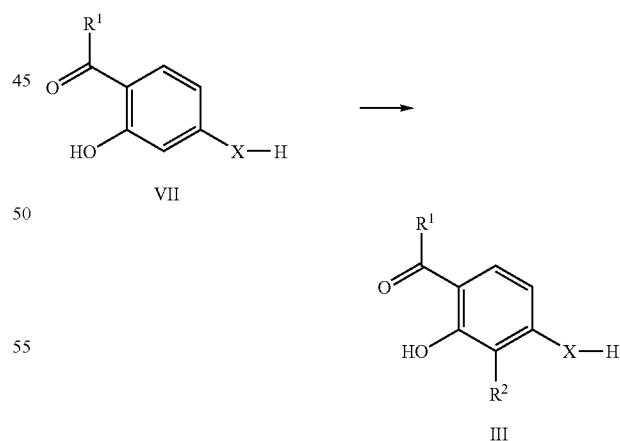

Reaction Scheme B

A compound of formula III where X is S may be prepared from a compound of formula III where X is O. More specifically, a compound of formula III where X is O is reacted with dimethylthiocarbamoyl chloride in a suitable solvent such as dichloromethane. The resulting thiocarbamate is heated in a suitable solvent such as dodecane and treated with sodium hydroxide to provide a compound of formula III where X is S.

A compound of formula III may also be prepared from a compound of formula IX where the group Pg represents a suitable protecting group (Reaction Scheme C). More specifically in step a, a compound of formula IX where $R^2$ is a halogen such iodo or bromo and Pg is methyl, is reacted with a boronic acid of phenyl, substituted phenyl, thiophenyl, substituted thiophenyl and the like in the presence of a transition metal catalyst such as Pd(dppf)$_2$Cl$_2$ and a base such as cesium hydroxide to provide a compound of formula IX where $R^2$ is phenyl, substituted phenyl, thiophenyl, substituted thiophenyl and the like, and Pg is methyl. The reaction is conveniently carried out in a solvent such as a solution of tetrahydrofuran and water. Further in step a, a compound of formula IX where $R^2$ is phenyl, substituted phenyl, thiophenyl, substituted thiophenyl and the like is reacted with an $R^1$ acyl halide such as acetyl chloride and a Lewis acid such as aluminum chloride in a suitable solvent to provide a compound of formula VIII where $R^1$ is methyl and $R^2$ is phenyl, substituted phenyl, thiophenyl, substituted thiophenyl and the like. Suitable solvents include dichloromethane. In step b, a compound of formula VIII where the group Pg is methyl is reacted with deprotection agents such as pyridine hydrochloride in the presence of microwave radiation to provide a compound of formula III where $R^2$ is phenyl, substituted phenyl, thiophenyl, substituted thiophenyl and the like.

trifluoromethyl, X is O, and Pg is benzyl. Suitable solvents include dimethylformamide. In step c, a compound of formula IX where $R^2$ is trifluoromethyl, X is O, and Pg is benzyl is reacted N-bromosuccinimide in a suitable solvent such as dimethylformamide to provide a compound of formula X. In step d, a compound of formula X is reacted with tributyl-(1-ethoxy-vinyl)-stannane and a transition metal catalyst such as tetrakis(triphenylphosphine)palladium in a solvent such as dioxane followed by acid hydrolysis to provide a compound of formula VIII where $R^1$ is methyl, $R^2$ is trifluoromethyl, X is O, and Pg is benzyl. In step b, a compound of formula VIII where $R^1$ is methyl, $R^2$ is trifluoromethyl, X is O, and Pg is benzyl is reacted with a transistion metal catalyst such as palladium hydroxide in the presence of an effective hydrogen source such as cyclohexene to provide a compound of formula III where $R^1$ is methyl, $R^2$ is trifluoromethyl, and X is O, Suitable solvents include ethanol.

A compound of formula IV where L is 0 may be prepared under aryl ether forming conditions as outlined in Reaction Scheme D. More specifically in step a, a compound of formula XII where $R^{10}$ represents a precursor to Z is reacted with a compound of formula XI where A is N and $R^{14}$ is chloro in the presence of a suitable base such as potassium carbonate to

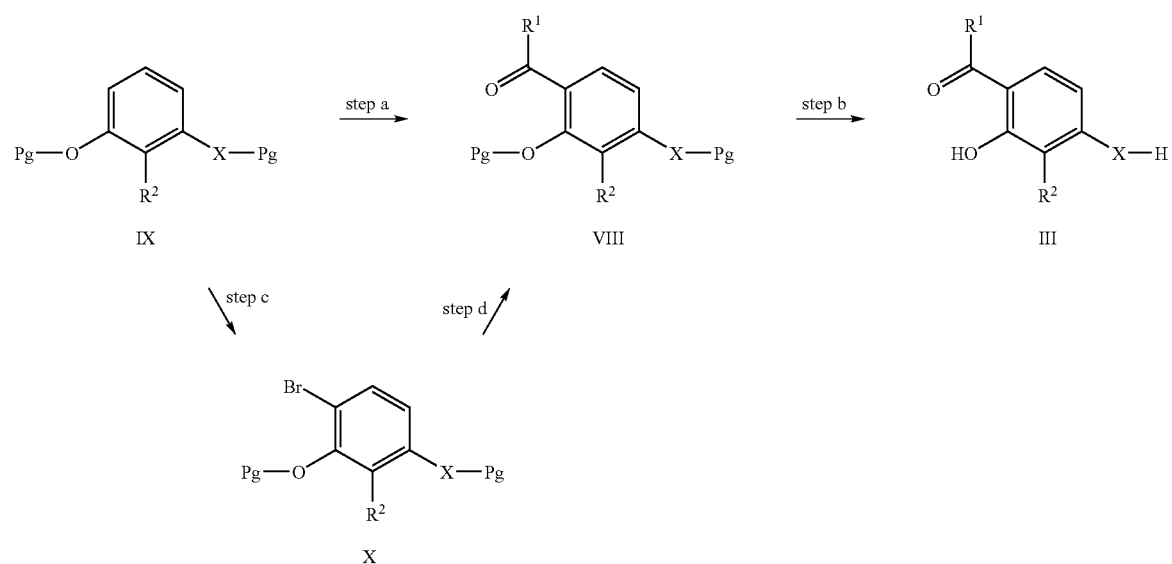

Additionally in Reaction Scheme C, a compound of formula III where $R^2$ is C1-C3 fluoroalkyl may be prepared from a compound of formula IX where $R^2$ is a halogen. More specifically, a compound of formula IX where $R^2$ is iodo, X is O and Pg is a suitable protecting group such as benzyl is reacted with an alkyl ester of difluoro-fluorosulfonyl-acetic acid in the presence of hexamethylphosphoramide and a transistion metal catalyst such as copper iodide in a suitable solvent to provide a compound of formula IX where $R^1$ is provide a compound of formula XIII where A is N. The reaction is conveniently carried out in a solvent such as dimethylacetamide. Analogously, a compound of formula XII where $R^{10}$ represents a precursor to Z is reacted with a compound of formula XI where A is CH and $R^{14}$ is fluoro in the presence of a suitable base such as potassium carbonate to provide a compound of formula XIII where A is CH. The reaction is conveniently carried out in a solvent such as dimethylacetamide.

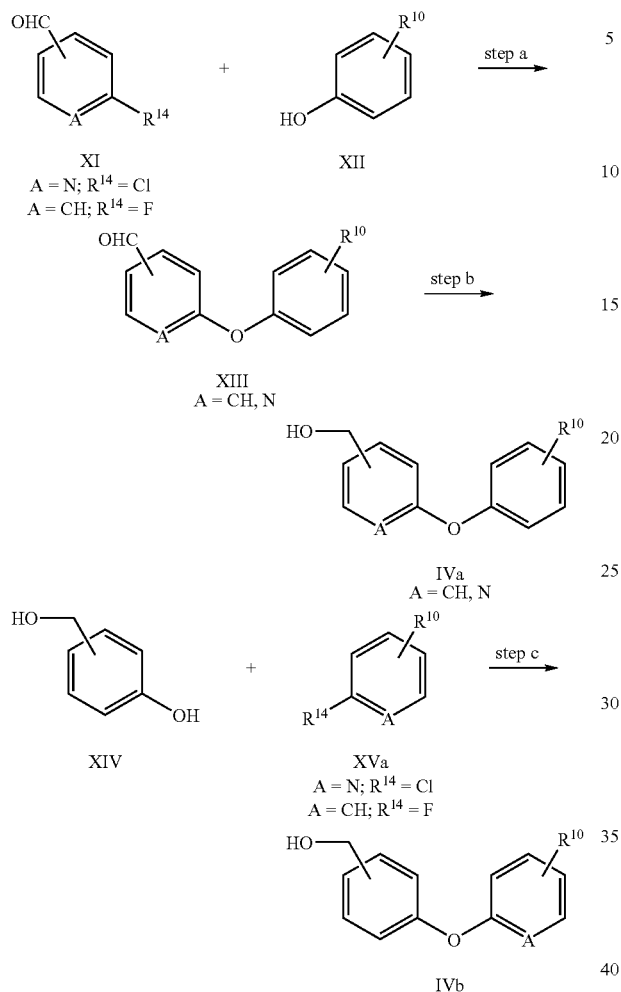

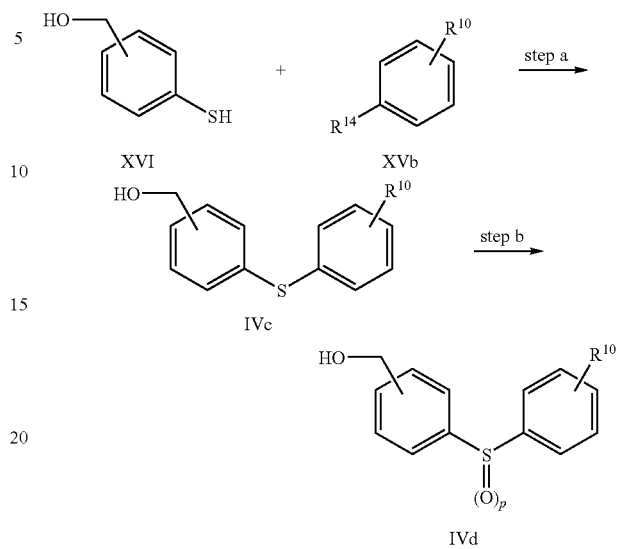

In Reaction Scheme D, step b, a compound of formula XIII where A is CH or N is reacted with a reducing agent such as sodium borohydride in a suitable solvent such as methanol to provide a compound of formula IVa where A is CH or N. In step c, a compound of formula XVa where A is N and $R^{14}$ is chloro or alternatively a compound where A is CH and $R^{14}$ is fluoro is reacted with a compound of formula XIV in the presence of a suitable base such as potassium carbonate to provide a compound of formula IVb where A is N or CH. The reaction is conveniently carried out in a solvent such as dimethylacetamide.

A compound of formula IV where L is $S(O)_p$ and p is 0, 1 or 2 may be prepared from a compound of formula XVb as outlined in Reaction Scheme E. More specifically in step a, a compound of formula XVb where $R^{14}$ is a halogen such as iodo is reacted with a compound of formula XVI, copper (I) chloride and a suitable base such as cesium carbonate to provide a compound of formula IVc. The reaction is conveniently carried out in a solvent such as N-methylpyrrolidinone. In step b, a compound of formula IVc is reacted with a suitable oxidizing agent such as potassium peroxymonosulfate in a solvent such as methanol to provide a compound of formula IVd where p is 1 or 2.

In Reaction Scheme F step a, a compound of formula XIV is reacted sequentially with a suitable base such as sodium hydride and a compound of formula XVc where $R^{14}$ is a halogen such as chloro in a suitable solvent such as dimethylformamide to provide a compound of formula XVI. In step b, a compound of formula XVI is reacted with an acyl halide forming agent such as thionyl chloride to form an intermediate acid chloride which is reacted with a suitable reducing agent such as sodium borohydride in suitable solvent such as dioxane to provide a compound of formula IVe.

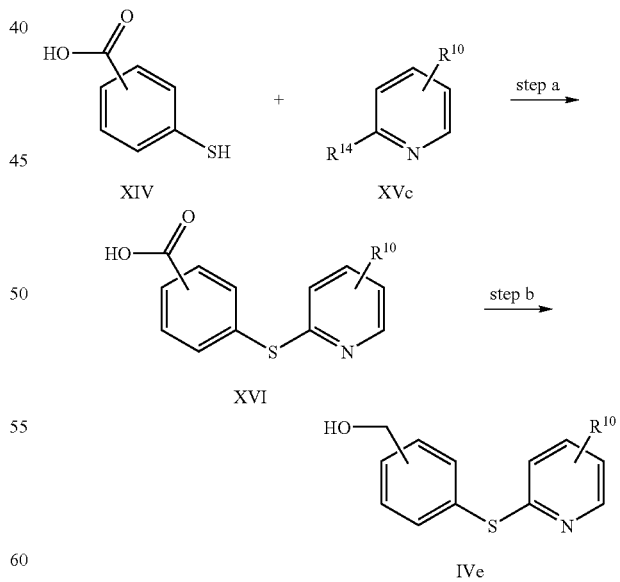

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

In practice, the compounds of formula I are usually administered in the form of pharmaceutical compositions, that is, in admixture with pharmaceutically acceptable carriers or diluents, the proportion and nature of which are determined by the chemical properties of the selected compound of formula I, the chosen route of administration, and standard pharmaceutical practice.

Thus, the present invention provides pharmaceutical compositions comprising a compound of the formula I and a pharmaceutically acceptable carrier, diluent or excipient.

The compounds of formula I can be administered by a variety of routes. In effecting treatment of a patient afflicted with disorders described above, a compound of formula I can be administered in any form or mode which makes the compound bioavailable in an effective amount, including oral and parenteral routes. For example, compounds of formula I can be administered orally, by inhalation, subcutaneously, intramuscularly, intravenously, transdermally, intranasally, rectally, ocularly, topically, sublingually, buccally, and the like. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences*, 18th Edition, Mack Publishing Co. (1990)).

The pharmaceutical compositions of the present invention are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. A person skilled in the art may determine preferred compositions and preparations according to the present invention.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I or its pharmaceutical salt from about 0.1 to about 10% w/v (weight per unit volume).

The compounds of formula I are potentiators of metabotropic glutamate (mGlu) receptor function, in particular they are potentiators of mGlu2 receptors. That is the compounds of formula I increase mGlu2 receptor response to glutamate or a glutamate agonist, enhancing the function of the receptors. The behavior of the potentiators of formula I at mGlu2 receptors is shown in Example A which is suitable to identify potentiators useful for carrying out the present invention. Thus, the potentiators of the present invention are expected to be useful in the treatment of various neurological and psychiatric disorders associated with glutamate dysfunction described to be treated herein and others that can be treated by such potentiators as are appreciated by those skilled in the art.

EXAMPLE A

Potentiation of Glutamate-Induced Increase in Intracellular Calcium with a mGlu2 Expressing Cell Line.

Cell lines expressing human mGlu2 receptors are derived as previously described (Desai, Burnett, Mayne, Schoepp, *Mol. Pharmacol.* 48, 648-657, 1995) and cultured in DMEM with 5% dialyzed fetal bovine serum, 1 mM glutamine, 1 mM sodium pyruvate, 50 µg/mL Geneticin G418, and 0.2 mg/mL hygromycin B. Confluent cultures are passaged weekly. These cells are referred to as RGT cells for Rat Glutamate Transporter, and have been co-transfected with the glutamate/ aspartate transporter GLAST. The RGT cell line expressing the mGlu2 receptors is stably transfected with the promiscuous G-protein, Galpha15 to change the signaling pathway to the mGlu2 receptor to one that could be easily measured through release of intracellular calcium. Thus, intracellular calcium levels are monitored before and after the addition of drugs on a Fluorometric Imaging Plate Reader (i.e. FLIPR, Molecular Devices). The following buffer is used throughout as an assay buffer: 10 mM KCl, 138 mM NaCl, 5 mM $CaCl_2$, 1 mM $MgC_2$, 4 mM $Na H_2PO_4$, 10 mM Glucose, 10 mM HEPES, pH 7.4. Cells that had been plated 48 hours prior at a density of 30-40,000 cells per well in a 96-well plate are loaded with a calcium-sensitive dye for 90 minutes at 25° C. Fluo-3 (2 mM in DMSO, Molecular Probes) are mixed with a equal volume of 10% pluronic acid in DMSO, and diluted to 8 μM into the buffer described above containing 10% fetal bovine serum to make the loading buffer. Following loading of the cells, the loading buffer is removed and replaced with assay buffer prior to drug addition and monitoring on the FLIPR. The resulting signal from the addition of compounds of formula (I) and submaximal concentrations of a glutamate-site agonist (e.g. 1 μM glutamate) is determined by taking the difference of the maximal fluorescent peak height minus the background fluorescence in each well and expressing the results as a percent of the signal seen with a maximal glutamate response (30 μM glutamate, typically about 30-50,000 Relative Fluorescent Units). Least squares curve fitting with a four-parameter equation is then applied to the resulting dose-% response curve to determine the resulting EC50 values.

Exemplified compounds of formula I typically affect the potentiation of mGlu2 receptors with EC50 values less than 12.5 μM. More specifically, examples 21, 22, 27, and 84 affect the potentiation of mGlu2 receptors with EC50 values less than 350 nM.

Compounds of formula I are modulators of leukotriene receptor function, in particular they are antagonists of leukotriene receptors. That is the compounds of formula I antagonize the cysteinyl-leukotriene D4 (LTD4) receptor. The behavior of the antagonism of the cysteinyl-leukotriene D4 (LTD4) receptor by compounds of formula I is shown in Example B which is suitable to identify antagonists useful for carrying out the present invention. Thus, the leukotriene antagonists of the present invention are useful in the treatment of various inflammatory and allergic disorders mediated by leukotrienes and described to be treated herein and other disorders that can be treated by such antagonists as are appreciated by those skilled in the art.

EXAMPLE B

Antagonism of Cysteinyl-leukotriene D4 (LTD4)-Induced Increase in Intracellular Calcium within a Cysteinyl-Leukotriene 1 (CysLT1) Receptor Expressing Cell Line.

Cell lines expressing the human CysLT1 receptor [AV12-664 (ATCC-9595)] are derived and maintained in culture media: DMEM with 5% dialyzed fetal bovine serum, 1 mM glutamine, and 1 mM sodium pyruvate. Confluent cultures are passaged weekly. Intracellular calcium levels are monitored in the CysLT1-expressing cells with the addition of LTD4, with or without prior exposure to the compounds being tested as antagonists with a Fluorometric Imaging Plate Reader (FLIPR, Molecular Devices). The following buffer is used throughout as an assay buffer: Hanks Buffered Saline Solution without phenol red (GIBCO), with 10 mM HEPES pH 7.4. Cells that had been plated 48 hours prior at a density of 20-25,000 cells per well in a 96-well plate are loaded with a calcium-sensitive dye for 90 minutes at 25° C. Fluo-3 (2 mM in DMSO, Molecular Probes) is mixed with an equal volume of 10% pluronic acid in DMSO, and diluted to 8 μM in the buffer described above containing 10% fetal bovine serum to make the loading buffer. Following loading of the cells, the buffer is removed and replaced with assay buffer prior to drug addition and monitoring on the FLIPR for several minutes. The resulting signal from the addition of 6 nM LTD4 (provides approximately 90% of the maximal signal with 25 nM LTD4) is determined by taking the difference of the maximal fluorescent peak height minus the background fluorescence in each well and expressing the results as a percent of the signal seen without pretreatment of the test compound(s). Least squares curve fitting with a four-parameter equation is applied to the resulting dose-% inhibition curve to determine the resulting IC50 values.

Exemplified compounds of formula I typically affect the antagonism of CysLT1 receptors with IC50 values less than 12.5 μM. More specifically, examples 21, 27 and 84 affect the antagonism of CysLT1 receptors with IC50 values less than 150 nM.

In one embodiment of the present invention provides methods of treating neurological and psychiatric disorders associated with glutamate dysfunction, comprising administering to a patient in need thereof an effective amount of a potentiator of metabotropic glutamate 2 receptors.

Specifically, the present invention provides a method of treating neurological and psychiatric disorders associated with glutamate dysfunction, comprising administering to a patient in need thereof an effective amount of a potentiator of the mGlu2 receptor and/or antagonist of the CysLT1 receptor, that is, the present invention provides methods using an effective amount of a potentiator of mGlu2 receptors and/or antagonist of the CysLT1 receptor.

In a preferred embodiment the present invention provides a method of treating migraine, comprising administering to a patient in need thereof an effective amount of a compound of formula I.

In another preferred embodiment the present invention provides a method of treating anxiety, comprising administering to a patient in need thereof an effective amount of a compound of formula I.

Particularly preferred anxiety disorders are generalized anxiety disorder, panic disorder, and obsessive compulsive disorder.

In another preferred embodiment the present invention provides a method of treating schizophrenia, comprising administering to a patient in need thereof an effective amount of a compound of formula I.

In yet another preferred embodiment the present invention provides a method of treating epilepsy, comprising administering to a patient in need thereof an effective amount of a compound of formula I.

Because the compounds of formula I enhance the normal physiological function of the mGlu receptors, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity (including tremors) seizures, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

At present, the fourth edition of the Diagnostic and Statistical Manual of Mental Disorders (DSM-IV™) (1994, American Psychiatric Association, Washington, D.C.), provides a diagnostic tool for identifying many of the disorders described herein. The skilled artisan will recognize that there are alternative nomenclatures, nosologies, and classification systems for neurological and psychiatric disorders described herein and that these systems evolve with medical scientific progress.

The compounds of formula I potentiate mGlu receptor response, in particular mGlu2 receptor response, to glutamate and glutamate agonists. Such agonists are easily recognized and some are available in the art. Schoepp, D. D., Jane, D. E., Monn, J. A., *Neuropharmacology* 38: 1431-1476, (1999).

Thus, a more particular embodiment, it is understood that the present invention extends to a method of potentiating the action of a glutamate receptor agonist at the Group II mGlu receptors, comprising administering to a patient in need thereof an effective amount of a mGlu2 potentiator, in particular a compound of formula I, in combination with a potentiated amount of an mGlu receptor agonist. Such a combination may be advantageous in that it may augment the activity and selectivity of mGlu agonist.

As used herein, the term "patient" refers to a warm blooded animal such as a mammal which is afflicted with one or more neurological and psychiatric disorders associated with glutamate dysfunction. It is understood that guinea pigs, dogs, cats, rats, mice, horses, cattle, sheep, and humans, particularly humans, are examples of animals within the scope of the meaning of the term. It is also understood that this invention relates specifically to the potentiation of mammalian metabotropic glutamate receptors.

It is also recognized that one skilled in the art may affect the neurological and psychiatric disorders by treating a patient presently afflicted with the disorders or by prophylactically treating a patient afflicted with the disorders with an effective amount of the compound of formula I. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

As used herein, the term "effective amount" of a compound of formula I refers to an amount, that is, the dosage which is effective in treating the neurological and psychiatric disorders described herein.

The attending diagnostician, as one skilled in the art, can readily determine an effective amount by the use of conventional techniques and by observing results obtained under analogous circumstances. In determining an effective amount, the dose of a compound of formula I, a number of factors are considered by the attending diagnostician, including, but not limited to: the compound of formula I to be administered; the co-administration of an mGlu agonist, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.01 milligram per kilogram of body weight per day (mg/kg/day) to about 100 mg/kg/day. Preferred amounts may be determined by one skilled in the art.

As used herein, the term "potentiated amount" refers to an amount of an mGlu agonist, that is, the dosage of agonist which is effective in treating the neurological and psychiatric disorders described herein when administered in combination with an effective amount of a compound of formula I. A potentiated amount is expected to be less than the amount that is required to provided the same effect when the mGlu agonist is administered without an effective amount of a compound of formula I.

The attending diagnostician, as one skilled in the art, can readily determine a potentiated amount by the use of conventional techniques and by observing results obtained under analogous circumstances. In determining a potentiated amount, the dose of an mGlu agonist to be administered in combination with a compound of formula I, a number of factors are considered by the attending diagnostician, including, but not limited to: the mGlu agonist selected to be administered, including its potency and selectivity; the compound of formula I to be co-administered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGlu agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

Of the neurological and psychiatric disorders associated with glutamate dysfunction which are treated according to the present invention, the treatment of migraine, anxiety, schizophrenia, and epilepsy are particularly preferred. Particularly preferred anxiety disorders are generalized anxiety disorder, panic disorder, and obsessive compulsive disorder.

Thus, in a preferred embodiment the present invention provides a method of treating migraine, comprising administering to a patient in need thereof an effective amount of a compound of formula I or a pharmaceutical composition thereof.

In one of the available sources of diagnostic tools, *Dorland's Medical Dictionary* (23$^{rd}$ Ed., 1982, W.B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment the present invention provides a method of treating anxiety, comprising administering to a patient in need thereof an effective amount of a compound of formula I or a pharmaceutical composition thereof.

At present, the fourth edition of the Diagnostic and Statistical Manual of Mental Disorders (DSM-IV™) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

A number of preclinical laboratory animal models for migraine and anxiety have been described. One commonly used model of migraine is the dural extravasation model that has been described by Phebus et al., Life Sci., 61(21), 2117-2126 (1997) which can be used to evaluate the present compounds.

EXAMPLE C

Animal Model of Dural Plasma Protein Extravasation (PPE).

Male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagital scalp incision, two pairs of bilateral holes are drilled through the skull (3.2 mm posterially, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

The femoral vein is exposed and a dose of the test compound is injected intravenously (i.v.) at a dosing volume of 1 mL/kg. Approximately 8 minutes post i.v. injection, a 20 mg/kg dose of Fluorescein isothiocyanate-bovine serum albumin (FITC-BSA) is also injected intravenously. The FITC-BSA functions as a marker for protein extravasation. Exactly 10 minutes post-injection of the test compound, the left trigeminal ganglion is stimulated for 5 minutes at a current intensity of 1.0 mA (5 Hz, 5 msec duration) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 minutes later the animals are anesthetized and placed in the stereotaxic frame as described above. Exactly 58 minutes post-p.o. dosing, the animals are dosed with FITC-BSA (20 mg/kg, i.v.). Exactly one hour post-p.o. dosing, the animals are stimulated as described above.

Five minutes following stimulation, the animals are killed by exsanguination with 40 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monochromator and a spectrophotometer is used to quantify the amount of FITC-BSA in each sample. An excitation wavelength of approximately 490 nm is utilized and the emission intensity at 535 nm was determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0.

Examples 21, 22, 27 and 84 affect extravasation in the dura with $ID_{100}$ values less than or equal to 0.1 mg/kg p.o.

The fear potentiated startle response model has been extensively used as a model of anxiety and can be used to evaluate the present compounds. Davis, *Psychopharmacol*, 62, 1 (1979); Davis, *Behav. Neurosci.*, 100, 814 (1986); Davis, *Tr. Pharmacol. Sci.*, 13, 35 (1992).

EXAMPLE D

Fear Potentiated Startle Paradigm.

Male Sprague-Dawley rats weighing 325-400 g are purchased from Harlan Sprague-Dawley, Inc. (Cumberland, Ind.) and given a one week acclimation period before testing. Rats are individually housed with food and water ad libitum in an animal room on a 12-hour light/dark cycle with lights on between 6:00 A.M. and 6:00 P.M. The test compound of formula I is prepared in a suspension of 5% ethanol, 0.5% CMC, 0.5% Tween 80 and 99% water. 2S-2-amino-2-(1S,2S-2-carboxycyclopropan-1-yl)-3-(xanth-9-yl) propionic acid is prepared in sterile water. Control rats are given the respective vehicle.

The fear potentiated startle paradigm is conducted over three consecutive days. All three days begin with a 5-minute adaptation period before the trial starts. On day one (baseline startle) after the adaptation period, the animal receives 30 trials of 120 dB auditory noise. The mean startle amplitude ($V_{max}$) is used to assign animals to groups with similar means before conditioning begins. Day two consists of conditioning the animals. Each animal receives 0.5 mA of shock for 500 msec preceded by a 5 second presentation of light which remains on for the duration of the shock. Ten presentations of the light and shock are administered. Day three is the testing trial where drug administration occurs prior to testing. Twenty-four hours after conditioning, startle testing sessions are conducted. Ten trials of acoustic startle (120 dB), non-light paired, are presented at the beginning of the session. This is followed by 20 random trials of the noise alone and 20 random trials of noise preceded by light. Excluding the first 10 trials, the startle response amplitudes for each trial type are averaged for each animal. Data is presented as the difference between light+noise and noise-alone. Differences in startle response amplitudes are analyzed by JMP statistical software using a One-way Anova (analysis of variance, t-test). Group differences are considered to be significant at p<0.05.

In another preferred embodiment the present invention provides a method of treating epilepsy, comprising administering to a patient in need thereof an effective amount of a compound of formula I or a pharmaceutical composition thereof.

At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

Various electroshock-induces models has been extensively used as a model of seizure disorders.

EXAMPLE E

Electroshock-induced Seizures.

Application of electrical stimulation by corneal electrodes to mice can induce tonic hindlimb-extensor seizures. Blockade of tonic extensor seizures induced by electroshock is considered predictive for drugs which block seizure propagation and may be effective in preventing various seizures in humans, including epileptic seizures.

Vehicle or a dose of a test drug are administered to groups of 5 to 10 mice each. Thirty minutes later, electroshock (10 mA, 0.2 sec duration) is administered by transcorneal electrodes. The number of mice exhibiting tonic extensor seizures in each group is recorded. The data are reported as the percentage of mice that are protected from seizures.

The chemical nomenclature used in the examples and preparations is derived from one or more standard conventions. The skilled artisan will recognize the technical meaning when names are derived from two or more conventions.

The terms used in the examples and preparations have their normal meanings unless otherwise designated. For example, "° C." refers to degrees Celsius; "N" refers to normal or normality; "M" refers to molar or molarity; "mol" refers to mole or moles; "mmol" refers to millimole or millimoles; "mmol" refers to micromole or micromoles; "kg" refers to kilogram or kilograms; "g" refers to gram or grams; "mg" refers to microgram or micrograms; "mg" refers to milligram or milligrams; "mL" refers to microliter or microliters; "mL" refers milliliter or milliliters; "L" refers to liter or liters; "bp" refers to boiling point; "mp" refers to melting point; "brine" refers to a saturated aqueous sodium chloride solution; "h or hr" refers to hour or hours; "mim" refers to minute or minutes; "MS" refers to mass spectrometry; "NMR" refers to nuclear magnetic resonance spectroscopy; "TFA" refers to trifluoroacetic acid; "$CH_2Cl_2$" or "DCM" refers to dichloromethane; "DCE" refers to dichloroethane; "MeOH" refers to methanol; "$NH_4OH$" refers to a concentrated aqueous ammonia solution; "HCl" refers to hydrogen chloride; "MTBE" refers to tert-butyl methyl ether; "DSC" refers to differential scanning calorimetery; "DMEM" refers to Dulbecco's modified eagle medium. Chemical shifts are give in 6 and NMR spectra were obtained in $CDCl_3$, unless otherwise indicated.

Preparation 1

Synthesis of 6-(3-hydroxymethyl-phenoxy)-nicotinonitrile.

Add 3-hydroxybenzyl alcohol (0.99 g, 7.94 mmol) and potassium carbonate (1.50 g, 10.83 mmol) to 6-chloronicotinitrile (1.00 g, 7.22 mmol) in dimethylacetamide (25 mL) and stir. Heat to 100° C. for 4 hrs. Let cool to ambient temperature and pour into water (100 mL). Extract with diethyl ether (3×100 mL). Combine the organic layers and wash with 1N NaOH (2×50 mL) and dry over magnesium sulfate. Filter and concentrate under reduced pressure to give the product (1.63 g, 99%): $^1$H NMR ($CDCl_3$) 8.49 (d, J=2.2 Hz, 1H), 7.95 (dd, J=2.2 Hz, 8.7 Hz, 1H), 7.47 (t, J=7.9 Hz, 1H), 7.29 (s, 1H), 7.21 (s, 1H), 7.10 (d, J=8.2 Hz, 1H), 7.06 (d, J=8.7 Hz, 1H), 4.77 (s, 2H).

The following compounds are prepared essentially as described in Preparation 1.

| Prep. No. | Chemical name | Structure | Physical data |
|---|---|---|---|
| 2 | 6-(4-Hydroxymethyl-phenoxy)-nicotinonitrile | 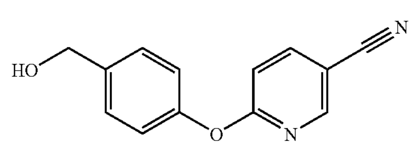 | $^1$H NMR ($CDCl_3$) 8.49 (d, 2.1 Hz, 1H), 7.96 (d6, J = 2,4 Hz, 8.6 Hz, 1H), 7.49 (d, J = 8.6 Hz, 2H), 7.17 (d, J = 8.6 Hz, 2H), 7.07 (d, J = 8.6 Hz, 1H), 4.77 (s, 2H). |

| Prep. No. | Chemical name | Physical data |
|---|---|---|
| 3 | 2-(3-Hydroxymethyl-phenoxy)-nicotinonitrile | ¹H NMR (CDCl₃) 8.33 (dd, J = 2.1 Hz, 4.9 Hz, 1H), 8.04 (dd, J = 1.9 Hz, 7.5 Hz, 1H), 7.44 (t, J = 7.8 Hz, 1H), 7.29 (d, J = 7.8 Hz, 1H), 7.24 (s, 1H), 7.16-7.11 (m, 2H), 4.75 (s, 2H). |
| 4 | 2-(3-Hydroxymethyl-phenoxy)-isonicotinonitrile | ¹H NMR (CDCl₃) 8.35 (d, J = 5.1 Hz, 1H), 7.46 (t, J = 7.8 Hz, 1H), 7.31-7.27 (m, 1H), 7.24 (d, J = 5.1 Hz, 1H), 7.21-7.18 (m, 2H), 7.09 (d, J = 8.1 Hz, 1H), 4.77 (s, 2H). |
| 5 | 2-(4-Hydroxymethyl-phenoxy)-isonicotinonitrile | ¹H NMR (CDCl₃) 8.35 (d, J = 5.0 Hz, 1H), 7.48 (d, J = 8.5 Hz, 2H), 7.23 (d, J = 5.0 Hz, 1H), 7.20 (s, 1H), 7.17 (d, J = 8.5 Hz, 2H), 4.76 (s, 2H). |
| 6 | 2-(4-Hydroxymethyl-phenoxy)-nicotinonitrile | ¹H NMR (CDCl₃) 8.35 (dd, J = 2.0 Hz, 5.0 Hz, 1H), 8.05 (dd, J = 2.0 Hz, 7.5 Hz, 1H), 7.49 (d, J = 8.5 Hz, 2H), 7.22 (d, J = 8.5 Hz, 2H), 7.13 (dd, J = 5.0 Hz, 7.5 Hz, 1H), 4.77 (s, 2H). |
| 7 | 3-(3-Hydroxymethyl-phenoxy)-5-trifluoromethyl-benzonitrile | ¹H NMR (CDCl₃) 7.63 (s, 1H), 7.50-7.44 (m, 2H), 7.37 (s, 1H), 7.32-7.27 (m, 1H), 7.14 (s, 1H), 7.01 (dd, J = 2.1 Hz, 8.1 Hz, 1H), 4.78 (s, 2H). |
| 8 | 2-(3-hydroxymethyl-phenoxy)-nicotinic acid methyl ester | ¹H NMR (CDCl₃) 8.85 (d, J = 2.1 Hz, 1H), 8.31 (dd, J = 2.1 Hz, 8.7 Hz, 1H), 7.46 (t, J = 7.9 Hz, 1H), 7.31-7.27 (m, 1H), 7.22 (s, 1H), 7.11 (d, J = 7.9 Hz, 1H), 6.98 (d, J = 8.7 Hz, 1H), 4.77 (s, 2H), 3.95 (s, 3H). |
| 9 | 3-(5-Hydroxymethyl-pyridin-2-yloxy)-benzonitrile | ¹H NMR (CDCl₃) 8.17 (s, 1H), 7.83 (dd, J = 2.0 Hz, 8.6 Hz, 1H), 7.54-7.49 (m, 2H), 7.47 (s, 1H), 7.44-7.40 (m, 1H), 7.03 (d, J = 8.6 Hz, 1H), 4.72 (s, 2H). |

Preparation 10

Synthesis of 3-(4-formyl-phenoxy)-benzonitrile.

The title compound is prepared essentially as described in Preparation 1 substituting 4-fluorobenzaldehyde (0.85 mL, 8.06 mmol) for 3-hydroxybenzyl alcohol and 3-hydroxybenzonitrile (1.06 g, 8.86 mmol) for 6-chloronicotinitrile. Yield (0.90 g, 50%); ¹H NMR (CDCl₃) 10.01 (s, 1H), 7.95 (d, J=8.5 Hz, 2H), 7.58-7.52 (m, 2H), 7.39-7.34 (m, 2H), 7.14 (d, J=8.5 Hz, 2H).

The following compounds are prepared essentially as described in Preparation 10.

| Prep. No. | Chemical name | Structure | Physical data |
|---|---|---|---|
| 11 | 2-(4-Formyl-phenoxy)-benzonitrile | 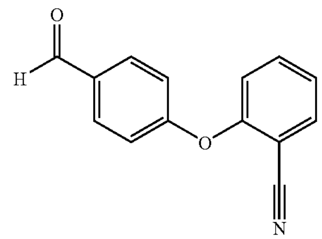 | $^1$H NMR (CDCl$_3$) 10.01 (s, 1H), 7.96 (d, J = 8.4 Hz, 2H), 7.76 (d, J = 7.7 Hz, 1H), 7.70-7.61 (m, 2H), 7.20 (d, J = 8.4 Hz, 2H), 7.10 (d, J = 8.4 Hz, 1H). |
| 12 | 2-(3-Formyl-phenoxy)-benzonitrile | 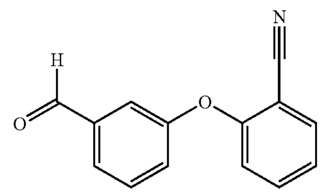 | $^1$H NMR (CDCl$_3$) 10.03 (s, 1H), 7.75 (t, J = 7.7 Hz, 2H), 7.63 (t, J = 8.0 Hz, 1H), 7.60-7.55 (m, 2H), 7.42 (d, J = 8.2 Hz, 1H), 7.26 (t, J = 7.7 Hz, 1H), 6.98 (d, J = 8.5 Hz, 1H). |
| 13 | 3-(5-Formyl-pyridin-2-yloxy)-benzonitrile | 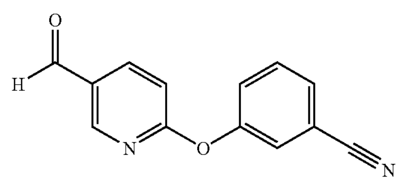 | $^1$H NMR (CDCl$_3$) 10.05 (s, 1H), 8.64 (d, J = 1.8 Hz, 1H), 8.29 (dd, J = 2.2 Hz, 8.6 Hz, 1H), 7.61-7.54 (m, 2H), 7.50-7.46 (m, 2H), 7.17 (d, J = 8.6 Hz, 1H). |

Preparation 14

Synthesis of 3-(4-hydroxymethyl-phenoxy)-benzonitrile.

Dissolve 3-(4-formyl-phenoxy)-benzonitrile of Preparation 10 (0.90 g, 4.04 mmol) in methanol (15 mL) and cool to 0° C. Add sodium borohydride (0.31 g, 8.08 mmol) in three batches. After 1 hr, allow to warm to ambient temperature and stir overnight. Concentrate under reduced pressure to give a residue. Dilute with ethyl acetate (50 mL) and wash with 1N hydrochloric acid (3×100 mL). Separate layers and dry the organic layer over magnesium sulfate, filter, and concentrate to a residue. Purification by flash chromatography, using 10% ethyl acetate/hexanes to 50% ethyl acetate/hexanes as a gradient eluent gives the title product (0.83 g, 91%): $^1$H NMR δ (CDCl$_3$) 7.48-7.38 (m, 4H), 7.30-7.23 (m, 2H), 7.06 (d, J=8.4 Hz, 2H), 4.75 (s, 2H).

The following compounds are prepared essentially as described in Preparation 14.

| Prep. No. | Chemical name | Structure | Physical data |
|---|---|---|---|
| 15 | 2-(4-Hydroxymethyl-phenoxy)-benzonitrile | 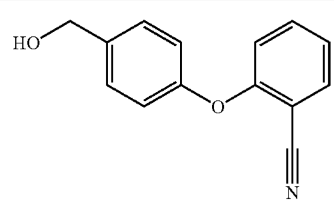 | $^1$H NMR (CDCl$_3$) 7.69 (d, J = 7.8 Hz, 1H), 7.50 (t, J = 8.2 Hz, 1H), 7.44 (d, J = 8.6 Hz, 2H), 7.17 (t, J = 7.6 Hz, 1H), 7.11 (d, J = 8.4 Hz, 2H), 6.89 (d, J = 8.4 Hz, 1H), 4.75 (s, 2H). |
| 16 | 2-(3-Hydroxymethyl-phenoxy)-benzonitrile | 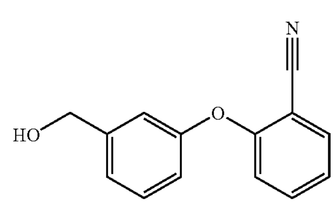 | $^1$H NMR (CDCl$_3$) 7.70 (d, J = 8.0 Hz, 1H), 7.51 (t, J = 8.0 Hz, 1H), 7.42 (t, J = 7.8 Hz, 1H), 7.24 (d, J = 7.6 Hz, 1H), 7.20-7.13 (m, 2H), 7.04 (d, J = 8.0 Hz, 1H), 6.92 (d, J = 8.6 Hz, 1H), 4.75 (s, 2H). |

| Prep. No. | Chemical name | Structure | Physical data |
|---|---|---|---|
| 17 | 4-(3-Hydroxymethyl-phenoxy)-benzonitrile | (structure) | $^1$H NMR (CDCl$_3$) 7.64 (d, J = 8.8 Hz, 2H), 7.44 (t, J = 7.8 Hz, 1H), 7.26 (t, J = 7.8 Hz, 1H), 7.13 (s, 1H), 7.06-7.01 (m, 3H), 4.76 (s, 2H). |

General Method 1

General procedure for the preparation of regioisomers of (hydroxymethyl-phenylsulfanyl)-benzonitrile.

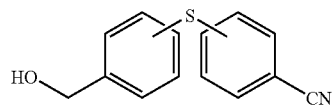

Add 2,2,6,6-tetramethyl-heptane-3,5-dione (0.250 mmol) to a solution of copper (I) chloride (0.500 mmol) in N-methylpyrrolidinone (0.300 M). Add cesium carbonate (2.00 mmol), the appropriate iodobenzonitrile (1.00 mmol), then the appropriate hydroxymethylthiophenol (2.00 mmol) and stir for 6 hours at 130° C. Dilute with ethyl acetate and wash with water. Dry and concentrate organic layer. Purify the residue by flash chromatography, eluting with hexanes, ramping to 50% ethyl acetate/hexanes to provide the title compound listed below.

| Prep. No. | Chemical Name | Physical Data |
|---|---|---|
| 18 | 3-(4-Hydroxymethyl-phenylsulfanyl)-benzonitrile | MS (m/z): 242 (M + 1). |
| 19 | 3-(2-Hydroxymethyl-phenylsulfanyl)-benzonitrile | $^1$H NMR (400 MHz, CDCl$_3$) δ 4.77 (s, 2H), 7.34 (m, 4H), 7.45 (m, 1H), 7.49 (m, 2H), 7.60 (m, 1H) |
| 20 | 4-(3-Hydroxymethyl-phenylsulfanyl)-benzonitrile | $^1$H NMR (400 MHz, CDCl$_3$) δ 4.72 (s, 2H), 7.18 (d, J = 9.0 Hz, 2H), 7.42 (s, 3H), 7.48 (d, J = 9.0 Hz, 2H), 7.53 (s, 1H) |
| 21 | 4-(2-Hydroxymethyl-phenylsulfanyl)-benzonitrile | $^1$H NMR (400 MHz, CDCl$_3$) δ 4.76 (s, 2H), 7.06 (d, J = 7.6 Hz, 2H), 7.38 (t, J = 11.3 Hz, 1H), 7.46 (d, J = 8.6 Hz, 2H), 7.51 (m, 2H), 7.64 (d, J = 7.0 Hz, 1H) |
| 22 | 2-(4-Hydroxymethyl-phenylsulfanyl)-benzonitrile | $^1$H NMR (400 MHz, CDCl$_3$) δ 4.73 (s, 2H), 7.13 (d, J = 8.6 Hz, 1H), 7.26 (m, 2H), 7.40 (d, J = 8.6 Hz, 2H), 7.47 (d, J = 6.2 Hz, 2H), 7.63 (d, J = 9.0 Hz, 1H). |
| 23 | 2-(3-Hydroxymethyl-phenylsulfanyl)-benzonitrile | $^1$H NMR (400 MHz, CDCl$_3$) δ 4.69 (s, 2H), 7.18 (d, J = 8.2 Hz, 1H), 7.27 (m, 1H), 7.38 (s, 3H), 7.41 (m, 1H), 7.48 (s, 1H), 7.64 (d, J = 9.4 Hz, 1H). |
| 24 | 4-(4-Hydroxymethyl-phenylsulfanyl)-benzonitrile | MS (m/z): 242 (M + 1). |
| 25 | 3-(4-Hydroxymethyl-phenylsulfanyl)-benzonitrile | MS (m/z): 242 (M + 1). |
| 26 | 3-(3-Hydroxymethyl-phenylsulfanyl)-benzoic acid ethyl ester | MS (m/z): 289 (M + 1). |
| 27 | 3-(4-Hydroxymethyl-phenylsulfanyl)-benzoic acid ethyl ester | MS (m/z): 289 (M + 1). |
| 28 | 4-(4-Hydroxymethyl-phenylsulfanyl)-benzoic acid ethyl ester | MS (m/z): 275 (M + 1). |

General Method 2

General procedure for the preparation of regioisomers of (hydroxymethyl-benzenesulfonyl)-benzonitriles.

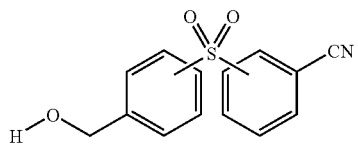

Add potassium peroxymonosulfate (1.00 g, 1.66 mmol) in water (0.5M) at room temperature to a solution of the appropriate hydroxymethylbenzenesulfanylbenzonitrile (0.829 mmol) in methanol (0.2M) at 0° C. Stir overnight and allow solution to warm to room temperature. Dilute with dichloromethane and 2N hydrochloric acid. Collect organic layer and extract aqueous layer with dichloromethane (3×). Dry organic layers with sodium sulfate and evaporate to dryness to afford the title compound listed below.

| Prep. No. | Chemical Name | Physical Data |
| --- | --- | --- |
| 29 | 2-(3-Hydroxymethyl-benzenesulfonyl)-benzonitrile | MS (m/z): 274 (M + 1). |
| 30 | 3-(3-Hydroxymethyl-benzenesulfonyl)-benzonitrile | MS (m/z): 274 (M + 1). |
| 31 | 4-(4-Hydroxymethyl-benzenesulfonyl)-benzonitrile | MS (m/z): 274 (M + 1). |
| 32 | 3-(4-Hydroxymethyl-benzenesulfonyl)-benzonitrile | MS (m/z): 274 (M + 1). |
| 33 | 4-(3-Hydroxymethyl-benzenesulfonyl)-benzonitrile | MS (m/z): 274 (M + 1). |
| 34 | 3-(3-Hydroxymethyl-benzenesulfonyl)-benzoic acid ethyl ester | MS (m/z): 321 (M + 1). |
| 35 | 3-(4-Hydroxymethyl-benzenesulfonyl)-benzoic acid ethyl ester | MS (m/z): 321 (M + 1). |
| 36 | 4-(4-Hydroxymethyl-benzenesulfonyl)-benzoic acid methyl ester | MS (m/z): 307 (M + 1). |

General Method 3

General procedure for the preparation of regioisomers of (hydroxymethyl-benzenesulfinyl)-benzonitrile.

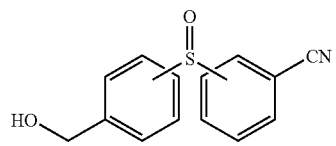

Add potassium peroxymonosulfate (1.00 g, 0.829) in water (0.5M) at 0° C. to a solution of the appropriate hydroxymethylbenzenesulfanylbenzonitrile (0.829 mmol) in methanol (0.2M) at 0° C. over 1 min. Quench reaction after 10 min with sodium bisulfite (sat). Dilute the mixture with 2N hydrochloric acid and extract with ethyl acetate (3×). Dry the organic layers with sodium sulfate and concentrate to dryness. Purify the resulting residue by flash chromatography, eluting with hexanes to 50% ethyl acetate/hexanes to provide the title compound listed below.

| Prep. No. | Chemical Name | Physical Data |
| --- | --- | --- |
| 37 | 3-(2-Hydroxymethyl-benzenesulfinyl)-benzonitrile | MS (m/z): 258 (M + 1). |
| 38 | 2-(3-Hydroxymethyl-benzenesulfinyl)-benzonitrile | MS (m/z): 258 (M + 1). |
| 39 | 4-(4-Hydroxymethyl-benzenesulfinyl)-benzonitrile | MS (m/z): 258 (M + 1). |
| 40 | 3-(4-Hydroxymethyl-benzenesulfinyl)-benzonitrile | MS (m/z): 258 (M + 1). |
| 41 | 3-(3-Hydroxymethyl-benzenesulfinyl)-benzonitrile | MS (m/z): 258 (M + 1). |

Preparation 42

Synthesis of 6-[3-(4-acetyl-3-hydroxy-2-propyl-phenoxymethyl)-phenoxy]-nicotinonitrile.

Mix 6-(3-hydroxymethyl-phenoxy)-nicotinonitrile (1.63 g, 7.18 mmol) and 1-(2,4-dihydroxy-3-propyl-phenyl)-ethanone (1.33 g, 6.84 mmol) in 2:1 toluene/dichloromethane (24 mL). Cool to −20° C. and add tributylphosphine (2.6 mL, 10.26 mmol) dropwise. After stirring for 5 minutes, add 1,1'-(azodicarbonyl)dipiperidine in three batches. Allow the reaction mixture to warm to ambient temperature overnight. Concentrate under reduced pressure to give a yellow solid. Dilute with diethyl ether (50 mL) and cool to 0° C. Filter the white precipitate and concentrate the filtrate under reduced pressure to give a residue. Purification by flash chromatography, using 5% ethyl acetate/hexanes to 30% ethyl acetate/hexanes as a gradient eluent yields the title compound (0.91 g, 33%): MS (m/z): 401.2 (M−1). $^1$H NMR (CDCl$_3$) 12.78 (s, 1H), 8.50 (s, 1H), 7.97 (dd, J=2.2 Hz, 8.8 Hz, 1H), 7.62 (d, J=8.8 Hz, 1H), 7.51 (t, J=8.0 Hz, 1H), 7.36 (d, J=7.8 Hz, 1H), 7.25 (s, 1H), 7.16 (d, J=8.0 Hz, 1H), 7.09 (d, J=8.8 Hz, 1H), 6.51 (d, J=8.8 Hz, 1H), 5.22 (s, 2H), 2.72 (t, J=7.6 Hz, 2H), 2.60 (s, 3H), 1.62-1.53 (m, 2H), 0.94 (t, J=7.6 Hz, 3H).

Preparation 43

Synthesis of 2-[3-(3-hydroxy-2-methyl-4-propionyl-phenoxymethyl)-phenoxy]-isonicotinonitrile.

Mix polymer-supported triphenylphosphine (2.33 mmol/g load capacity, 0.85 g, 1.99 mmol), imidazole (0.14 g, 1.99 mmol) and iodine (0.51 g, 1.99 mmol) in dichloromethane (8 mL) in a vial (0.75 oz). Seal and shake for 10 minutes. Add a solution of 2-(3-hydroxymethyl-phenoxy)-isonicotinonitrile (0.30 g, 1.33 mmol) in dichloromethane (3 mL) and shake for 2 hrs. Filter the resin and wash with dichloromethane (50 mL). Concentrate the filtrate under reduced pressure to give a residue. Dissolve the residue in ethyl acetate (25 mL), wash with saturated sodium thiosulfate solution (2×25 mL) and dry over sodium sulfate. Filter and concentrate to give 2-(3-iodomethyl-phenoxy)-isonicotinonitrile as a yellow solid (0.25 g, 53%). Mix the yellow solid (0.25 g, 0.70 mmol), 1-(2,4-dihydroxy-3-methyl-phenyl)-propan-1-one (0.14 g, 0.77 mmol) and cesium carbonate (0.25 g, 0.77 mmol) in acetone (7 mL). Heat to 50° C. for 2.5 hrs. Allow the reaction to cool to ambient temperature and concentrate under reduced pressure to give a solid. Dilute with ethyl acetate (25 mL) and filter. Concentrate the filtrate under reduced pressure to give an oil. Triturate with methanol (50 mL) and filter to give a solid. Purification by flash chromatography using 5% ethyl acetate/hexanes to 20% ethyl acetate/hexanes as gradient eluent yields the title compound (0.16 g, 60%): MS (m/z): 387.2 (M−1). ¹H NMR (CDCl₃) 12.91 (s, 1H), 8.34 (d, J=5.1 Hz, 1H), 7.65 (d, J=9.0 Hz, 1H), 7.50 (t, J=8.0 Hz, 1H), 7.36 (d, J=7.8 Hz, 1H), 7.31-7.24 (m, 2H), 7.21 (s, 1H), 7.15 (d, J=8.0 Hz, 1H), 6.51 (d, J=9.0 Hz, 1H), 5.23 (s, 2H), 3.00 (q, J=7.5 Hz, 2H), 2.19 (s, 3H), 1.26 (t, J=7.5 Hz, 3H).

Preparation 44

Synthesis of 3-[4-(4-acetyl-3-hydroxy-2-trifluoromethyl-phenoxymethyl)-phenoxy]-benzonitrile.

3-(4-Iodomethyl-phenoxy)-benzonitrile is prepared by an analogous procedure described in Preparation 43. Add half of a solution of 3-(4-iodomethyl-phenoxy)-benzonitrile (470 mg, 1.4 mmol) in anhydrous dimethylformamide (10 mL) to 1-(2,4-dihydroxy-3-trifluoromethyl-phenyl)-ethanone (300 mg, 1.4 mmol) and Li₂CO₃ (228 mg, 3.1 mmol) in anhydrous dimethylformamide (18 mL)dimethylformamide. Heat the reaction mixture to 60° C. and stir for 1 h. Add the other half of the 3-(4-iodomethyl-phenoxy)-benzonitrile solution to the reaction mixture. Stirred at 60° C. for an additional 1 h, cool to room temperature, and quench with water (75 mL). Extract the aqueous mixture with ethyl acetate (3×75 mL). Combine the organic layers, wash with brine, dry over sodium sulfate-sodium sulfate, and concentrate. Purify the residue by flash column chromatography using 50% ethyl acetate/hexane as the eluent to give the title compound (302 mg, 50%). LC-MS (m/e): 426 (M−1)

The following compounds are prepared essentially as described for Preparation 42, 43 or 44. The corresponding method is designated in the table below.

| Prep. No. | Method | Chemical name | Structure | Physical data |
|---|---|---|---|---|
| 45 | Method of Preparation 42 | 2-[4-(4-Acetyl-3-hydroxy-2-propyl-phenoxymethyl)-phenoxy]-benzonitrile | 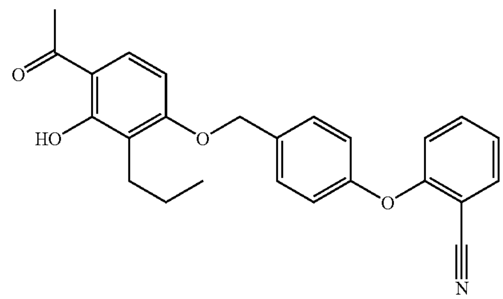 | MS (m/z): 400.2 (M − 1). ¹H NMR (CDCl₃) 12.79 (s, 1H), 7.71 (d, J = 8.0 Hz, 1H), 7.63 (d, J = 8.8 Hz, 1H), 7.53 (t, J = 8.0 Hz, 1H), 7.48 (d, J = 8.2 Hz, 2H), 7.19 (t, 7.6 Hz, 1H), 7.15 (d, J = 8.2 Hz, 2H), 6.95 (d, J = 8.5 Hz, 1H), 6.53 (d, J = 8.8 Hz, 1H), 5.19 (s, 2H), 2.74 (t, J = 7.5 Hz, 2H), 2.61 (s, 3H), 1.66-1.56 (m, 2H), 0.99 (t, J = 7.5 Hz, 3H). |
| 46 | Method of Preparation 42 | 6-[4-(4-Acetyl-3-hydroxy-2-propyl-phenoxymethyl)-phenoxy]-nicotinonitrile | 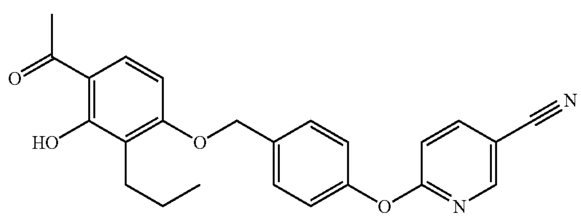 | MS (m/z): 401.2 (M − 1). ¹H NMR (CDCl₃) 12.79 (s, 1H), 8.51 (s, 1H), 7.97 (dd, J = 2.2 Hz, 8.8 Hz, 1H), 7.64 (d, J = 9.1 Hz, 1H), 7.53 (d, J = 8.4 Hz, 2H), 7.22 (d, J = 8.4 Hz, 2H), 7.09 (d, J = 8.8 Hz, 1H), 6.55 (d, J = 9.1 Hz, 1H), 5.22 (s, 2H), 2.74 (t, J = 7.4 Hz, 2H), 2.61 (s, 3H), 1.67-1.57 (m, 2H), 0.99 (t, J = 7.4 Hz, 3H). |
| 47 | Method of Preparation 42 | 2-[3-(4-Acetyl-3-hydroxy-2-propyl-phenoxymethyl)-phenoxy]-nicotinonitrile | 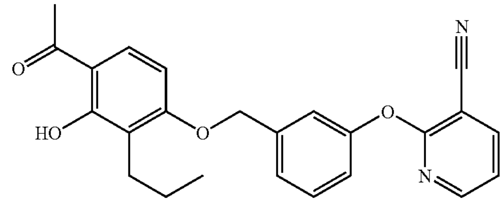 | MS (m/z): 401.2 (M − 1). ¹H NMR (CDCl₃) 12.78 (s, 1H), 8.35 (dd, J = 1.8 Hz, 5.1 Hz, 1H), 8.06 (dd, J = 1.8 Hz, 7.7 Hz, 1H), 7.62 (d, J = 9.0 Hz, 1H), 7.51 (t, J = 8.0 Hz, 1H), 7.36 (d, J = 7.7 Hz, 1H), 7.20 (d, J = 8.0 Hz, 1H), 7.16 (d, J = 5.1 Hz, 1H), 7.14 (d, J = 5.1 Hz, 1H), 6.51 (d, J = 9.0 Hz, 1H), 5.23 (s, 2H), 2.72 (t, J = 7.5 Hz, 2H), 2.60 (s, 3H), 1.63-1.53 (m, 2H), 0.94 (t, J = 7.3 Hz, 3H). |

-continued

| Prep. No. | Method | Chemical name | Structure | Physical data |
|---|---|---|---|---|
| 48 | Method of Preparation 42 | 2-[3-(4-Acetyl-3-hydroxy-2-propyl-phenoxymethyl)-phenoxy]-benzonitrile | 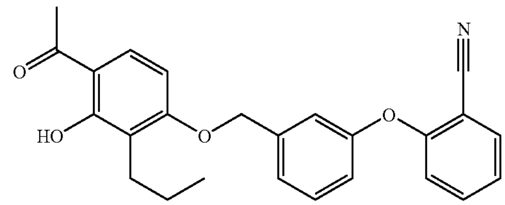 | MS (m/z): 400.2 (M − 1). $^1$H NMR (CDCl$_3$) 12.78 (s, 1H), 7.71 (dd, J = 1.5 Hz, 7.7 Hz, 1H), 7.61 (d, J = 9.1 Hz, 1H), 7.51 (t, J = 7.9 Hz, 1H), 7.46 (t, J = 7.7 Hz, 1H), 7.31-7.27 (m, 1H), 7.20 (t, J = 7.7 Hz, 1H), 7.16 (s, 1H), 7.09 (d, J = 7.9 Hz, 1H), 6.93 (d, J = 8.6 Hz, 1H), 6.49 (d, J = 9.1 Hz, 1H), 5.20 (s, 2H), 2.69 (t, J = 7.4 Hz, 2H), 2.60 (s, 3H), 1.62-1.52 (m, 2H), 0.93 (t, J = 7.4 Hz, 3H). |
| 49 | Method of Preparation 43 | 2-[3-(3-Hydroxy-2-methyl-4-propionyl-phenoxymethyl)-phenoxy]-isonicotinonitrile | 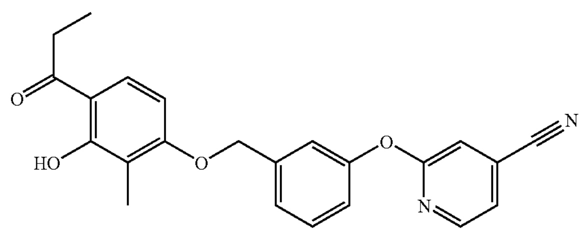 | MS (m/z): 387.2 (M − 1). $^1$H NMR (CDCl$_3$) 12.91 (s, 1H), 8.34 (d, J = 5.1 Hz, 1H), 7.65 (d, J = 9.0 Hz, 1H), 7.50 (t, J = 8.0 Hz, 1H), 7.36 (d, J = 7.8 Hz, 1H), 7.31-7.24 (m, 2H), 7.21 (s, 1H), 7.15 (d, J = 8.0 Hz, 1H), 6.51 (d, J = 9.0 Hz, 1H), 5.23 (s, 2H), 3.00 (q, J = 7.5 Hz, 2H), 2.19 (s, 3H), 1.26 (t, J = 7.5 Hz, 3H). |
| 50 | Method of Preparation 42 | 2-[4-(4-Acetyl-3-hydroxy-2-propyl-phenoxymethyl)-phenoxy]-isonicotinonitrile | 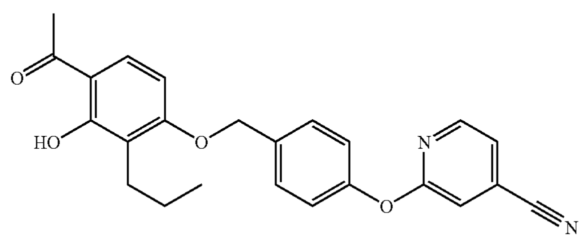 | MS (m/z): 401.1 (M − 1). $^1$H NMR (CDCl$_3$) 12.80 (s, 1H), 8.37 (d, J = 5.1 Hz, 1H), 7.64 (d, J = 9.2 Hz, 1H), 7.52 (d, J = 8.5 Hz, 2H), 7.25 (d, J = 5.1 Hz, 1H), 7.22 (d, J = 8.5 Hz, 2H), 6.54 (d, J = 9.2 Hz, 1H), 5.21 (s, 2H), 2.75 (t, J = 7.6 Hz, 2H), 2.61 (s, 3H), 1.67-1.57 (m, 2H), 0.99 (t, J = 7.4 Hz, 3H). |
| 51 | Method of Preparation 42 | 2-[4-(4-Acetyl-3-hydroxy-2-propyl-phenoxymethyl)-phenoxy]-nicotinonitrile | 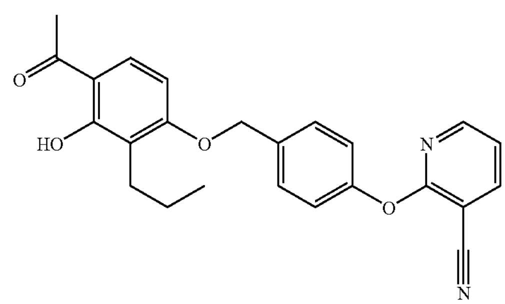 | MS (m/z): 401.2 (M − 1). $^1$H NMR (CDCl$_3$) 12.79 (s, 1H), 8.37 (dd, J = 2.1 Hz, 5.2 Hz, 1H), 8.06 (dd, J = 2.1 Hz, 7.7 Hz, 1H), 7.63 (d, J = 9.1 Hz, 1H), 7.53 (d, J = 8.4 Hz, 2H), 7.27 (d, J = 8.4 Hz, 2H), 7.15 (dd, J = 5.2 Hz, 7.7 Hz, 1H), 6.54 (d, J = 9.1 Hz, 1H), 5.22 (s, 2H), 2.75 (t, J = 7.6 Hz, 2H), 2.61 (s, 3H), 1.67-1.57 (m, 2H), 0.99 (t, J = 7.6 Hz, 3H). |
| 52 | Method of Preparation 43 | 2-[3-(4-Acetyl-3-hydroxy-2-propyl-phenoxymethyl)-phenoxy]-isonicotinonitrile | 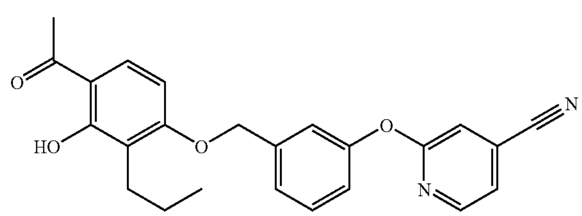 | MS (m/z): 401.1 (M − 1). $^1$H NMR (CDCl$_3$) 12.78 (s, 1H), 8.35 (d, J = 5.1 Hz, 1H), 7.61 (d, J = 9.0 Hz, 1H), 7.50 (t, J = 7.9 Hz, 1H), 7.34 (d, J = 7.6 Hz, 1H), 7.26-7.23 (m, 2H), 7.21 (s, 1H), 7.14 (d, J = 8.1 Hz, 1H), 6.50 (d, J = 9.1 Hz, 1H), 5.22 (s, 2H), 2.71 (t, J = 7.3 Hz, 2H), 2.59 (s, 3H), 1.63-1.53 (m, 2H), 0.93 (t, J = 7.3 Hz, 3H). |

-continued

| Prep. No. | Method | Chemical name | Structure | Physical data |
|---|---|---|---|---|
| 53 | Method of Preparation 43 | 4-[3-(3-Hydroxy-2-methyl-4-propionyl-phenoxymethyl)-phenoxy]-benzonitrile | 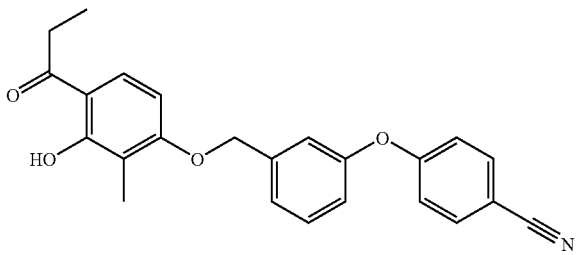 | $^1$H NMR (CDCl$_3$) 12.91 (s, 1H), 7.67-7.62 (m, 3H), 7.47 (t, J = 8.1 Hz, 1H), 7.32 (d, J = 7.8 Hz, 1H), 7.18 (s, 1H), 7.08-7.03 (m, 3H), 6.50 (d, J = 8.9 Hz, 1H), 5.19 (s, 2H), 3.00 (q, J = 7.2 Hz, 2H), 2.18 (s, 3H), 1.26 (t, J = 7.2 Hz, 3H). |
| 54 | Method of Preparation 43 | 4-[3-(4-Acetyl-3-hydroxy-2-propyl-phenoxymethyl)-phenoxy]-benzonitrile | 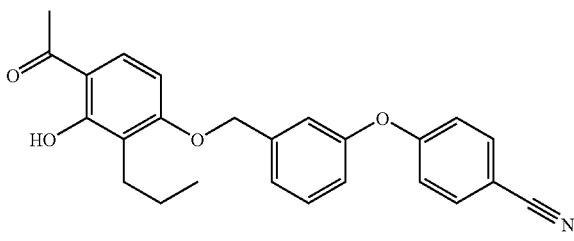 | $^1$H NMR (CDCl$_3$) 12.78 (s, 1H), 7.64 (d, J = 8.5 Hz, 2H), 7.62 (d, J = 9.1 Hz, 1H), 7.47 (t, J = 7.8 Hz, 1H), 7.32-7.27 (m, 2H), 7.17 (s, 1H), 7.06 (d, J = 8.5 Hz, 2H), 6.50 (d, J = 9.1 Hz, 1H), 5.19 (s, 2H), 2.70 (t, J = 7.5 Hz, 2H), 2.60 (s, 3H), 1.61-1.52 (m, 2H), 0.93 (t, J = 7.5 Hz, 3H). |
| 55 | Method of Preparation 43 | 3-[3-(3-Hydroxy-2-methyl-4-propionyl-phenoxymethyl)-phenoxy]-5-trifluoromethyl-benzonitrile | 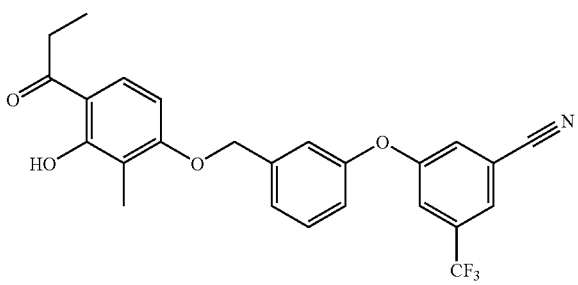 | MS (m/z): 454.1 (M − 1). $^1$H NMR (CDCl$_3$) 12.92 (s, 1H), 7.66 (d, J = 9.1 Hz, 1H), 7.64 (s, 1H), 7.54-7.49 (m, 2H), 7.40-7.35 (m, 2H), 7.16 (s, 1H), 7.06 (dd, J = 2.2 Hz, 8.2 Hz, 1H), 6.49 (d, J = 9.1 Hz, 1H), 5.23 (s, 2H), 3.01 (q, J = 7.2 Hz, 2H), 2.19 (s, 3H), 1.26 (t, J = 7.2 Hz, 3H). |
| 56 | Method of Preparation 43 | 3-[4-(3-Hydroxy-2-methyl-4-propionyl-phenoxymethyl)-phenoxy]-benzonitrile | 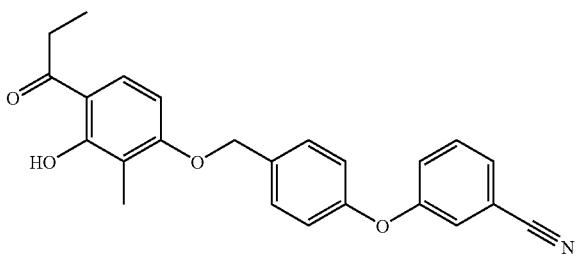 | MS (m/z): 386.1 (M − 1). $^1$H NMR (CDCl$_3$) 12.92 (s, 1H), 7.67 (d, J = 9.0 Hz, 1H), 7.51-7.40 (m, 4H), 7.31-7.26 (m, 2H), 7.09 (d, J = 8.5 Hz, 2H), 6.54 (d, J = 9.0 Hz, 1H), 5.19 (s, 2H), 3.01 (q, J = 7.2 Hz, 2H), 2.21 (s, 3H), 1.27 (t, J = 7.2 Hz, 3H). |
| 57 | Method of Preparation 43 | 6-[3-(3-Hydroxy-2-methyl-4-propionyl-phenoxymethyl)-phenoxy]-nicotinic acid methyl ester | 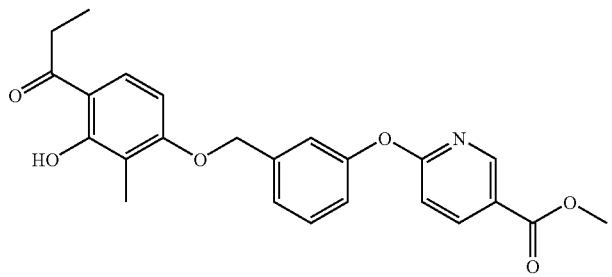 | MS (m/z): 420.1 (M − 1). $^1$H NMR (CDCl$_3$) 12.91 (s, 1H), 8.85 (s, 1H), 8.32 (dd, J = 2.1 Hz, 8.5 Hz, 1H), 7.65 (d, J = 8.8 Hz, 1H), 7.49 (t, J = 8.0 Hz, 1H), 7.34 (d, J = 7.7 Hz, 1H), 7.30-7.26 (m, 2H), 7.16 (d, J = 8.0 Hz, 1H), 7.00 (d, J = 8.8 Hz, 1H), 5.22 (s, 2H), 3.96 (s, 3H), 3.00 (q, J = 7.4 Hz, 2H), 2.19 (s, 3H), 1.26 (t, J = 7.4 Hz, 3H). |

| Prep. No. | Method | Chemical name | Structure | Physical data |
|---|---|---|---|---|
| 58 | Method of Preparation 43 | 6-[3-(3-Hydroxy-2-methyl-4-propionyl-phenoxymethyl)-phenoxy]-nicotinonitrile | 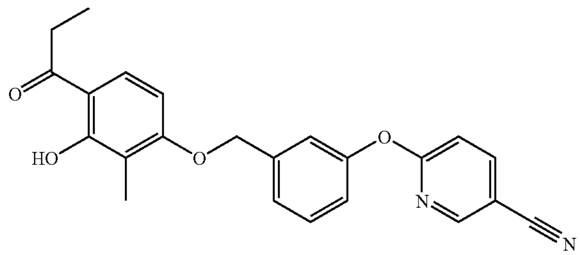 | MS (m/z): 387.1 (M − 1). $^1$H NMR (CDCl$_3$) 12.92 (s, 1H), 8.50 (d, J = 2.0 Hz, 1H), 7.97 (dd, J = 2.2 Hz, 8.8 Hz, 1H), 7.65 (d, J = 9.0 Hz, 1H), 7.51 (t, J = 7.8 Hz, 1H), 7.38 (d, J = 7.8 Hz, 1H), 7.30-7.26 (m, 2H), 7.16 (dd, J = 2.0 Hz, 7.8 Hz, 1H), 6.51 (d, J = 9.0 Hz, 1H), 5.23 (s, 2H), 3.01 (q, J = 7.2 Hz, 2H), 2.19 (s, 3H), 1.26 (t, J = 7.2 Hz, 3H). |
| 59 | Method of Preparation 43 | 6-[3-(4-Acetyl-2-fluoro-3-hydroxy-phenoxymethyl)-phenoxy]-nicotinonitrile | 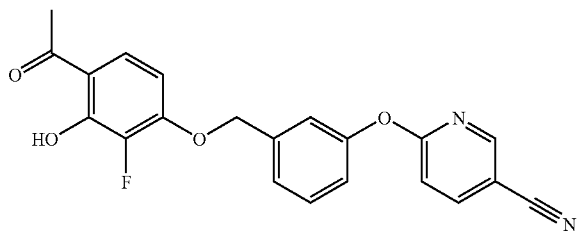 | MS (m/z): 377.0 (M − 1). $^1$H NMR (CDCl$_3$) 12.50 (s, 1H), 8.49 (s, 1H), 7.97 (dd, J = 2.0 Hz, 8.8 Hz, 1H), 7.54-7.48 (m, 2H), 7.38 (d, J = 7.8 Hz, 1H), 7.28 (s, 1H), 7.17 (d, J = 8.1 Hz, 1H), 7.09 (d, J = 8.8 Hz, 1H), 6.58 (dd, J = 7.1 Hz, 8.8 Hz, 1H), 5.30 (s, 2H), 2.62 (s, 3H). |
| 60 | Method of Preparation 43 | 6-[3-(4-Acetyl-2-chloro-3-hydroxy-phenoxymethyl)-phenoxy]-nicotinonitrile | 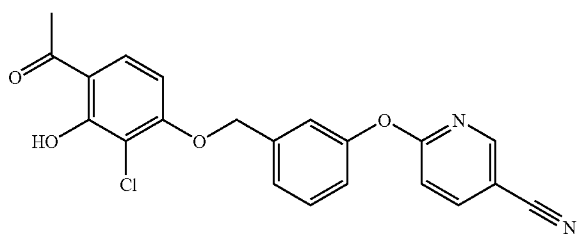 | MS (m/z): 393.0 (M − 1). $^1$H NMR (CDCl$_3$) 13.19 (s, 1H), 8.49 (s, 1H), 7.97 (dd, J = 2.1 Hz, 8.6 Hz, 1H), 7.68 (d, J = 9.1 Hz, 1H), 7.52 (t, J = 7.8 Hz, 1H), 7.40 (d, J = 7.8 Hz, 1H), 7.31 (s, 1H), 7.17 (d, J = 8.2 Hz, 1H), 7.09 (d, J = 8.6 Hz, 1H), 6.60 (d, J = 9.1 Hz, 1H), 5.31 (s, 2H), 2.63 (s, 3H). |
| 61 | Method of Preparation 43 | 6-[3-(4-Acetyl-3-hydroxy-2-methyl-phenoxymethyl)-phenoxy]-nicotinonitrile | 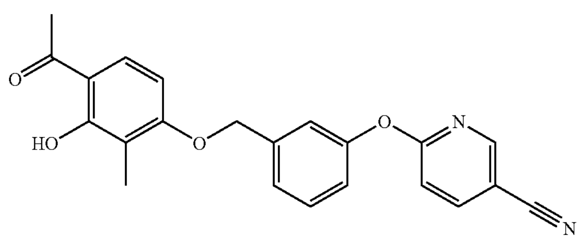 | MS (m/z): 373.0 (M − 1). $^1$H NMR (CDCl$_3$) 12.82 (s, 1H), 8.50 (d, J = 2.1 Hz, 1H), 7.97 (dd, J = 2.4 Hz, 8.8 Hz, 1H), 7.62 (d, J = 9.0 Hz, 1H), 7.51 (t, J = 8.1 Hz, 1H), 7.38 (d, J = 7.9 Hz, 1H), 7.27 (s, 1H), 7.16 (d, J = 7.9 Hz, 1H), 7.09 (d, J = 8.8 Hz, 1H), 6.52 (d, J = 9.0 Hz, 1H), 5.23 (s, 2H), 2.61 (s, 3H), 2.19 (s, 3H). |
| 62 | Method of Preparation 43 | 2-[3-(4-Acetyl-2-chloro-3-hydroxy-phenoxymethyl)-phenoxy]-isonicotinonitrile | 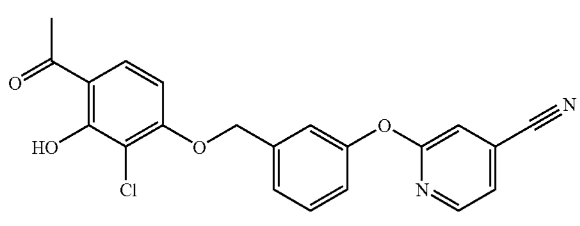 | MS (m/z): 393.0 (M − 1). $^1$H NMR (CDCl$_3$) 13.19 (s, 1H), 8.35 (d, J = 5.2 Hz, 1H), 7.68 (d, J = 9.0 Hz, 1H), 7.51 (t, J = 7.9 Hz, 1H), 7.38 (d, J = 7.7 Hz, 1H), 7.31-7.28 (m, 1H), 7.25 (d, J = 5.2 Hz, 1H), 7.21 (s, 1H), 7.16 (d, J = 7.9 Hz, 1H), 6.59 (d, J = 9.0 Hz, 1H), 5.32 (s, 2H), 2.63 (s, 3H). |

| Prep. No. | Method | Chemical name | Structure | Physical data |
|---|---|---|---|---|
| 63 | Method of Preparation 43 | 2-[4-(4-Acetyl-3-hydroxy-2-methyl-phenoxymethyl)-phenoxy]-isonicotinonitrile | 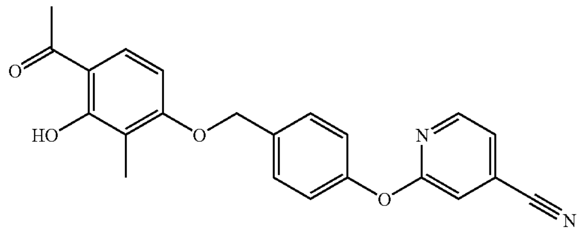 | $^1$H NMR (CDCl$_3$) 12.82 (s, 1H), 8.37 (d, J = 4.9 Hz, 1H), 7.64 (d, J = 9.0 Hz, 1H), 7.54 (d, J = 8.2 Hz, 2H), 7.26-7.19 (m, 4H), 6.55 (d, J = 9.0 Hz, 1H), 5.22 (s, 2H), 2.62 (s, 3H), 2.21 (s, 3H). |
| 64 | Method of Preparation 43 | 3-[4-(4-Acetyl-3-hydroxy-2-methyl-phenoxymethyl)-phenoxy]-benzonitrile | 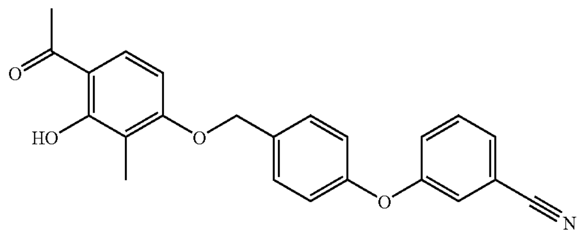 | $^1$H NMR (CDCl$_3$) 12.82 (s, 1H), 7.64 (d, J = 9.0 Hz, 1H), 7.49 (d, J = 8.6 Hz, 2H), 7.47 (t, J = 8.0 Hz, 1H), 7.42 (d, J = 7.6 Hz, 1H), 7.32-7.25 (m, 2H), 7.09 (d, J = 8.6 Hz, 2H), 6.55 (d, J = 9.0 Hz, 1H), 5.20 (s, 2H), 2.61 (s, 3H), 2.21 (s, 3H). |
| 65 | Method of Preparation 43 | 3-[4-(4-Acetyl-3-hydroxy-phenoxymethyl)-phenoxy]-benzonitrile | 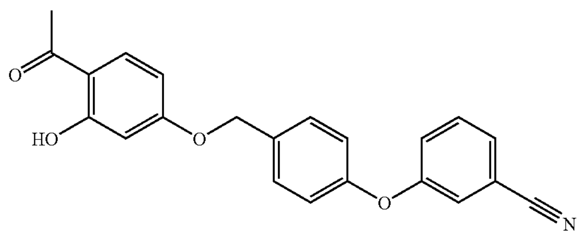 | $^1$H NMR (CDCl$_3$) 12.79 (s, 1H), 7.69 (d, J = 8.6 Hz, 1H), 7.51-7.40 (m, 4H), 7.30-7.26 (m, 2H), 7.09 (d, J = 8.6 Hz, 2H), 6.58-6.53 (m, 2H), 5.12 (s, 2H), 2.60 (s, 3H). |
| 66 | Method of Preparation 43 | 3-[5-(4-Acetyl-3-hydroxy-2-propyl-phenoxymethyl)-pyridin-2-yloxy]-benzonitrile | 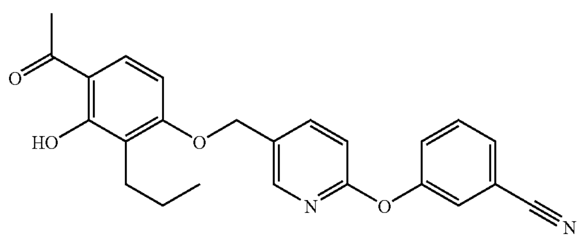 | $^1$H NMR (CDCl$_3$) 12.79 (s, 1H), 8.25 (s, 1H), 7.86 (dd, J = 2.2 Hz, 8.2 Hz, 1H), 7.64 (d, J = 9.1 Hz, 1H), 7.55-7.43 (m, 4H), 7.08 (d, J = 8.2 Hz, 1H), 6.54 (d, J = 9.1 Hz, 1H), 5.15 (s, 2H), 2.69 (t, J = 7.2 Hz, 2H), 2.59 (s, 3H), 1.62-1.52 (m, 2H), 0.95 (t, J = 7.2 Hz, 3H). |
| 67 | Method of Preparation 43 | 3-[5-(3-Hydroxy-2-methyl-4-propionyl-phenoxymethyl)-pyridin-2-yloxy]-benzonitrile | 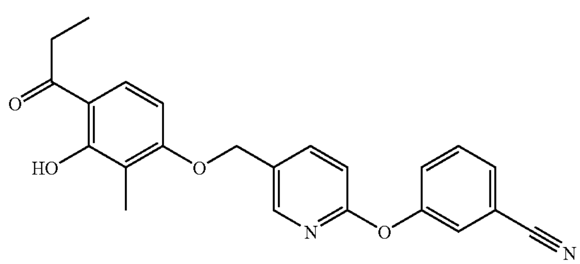 | $^1$H NMR (CDCl$_3$) 12.91 (s, 1H), 8.26 (s, 1H), 7.86 (dd, J = 2.2 Hz, 8.4 Hz, 1H), 7.66 (d, J = 9.0 Hz, 1H), 7.54-7.42 (m, 4H), 7.07 (d, J = 8.4 Hz, 1H), 6.53 (d, J = 9.0 Hz, 1H), 5.14 (s, 2H), 2.99 (q, J = 7.2 Hz, 2H), 2.14 (s, 3H), 1.25 (t, J = 7.2 Hz, 3H). |
| 68 | Method of Preparation 44 | 2-[3-(4-Acetyl-3-hydroxy-2-trifluoromethyl-phenoxymethyl)-phenoxy]-isonicotinonitrile | 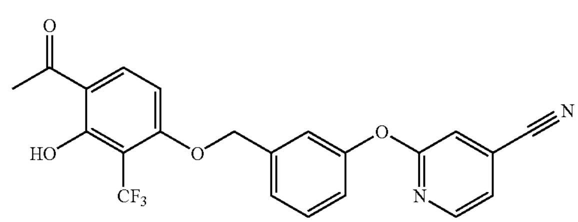 | LC-MS (m/e): 427 (M − 1); $^1$H NMR (CDCl$_3$) δ 13.65 (1H, s), 8.36 (1H, d), 7.89 (1H, d), 7.50 (1H, dd), 7.10-7.40 (5H, m), 6.59 (d, 1H), 5.30 (2H, s), 2.62 (3H, s). |

-continued

| Prep. No. | Method | Chemical name | Physical data |
|---|---|---|---|
| 69 | Method of Preparation 44 | 6-[3-(4-Acetyl-3-hydroxy-2-trifluoromethyl-phenoxymethyl)-phenoxy]-nicotinonitrile | LC-MS (m/e): 427 (M − 1); $^1$H NMR (CDCl$_3$) δ 13.70 (1H, s), 8.54 (1H, dd), 8.02 (1H, dd), 7.94 (1H, d), 7.56 (1H, dd), 7.41 (1H, d), 7.32 (1H, s), 7.21 (1H, d), 7.15 (1H, d), 6.55 (1H, d), 5.35 (2H, s), 2.69 (3H, s). |
| 70 | Method of Preparation 44 | 6-[3-(4-Acetyl-3-hydroxy-2-trifluoromethyl-phenoxymethyl)-phenoxy]-nicotinic acid methyl ester | LC-MS (m/e): 460 (M − 1) |
| 71 | Method of Preparation 42 | 3-[2-(4-Acetyl-3-hydroxy-2-propyl-phenoxymethyl)-phenylsulfanyl]-benzonitrile | MS (m/z): 416 (M − 1). |
| 72 | Method of Preparation 42 | 4-[3-(4-Acetyl-3-hydroxy-2-propyl-phenoxymethyl)-phenylsulfanyl]-benzonitrile | MS (m/z): 416 (M − 1). |
| 73 | Method of Preparation 42 | 4-[2-(4-Acetyl-3-hydroxy-2-propyl-phenoxymethyl)-phenylsulfanyl]-benzonitrile | MS (m/z): 416 (M − 1). |

-continued

| Prep. No. | Method | Chemical name | Structure | Physical data |
|---|---|---|---|---|
| 74 | Method of Preparation 42 | 2-[4-(4-Acetyl-3-hydroxy-2-propyl-phenoxymethyl)-phenylsulfanyl]-benzonitrile | 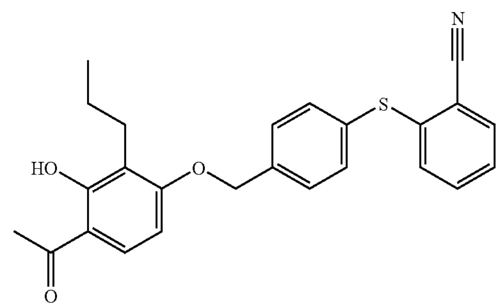 | MS (m/z): 416 (M − 1). |
| 75 | Method of Preparation 42 | 2-[3-(4-Acetyl-3-hydroxy-2-propyl-phenoxymethyl)-phenylsulfanyl]-benzonitrile | 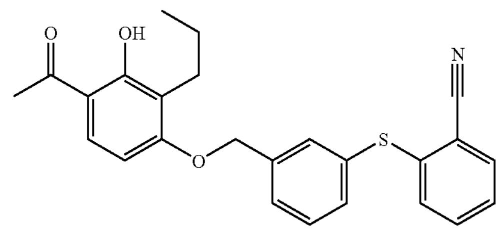 | MS (m/z): 416 (M − 1). |
| 76 | Method of Preparation 42 | 4-[4-(4-Acetyl-3-hydroxy-2-propyl-phenoxymethyl)-phenylsulfanyl]-benzonitrile | 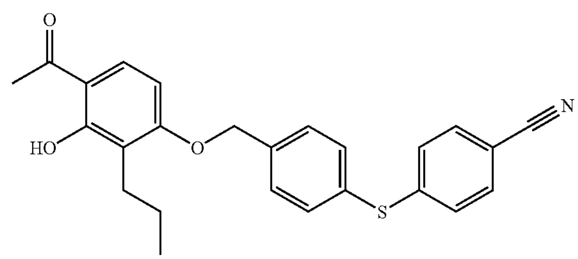 | MS (m/z): 416 (M − 1). |
| 77 | Method of Preparation 42 | 3-[4-(4-Acetyl-3-hydroxy-2-propyl-phenoxymethyl)-phenylsulfanyl]-benzonitrile | 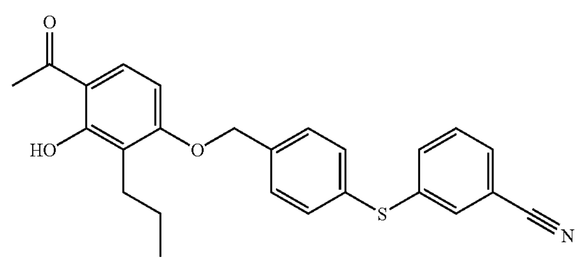 | MS (m/z): 416 (M − 1). |
| 78 | Method of Preparation 42 | 2-[3-(4-Acetyl-3-hydroxy-2-propyl-phenoxymethyl)-benzenesulfonyl]-benzonitrile | 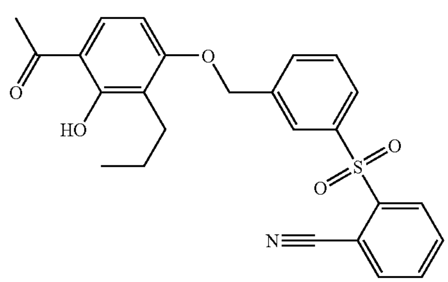 | MS (m/z): 448 (M − 1). |

-continued

| Prep. No. | Method | Chemical name | Structure | Physical data |
|---|---|---|---|---|
| 79 | Method of Preparation 42 | 3-[3-(4-Acetyl-3-hydroxy-2-propyl-phenoxymethyl)-benzenesulfonyl]-benzonitrile | 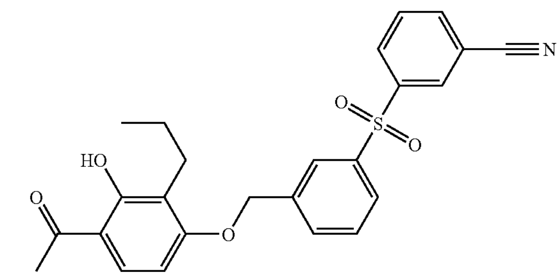 | MS (m/z): 448 (M − 1). |
| 80 | Method of Preparation 42 | 4-[4-(4-Acetyl-3-hydroxy-2-propyl-phenoxymethyl)-benzenesulfonyl]-benzonitrile | 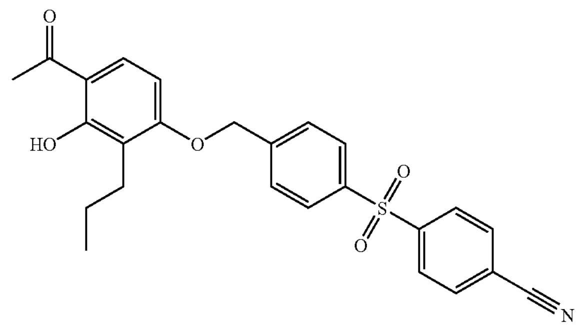 | MS (m/z): 448 (M − 1). |
| 81 | Method of Preparation 42 | 3-[4-(4-Acetyl-3-hydroxy-2-propyl-phenoxymethyl)-benzenesulfonyl]-benzonitrile | 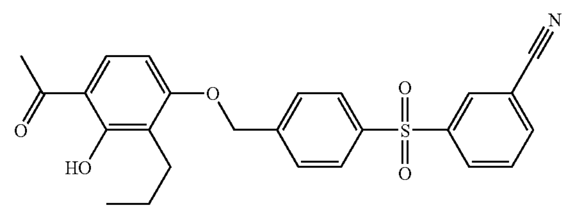 | MS (m/z): 448 (M − 1). |
| 82 | Method of Preparation 42 | 4-[3-(4-Acetyl-3-hydroxy-2-propyl-phenoxymethyl)-benzenesulfonyl]-benzonitrile | 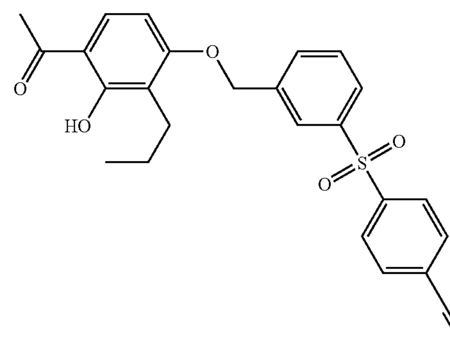 | MS (m/z): 448 (M − 1). |
| 83 | Method of Preparation 42 | 3-[2-(4-Acetyl-3-hydroxy-2-propyl-phenoxymethyl)-benzenesulfinyl]-benzonitrile | 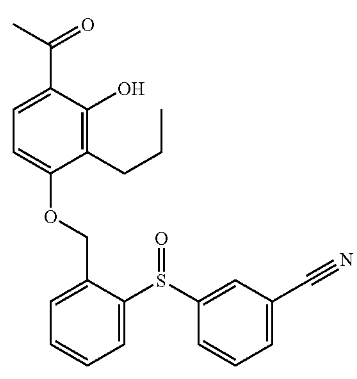 | MS (m/z): 432 (M − 1). |

-continued

| Prep. No. | Method | Chemical name | Structure | Physical data |
|---|---|---|---|---|
| 84 | Method of Preparation 42 | 2-[3-(4-Acetyl-3-hydroxy-2-propyl-phenoxymethyl)-benzenesulfinyl]-benzonitrile | 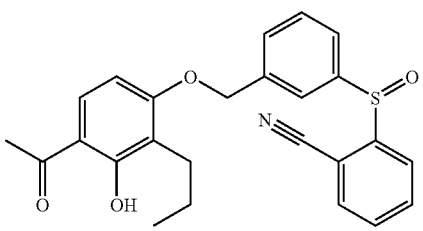 | MS (m/z): 432 (M − 1). |
| 85 | Method of Preparation 42 | 4-[4-(4-Acetyl-3-hydroxy-2-propyl-phenoxymethyl)-benzenesulfinyl]-benzonitrile | 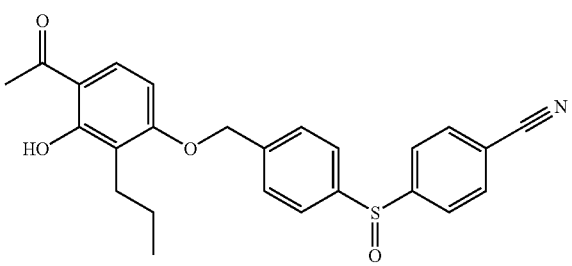 | MS (m/z): 432 (M − 1). |
| 86 | Method of Preparation 42 | 3-[4-(4-Acetyl-3-hydroxy-2-propyl-phenoxymethyl)-benzenesulfinyl]-benzonitrile | 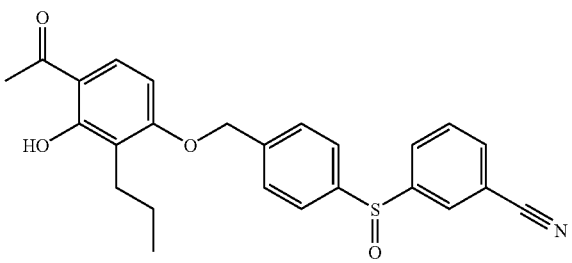 | MS (m/z): 432 (M − 1). |
| 87 | Method of Preparation 42 | 3-[3-(4-Acetyl-3-hydroxy-2-propyl-phenoxymethyl)-benzenesulfinyl]-benzonitrile | 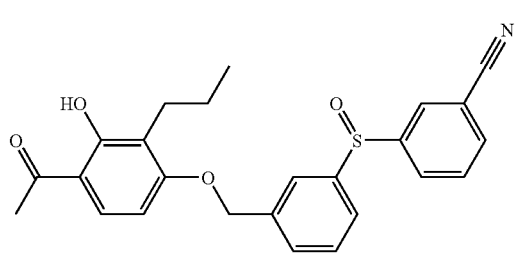 | MS (m/z): 432 (M − 1). |
| 88 | Method of Preparation 42 | 3-[3-(4-Acetyl-3-hydroxy-2-propyl-phenoxymethyl)-benzenesulfonyl]-benzoic acid ethyl ester | 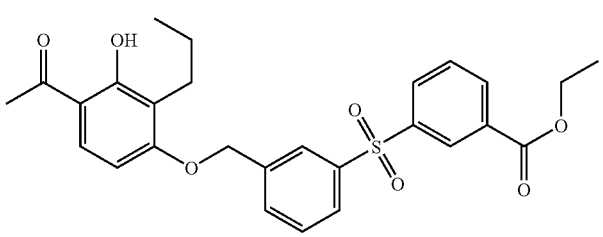 | MS (m/z): 495 (M − 1). |

| Prep. No. | Method | Chemical name | Structure | Physical data |
|---|---|---|---|---|
| 89 | Method of Preparation 42 | 3-[4-(4-Acetyl-3-hydroxy-2-propyl-phenoxymethyl)-benzenesulfonyl]-benzoic acid ethyl ester | 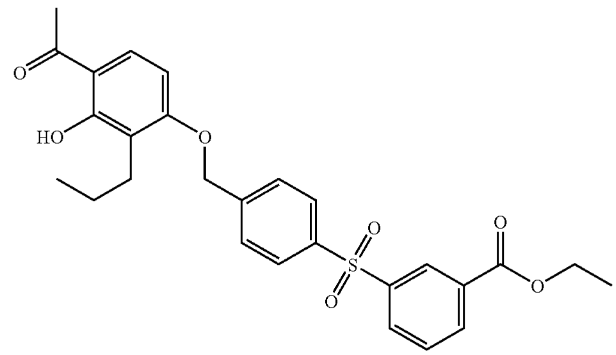 | MS (m/z): 495 (M − 1). |
| 90 | Method of Preparation 42 | 4-[4-(4-Acetyl-3-hydroxy-2-propyl-phenoxymethyl)-benzenesulfonyl]-benzoic acid methyl ester | 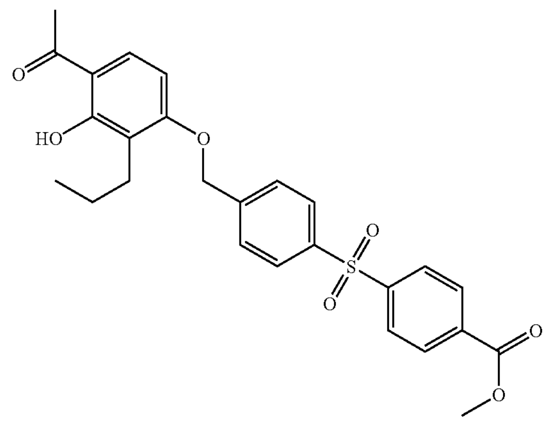 | MS (m/z): 481 (M − 1). |

Preparation 91

Synthesis of 3-(4-cyano-pyridin-2-ylsulfanyl)-benzoic acid

Add sodium hydride (60% dispersion in mineral oil, 635 mg, 15.88 mmol) to a solution of 3-mercapto-benzoic acid (1.11 g, 7.22 mmol) in dimethylformamide (50 mL) chilled to 0° C. and stir. After 10 minutes add 2-chloro-isonicotinonitrile (1.00 g, 7.22 mmol). Warm gradually to ambient temperature. After 18 hours, add 1N aqueous hydrochloric acid (200 mL). Filter the resulting precipitate, washing with water and hexanes to yield the title compound as a tan solid (920 mg, 50%): $^1$H NMR (DMSO-$d_6$) δ 7.62-7.66 (m, 3H), 7.84 (d, 1H), 8.03-8.08 (m, 2H), 8.62 (d, 1H), 13.26 (bs, 1H).

Preparation 92

Synthesis of 3-(5-cyano-pyridin-2-ylsulfanyl)-benzoic acid

Add sodium hydride (60% dispersion in mineral oil, 635 mg, 15.88 mmol) to a solution of 3-mercapto-benzoic acid (1.11 g, 7.22 mmol) in dimethylformamide (50 mL) chilled to 0° C. and stir. After 10 minutes add 6-chloro-nicotinonitrile (1.00 g, 7.22 mmol). Warm gradually to ambient temperature. After 18 hours, add 1N aqueous hydrochloric acid (200 mL). Filter resulting precipitate, washing with water and hexanes to yield the title compound as a tan solid (1.25 g, 68%): $^1$H NMR (DMSO-$d_6$) δ 7.22 (d, 1H), 7.67 (t, 1H), 7.88 (dt, 1H), 8.07-8.12 (m, 3H), 8.82 (dd, 1H), 13.30 (bs, 1H).

Preparation 93

Synthesis of 2-(3-hydroxymethyl-phenylsulfanyl)-nicotinonitrile

Dissolve 3-(3-cyano-pyridin-2-ylsulfanyl)-benzoic acid (1.50 g, 5.85 mmol) in thionyl chloride (50 mL) and stir. Heat to reflux. After 2 hours, concentrate under reduced pressure to give a residue. Dissolve residue in dioxane (100 μL) and add sodium borohydride (2.21 g, 58.5 mmol). Heat to 50° C. After 2 hours, cool to ambient temperature and add water. Extract with ethyl acetate, combine organic layers, dry with sodium sulfate, filter and concentrate to give the title compound as a yellow oil (1.20 g, 85%): $^1$H NMR (DMSO-$d_6$) δ 4.54 (d, 2H), 5.30 (t, 1H), 7.37 (dd, 1H), 7.43 (m, 3H), 7.50 (m, 1H), 8.29 (dd, 1H), 8.56 (dd, 1H).

Preparation 94

Synthesis of 2-(3-hydroxymethyl-phenylsulfanyl)-isonicotinonitrile

Dissolve 3-(4-cyano-pyridin-2-ylsulfanyl)-benzoic acid (920 mg, 3.59 mmol) in thionyl chloride (50 mL) and stir. Heat to reflux. After 2 hours, concentrate under reduced pressure to give a residue. Dissolve residue in dioxane (100 mL) and add sodium borohydride (1.36 g, 35.9 mmol). Heat to 50°

C. After 2 hours, cool to ambient temperature and add water. Extract with ethyl acetate, combine organic layers, dry with sodium sulfate, filter and concentrate to give the title compound as a yellow oil (378 mg, 44%): $^1$H NMR (DMSO-d$_6$) δ 4.56 (d, 2H), 5.31 (t, 1H), 7.38 (m, 1H), 7.48 (m, 3H), 7.55 (m, 1H), 7.59 (dd, 1H), 8.62 (dd, 1H).

Preparation 95

Synthesis of 6-(3-hydroxymethyl-phenylsulfanyl)-nicotinonitrile

Dissolve 3-(5-cyano-pyridin-2-ylsulfanyl)-benzoic acid (1.25 g, 4.88 mmol) in thionyl chloride (50 mL) and stir. Heat to reflux. After 2 hours, concentrate under reduced pressure to give a residue. Dissolve residue in dioxane (100 mL) and add sodium borohydride (1.85 g, 48.8 mmol). Heat to 50° C. After 2 hours, cool to ambient temperature and add water. Extract with ethyl acetate, combine organic layers, dry with sodium sulfate, filter and concentrate to give the title compound as a yellow oil (670 mg, 57%): $^1$H NMR (DMSO-d$_6$) δ 4.56 (d, 2H), 5.33 (t, 1H), 7.06 (d, 1H), 7.49 (m, 3H), 7.57 (m, 1H), 8.08 (dd, 1H), 8.82 (dd, 1H).

Preparation 96

Synthesis of 2-[3-(4-acetyl-3-hydroxy-2-propyl-phenoxymethyl)-phenylsulfanyl]-nicotinonitrile The title compound is prepared essentially as described in Preparation 42 employing 2-(3-hydroxymethyl-phenylsulfanyl)-nicotinonitrile (920 mg, 3.79 mmol). The title compound is isolated as a white solid (1.50 g, 94%): $^1$H NMR (DMSO-d$_6$) δ 0.81 (t, 3H), 1.45 (sextet, 2H), 2.56 (t, 2H), 2.58 (s, 3H), 5.30 (s, 2H), 6.72 (d, 1H), 7.38 (dd, 1H), 7.54 (m, 3H), 7.64 (m, 1H), 7.82 (d, 1H), 8.30 (dd, 1H), 8.55 (dd, 1H), 12.84 (s, 1H).

Preparation 97

Synthesis of 2-[3-(4-acetyl-3-hydroxy-2-propyl-phenoxymethyl)-phenylsulfanyl]-isonicotinonitrile The title compound is prepared essentially as described in Preparation 42 employing 2-(3-hydroxymethyl-phenylsulfanyl)-isonicotinonitrile (378 mg, 1.56 mmol). The title compound is isolated as a white solid (380 mg, 58%): $^1$H NMR (DMSO-d$_6$) δ 0.80 (t, 3H), 1.44 (sextet, 2H), 2.57 (m, 5H), 5.32 (s, 2H), 6.72 (d, 1H), 7.41 (s, 1H), 7.56-7.63 (m, 4H), 7.68 (s, 1H), 7.82 (d, 1H), 8.63 (d, 1H), 12.84 (s, 1H).

Preparation 98

Synthesis of 6-[3-(4-acetyl-3-hydroxy-2-propyl-phenoxymethyl)-phenylsulfanyl]-nicotinonitrile The title compound is prepared essentially as described in Preparation 42 employing 6-(3-hydroxymethyl-phenylsulfanyl)-nicotinonitrile (650 mg, 2.68 mmol). The title compound is isolated as a white solid (430 mg, 38%): $^1$H NMR (DMSO-d$_6$) δ 0.81 (t, 3H), 1.44 (sextet, 2H), 2.57 (d, 2H), 2.58 (s, 3H), 5.33 (s, 2H), 6.73 (d, 1H), 7.10 (d, 1H), 7.60 (m, 3H), 7.70 (m, 1H), 7.82 (d, 1H), 8.08 (dd, 1H), 8.81 (dd, 1H), 12.84 (bs, 1H).

Preparation 99

Synthesis of 3-[3-(4-acetyl-3-hydroxy-2-propyl-phenoxymethyl)-phenylsulfanyl]-benzonitrile Add methanesulfonyl chloride (0.119 g, 1.04 mmol) to a solution of 3-(3-hydroxymethyl-phenylsulfanyl)-benzonitrile (0.250 g, 1.04 mmol) and triethylamine (0.210 g, 2.07 mmol) in dichloromethane (0.2 M). Stir for 1 h. Evaporate solvent. Dissolve the residue in N,N-dimethylformamide and add 1-(2,4-dihydroxy-3-propyl-phenyl)-ethanone (0.201 g, 1.04 mmol). Add cesium carbonate (0.673 g, 2.07 mmol) and stir for 1 h at 60° C. Dilute the reaction mixture with diethyl ether and wash with water (3×). Purify the residue by flash chromatography, eluting with hexanes, ramping to 50% ethyl acetate/hexanes to elute the title compound (0.331 mg, 0.790 mmol, 76%): MS (m/z): 416 (M−1).

EXAMPLE 1

Synthesis of 1-(4-acetyl-2-hydroxy-3-propyl-4-{4-[3-(1H-tetrazol-5-yl)-pyridin-2-yloxy]-benzyloxy}-phenyl)-ethanone

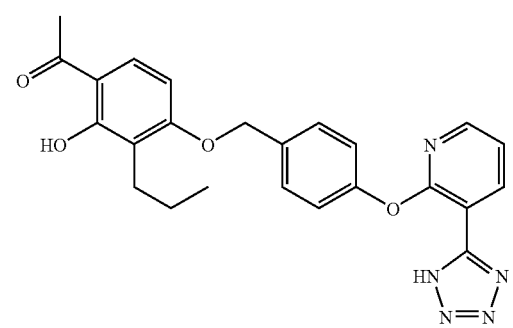

Mix 2-[4-(4-acetyl-3-hydroxy-2-propyl-phenoxymethyl)-phenoxy]-nicotinonitrile (0.16 g, 0.40 mmol), triethylamine hydrochloride (1.11 g, 8.05 mmol), sodium azide (0.52 g, 8.05 mmol) and toluene (6 mL) in a pressure vessel. Seal and heat to 130° C. for 6 hrs. Concentrate under reduced pressure to give a residue. Dilute with ethyl acetate (25 mL) and wash with 1N hydrochloric acid (3×50 mL). Dry over magnesium sulfate, filter, and concentrate to give a residue. Purification by flash chromatography, using 40:1 Chydrochloric acid$_3$/methanol+1% acetic acid to 20:1 chloroformchloroform/methanol+1% acetic acid as a gradient eluent gives the title compound (0.07 g, 40%): MS (m/z): 444.1 (M−1). $^1$H NMR (DMSO-d$_6$) 12.88 (s, 1H), 8.57 (d, J=7.4 Hz, 1H), 8.32 (d, J=5.0 Hz, 1H), 7.84 (d, J=9.2 Hz, 1H), 7.54 (d, J=8.2 Hz, 2H), 7.38 (dd, J=5.0 Hz, 7.4 Hz, 1H), 7.29 (d, J=8.2 Hz, 2H), 6.79 (d, J=9.2 Hz, 1H), 5.31 (s, 2H), 2.62 (t, J=7.4 Hz, 2H), 2.60 (s, 3H), 1.57-1.47 (m, 2H), 0.90 (t, J=7.4 Hz, 3H).

EXAMPLE 2

Synthesis of 1-(2-hydroxy-3-propyl-4-{3-[3-(2H-tetrazol-5-yl)-pyridin-2-ylsulfanyl]-benzyloxy}-phenyl)-ethanone

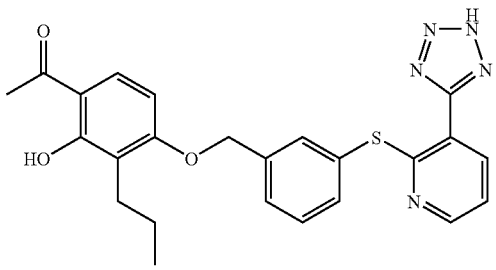

Using the procedure essentially as described for Example 1 using 2-[3-(4-acetyl-3-hydroxy-2-propyl-phenoxymethyl)-phenylsulfanyl]-nicotinonitrile (350 mg, 0.836 mmol), sodium azide (544 mg, 8.36 mmol), and triethylamine hydrochloride (1.15 g, 8.36 mmol) to yield the title compound as a tan solid (185 mg, 48%): $^1$H NMR (DMSO-d$_6$) δ 0.796 (t, 3H), 1.45 (sextuplet, 2H), 2.56 (t, 2H), 2.58 (s, 3H), 5.29 (s, 2H), 6.73 (d, 1H), 7.38 (dd, 1H), 7.48 (m, 3H), 7.57 (s, 1H), 7.82 (d, 1H), 8.16 (d, 1H), 8.44 (dd, 1H), 12.84 (s, 1H); MS (esi negative) m/z 460 (m$^{-1}$).

EXAMPLE 3

Synthesis of 1-(2-hydroxy-3-propyl-4-{3-[5-(1H-tetrazol-5-yl)-pyridin-2-yloxy]-benzyloxy}-phenyl)-ethanone

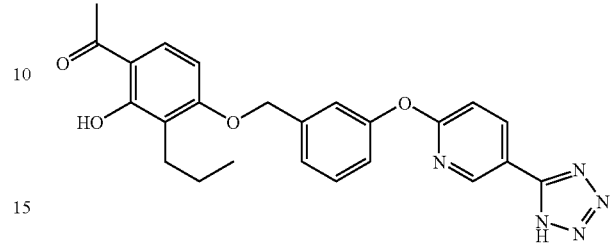

Mix 6-[3-(4-acetyl-3-hydroxy-2-propyl-phenoxymethyl)-phenoxy]-nicotinonitrile of Preparation 42, (0.33 g, 0.83 mmol), isopropyl alcohol (5 mL), zinc bromide (1.12 g, 4.98 mmol), sodium azide (0.32 g, 4.98 mmol) and water (5 mL) in a pressure flask. Seal the flask and heat to 130° C. in an oil bath for 6 hr. Allow to cool to ambient temperature and pour into 1N hydrochloric acid (50 mL). Filter the white solid and purify by flash chromatography, using 40:1 chloroformchloroform/methanol+1% acetic acid to 20:1 chloroformchloroform/methanol+1% acetic acid as a gradient eluent to give the title compound (0.25 g, 68%): MS (m/z): 444.2 (M−1). $^1$H NMR (DMSO-d$_6$) 12.86 (s, 1H), 8.80 (s, 1H), 8.46 (d, J=8.2 Hz, 1H), 7.84 (d, J=8.8 Hz, 1H), 7.52 (t, J=8.2 Hz, 1H), 7.37-7.28 (m, 3H), 7.20 (d, J=8.2 Hz, 1H), 6.75 (d, J=8.8 Hz, 1H), 5.32 (s, 2H), 2.63-2.55 (m, 5H), 1.51-1.41 (m, 2H), 0.82 (t, J=7.2 Hz, 3H).

The following compounds are prepared essentially as described in Example 1, 2 or Example 3 as designated in the table below.

| Ex. # | Method # | Chemical name | Structure | Physical data |
|---|---|---|---|---|
| 4 | Method of Example 3 | 1-(2-Hydroxy-3-propyl-4-{4-[2-(1H-tetrazol-5-yl)-phenoxy]-benzyloxy}-phenyl)-ethanone | 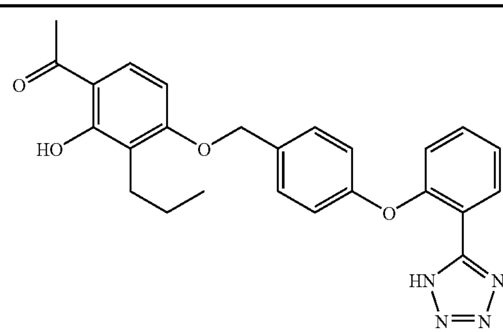 | MS (m/z): 443.2 (M − 1). $^1$H NMR (DMSO-d$_6$) 12.87 (s, 1H), 8.11 (d, J = 7.7 Hz, 1H), 7.84 (d, J = 9.0 Hz, 1H), 7.58 (t, J = 7.7 Hz, 1H), 7.51 (d, J = 8.2 Hz, 2H), 7.36 (t, J = 7.5 Hz, 1H), 7.15 (d, J = 8.0 Hz, 2H), 7.01 (d, J = 8.2 Hz, 1H), 6.77 (d, J = 9.0 Hz, 1H), 5.26 (s, 2H), 2.63-2.57 (m, 5H), 1.54-1.45 (m, 2H), 0.88 (t, J = 7.6 Hz, 3H). |
| 5 | Method of Example 3 | 1-(2-Hydroxy-3-propyl-4-{4-[5-(1H-tetrazol-5-yl)-pyridin-2-yloxy]-benzyloxy}-phenyl)-ethanone | 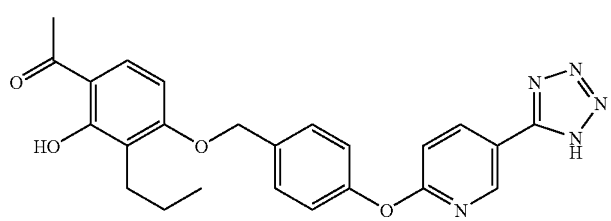 | MS (m/z): 444.2 (M − 1). $^1$H NMR (DMSO-d$_6$) 12.88 (s, 1H), 8.80 (s, 1H), 8.45 (d, J = 8.7 Hz, 1H), 7.85 (d, J = 9.1 Hz, 1H), 7.55 (d, J = 8.7 Hz, 2H), 7.31 (d, J = 8.6 Hz, 1H), 7.27 (d, J = 8.6 Hz, 2H), 6.80 (d, J = 9.1 Hz, 1H), 5.31 (s, 2H), 2.63 (t, J = 7.3 Hz, 2H), 2.61 (s, 3H), 1.57-1.47 (m, 2H), 0.91 (t, J = 7.3 Hz, 3H). |

| Ex. # | Method # | Chemical name | Structure | Physical data |
|---|---|---|---|---|
| 6 | Method of Example 3 | 1-(2-Hydroxy-3-propyl-4-{3-[3-(1H-tetrazol-5-yl)-pyridin-2-yloxy]-benzyloxy}-phenyl)-ethanone | 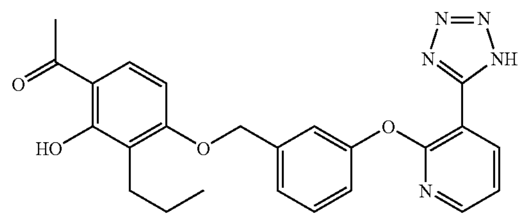 | MS (m/z): 444.2 (M − 1). $^1$H NMR (DMSO-$d_6$) 12.86 (s, 1H), 8.57 (d, J = 7.0 Hz, 1H), 8.33 (d, J = 4.4 Hz, 1H), 7.83 (d, J = 8.8 Hz, 1H), 7.52 (t, J = 7.0 Hz, 1H), 7.41-7.22 (m, 4H), 6.75 (d, J = 8.8 Hz, 1H), 5.31 (s, 2H), 2.61-2.55 (m, 5H), 1.51-1.41 (m, 2H), 0.81 (t, J = 7.3 Hz, 3H). |
| 7 | Method of Example 3 | 1-(2-Hydroxy-3-propyl-4-{3-[2-(1H-tetrazol-5-yl)-phenoxy]-benzyloxy}-phenyl)-ethanone | 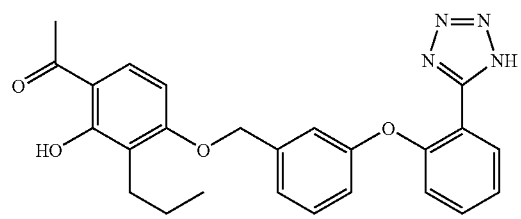 | MS (m/z): 443.2 (M − 1). $^1$H NMR (DMSO-$d_6$) 12.87 (s, 1H), 8.12 (d, J = 7.7 Hz, 1H), 7.81 (d, J = 9.2 Hz, 1H), 7.57 (t, J = 7.7 Hz, 1H), 7.49 (t, J = 7.7 Hz, 1H), 7.37 (t, J = 7.7 Hz, 1H), 7.29 (d, J = 7.7 Hz, 1H), 7.20-7.11 (m, 2H), 7.01 (d, J = 8.0 Hz, 1H), 6.71 (d, J = 9.2 Hz, 1H), 5.27 (s, 2H), 2.59 (s, 3H), 2.54 (t, J = 7.9 Hz, 2H), 1.47-1.37 (m, 2H), 0.79 (t, J = 7.5 Hz, 3H). |
| 8 | Method of Example 3 | 1-(2-Hydroxy-3-methyl-4-{3-[4-(1H-tetrazol-5-yl)-pyridin-2-yloxy]-benzyloxy}-phenyl)-propan-1-one | 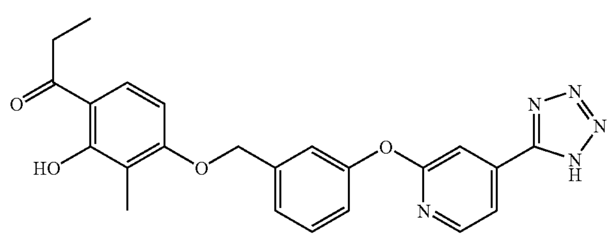 | MS (m/z): 430.2 (M − 1). $^1$H NMR (DMSO-$d_6$) 12.92 (s, 1H), 8.41 (d, J = 5.0 Hz, 1H), 7.86 (d, J = 9.0 Hz, 1H), 7.76 (d, J = 5.0 Hz, 1H), 7.62 (s, 1H), 7.51 (t, J = 8.0 Hz, 1H), 7.37 (d, J = 7.7 Hz, 1H), 7.31 (s, 1H), 7.20 (d, J = 8.0 Hz, 1H), 6.74 (d, J = 9.0 Hz, 1H), 5.31 (s, 2H), 3.06 (q, J = 7.3 Hz, 2H), 2.05 (s, 3H), 1.11 (t, J = 7.3 Hz, 3H). |
| 9 | Method of Example 3 | 1-(2-Hydroxy-3-propyl-4-{4-[4-(1H-tetrazol-5-yl)-pyridin-2-yloxy]-benzyloxy}-phenyl)-ethanone | 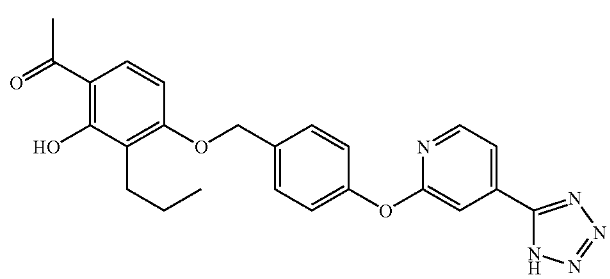 | MS (m/z): 444.2 (M − 1). $^1$H NMR (DMSO-$d_6$) 12.88 (s, 1H), 8.39 (s, 1H), 7.85 (d, J = 9.0 Hz, 1H), 7.76 (bs, 1H), 7.62 (bs, 1H), 7.54 (d, J = 8.2 Hz, 2H), 7.27 (d, J = 8.2 Hz, 2H), 6.79 (d, J = 9.0 Hz, 1H), 5.31 (s, 2H), 2.62 (t, J = 7.5 Hz, 2H), 2.60 (s, 3H), 1.58-1.47 (m, 2H), 0.90 (t, J = 7.5 Hz, 3H). |

-continued

| Ex. # | Method # | Chemical name | Structure | Physical data |
|---|---|---|---|---|
| 10 | Method of Example 1 | 1-(2-Hydroxy-3-propyl-4-{4-[3-(1H-tetrazol-5-yl)-pyridin-2-yloxy]-benzyloxy}-phenyl)-ethanone | 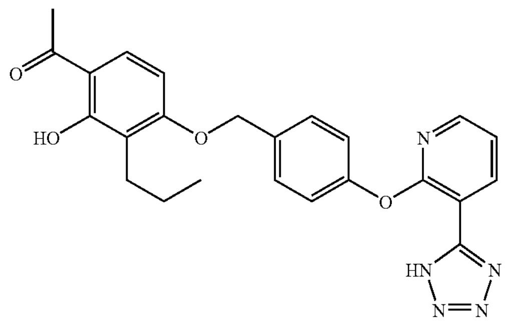 | MS (m/z): 444.1 (M − 1). $^1$H NMR (DMSO-$d_6$) 12.88 (s, 1H), 8.57 (d, J = 7.4 Hz, 1H), 8.32 (d, J = 5.0 Hz, 1H), 7.84 (d, J = 9.2 Hz, 1H), 7.54 (d, J = 8.2 Hz, 2H), 7.38 (dd, J = 5.0 Hz, 7.4 Hz, 1H), 7.29 (d, J = 8.2 Hz, 2H), 6.79 (d, J = 9.2 Hz, 1H), 5.31 (s, 2H), 2.62 (t, J = 7.4 Hz, 2H), 2.60 (s, 3H), 1.57-1.47 (m, 2H), 0.90 (t, J = 7.4 Hz, 3H). |
| 11 | Method of Example 1 | 1-(2-Hydroxy-3-propyl-4-{3-[4-(1H-tetrazol-5-yl)-pyridin-2-yloxy]-benzyloxy}-phenyl)-ethanone | 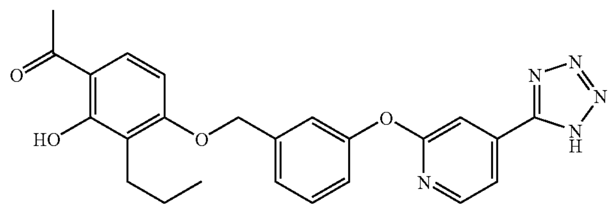 | MS (m/z): 444.2 (M − 1). $^1$H NMR (DMSO-$d_6$) 12.86 (s, 1H), 8.41 (d, J = 5.1 Hz, 1H), 7.83 (d, J = 8.9 Hz, 1H), 7.77 (d, J = 5.1 Hz, 1H), 7.62 (s, 1H), 7.51 (t, J = 7.9 Hz, 1H), 7.35 (d, J = 7.6 Hz, 1H), 7.29 (s, 1H), 7.20 (d, J = 7.9 Hz, 1H), 6.74 (d, J = 8.9 Hz, 1H), 5.31 (s, 2H), 2.59 (s, 3H), 2.57 (t, J = 7.4 Hz, 2H), 1.50-1.40 (m, 2H), 0.81 (t, J = 7.4 Hz, 3H). |
| 12 | Method of Example 1 | 1-(2-Hydroxy-3-methyl-4-{3-[4-(1H-tetrazol-5-yl)-phenoxy]-benzyloxy}-phenyl)-propan-1-one | 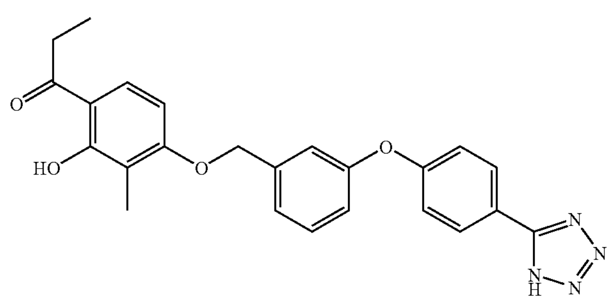 | MS (m/z): 429.1 (M − 1). $^1$H NMR (DMSO-$d_6$) 12.91 (s, 1H), 8.07 (d, J = 8.5 Hz, 2H), 7.85 (d, J = 9.2 Hz, 1H), 7.50 (d, J = 8.2 Hz, 1H), 7.33 (d, J = 7.8 Hz, 1H), 7.23 (d, J = 8.5 Hz, 2H), 7.21 (s, 1H), 7.11 (d, J = 8.2 Hz, 1H), 6.72 (d, J = 9.2 Hz, 1H), 5.30 (s, 2H), 3.06 (q, J = 7.2 Hz, 2H), 2.03 (s, 3H), 1.11 (t, J = 7.2 Hz, 3H). |
| 13 | Method of Example 1 | 1-(2-Hydroxy-3-propyl-4-{3-[4-(1H-tetrazol-5-yl)-phenoxy]-benzyloxy}-phenyl)-ethanone | 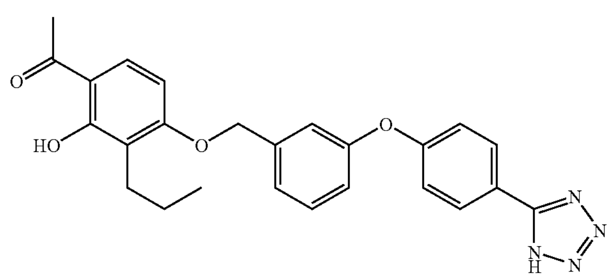 | MS (m/z): 443.2 (M − 1). $^1$H NMR (DMSO-$d_6$) 12.85 (s, 1H), 8.07 (d, J = 8.4 Hz, 2H), 7.83 (d, J = 9.1 Hz, 1H), 7.51 (t, J = 7.6 Hz, 1H), 7.30 (d, J = 7.6 Hz, 1H), 7.24 (d, J = 8.4 Hz, 2H), 7.18 (s, 1H), 7.13 (d, J = 8.4 Hz, 1H), 6.72 (d, J = 9.1 Hz, 1H), 5.30 (s, 2H), 2.59 (s, 3H), 2.55 (t, J = 7.7 Hz, 2H), 1.47-1.38 (m, 2H), 0.79 (t, J = 7.7 Hz, 3H). |

-continued

| Ex. # | Method # | Chemical name | Structure | Physical data |
|---|---|---|---|---|
| 14 | Method of Example 1 | 1-(2-Hydroxy-3-methyl-4-{3-[3-(1H-tetrazol-5-yl)-5-trifluoromethyl-phenoxy]-benzyloxy}-phenyl)-propan-1-one | 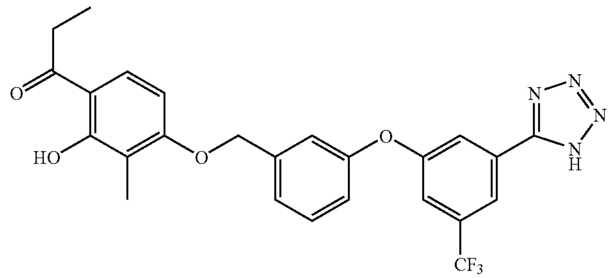 | MS (m/z): 497.1 (M − 01). $^1$H NMR (DMSO-$d_6$) 12.89 (s, 1H), 8.14 (s, 1H), 7.91 (s, 1H), 7.83 (d, J = 9.1 Hz, 1H), 7.63 (s, 1H), 7.55 (t, J = 7.9 Hz, 1H), 7.38 (d, J = 7.6 Hz, 1H), 7.28 (s, 1H), 7.21 (d, J = 7.9 Hz, 1H), 6.72 (d, J = 9.1 Hz, 1H), 5.31 (s, 2H), 3.05 (q, J = 7.1 Hz, 2H), 1.99 (s, 3H), 1.11 (t, J = 7.1 Hz, 3H). |
| 15 | Method of Example 1 | 1-(2-Hydroxy-3-methyl-4-{4-[3-(1H-tetrazol-5-yl)-phenoxy]-benzyloxy}-phenyl)-propan-1-one | 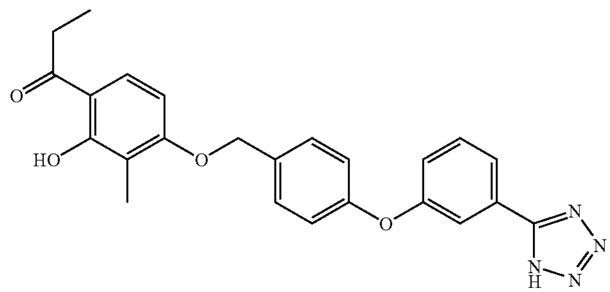 | MS (m/z): 429.1 (M − 1). $^1$H NMR (DMSO-$d_6$) 12.93 (s, 1H), 7.87 (d, J = 9.0 Hz, 1H), 7.84 (d, J = 7.9 Hz, 1H), 7.69-7.63 (m, 2H), 7.56 (d, J = 8.6 Hz, 2H), 7.28 (dd, J = 2.2 Hz, 8.1 Hz, 1H), 7.17 (d, J = 8.6 Hz, 2H), 6.77 (d, J = 9.0 Hz, 1H), 5.28 (s, 2H), 3.07 (q, J = 7.2 Hz, 2H), 2.07 (s, 3H), 1.12 (t, J = 7.2 Hz, 3H). |
| 16 | Method of Example 1 | 1-(2-Hydroxy-3-methyl-4-{3-[5-(1H-tetrazol-5-yl)-pyridin-2-yloxy]-benzyloxy}-phenyl)-propan-1-one | 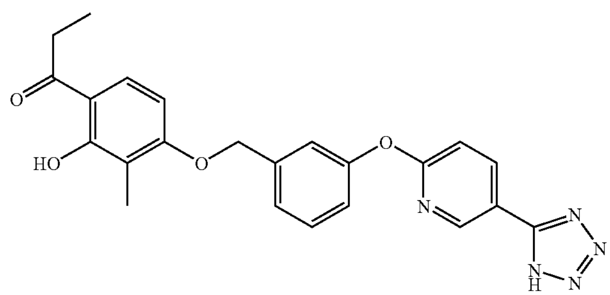 | MS (m/z): 430.1 (M − 1). $^1$H NMR (DMSO-$d_6$) 12.92 (s, 1H), 8.80 (s, 1H), 8.45 (dd, J = 2.2 Hz, 8.5 Hz, 1H), 7.86 (d, J = 8.9 Hz, 1H), 7.52 (t, J = 8.0 Hz, 1H), 7.38 (d, J = 7.6 Hz, 1H), 7.33-7.29 (m, 2H), 7.20 (d, J = 8.0 Hz, 1H), 6.75 (d, J = 8.9 Hz, 1H), 5.32 (s, 2H), 3.07 (q, J = 7.2 Hz, 2H), 2.06 (s, 3H), 1.11 (t, J = 7.2 Hz, 3H). |
| 17 | Method of Example 1 | 1-(3-Fluoro-2-hydroxy-4-{3-[5-(1H-tetrazol-5-yl)-pyridin-2-yloxy]-benzyloxy}-phenyl)-ethanone | 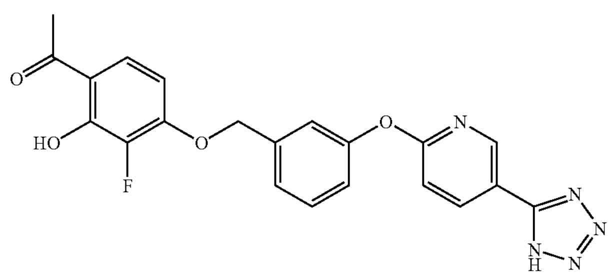 | MS (m/z): 419.9 (M − 1). $^1$H NMR (DMSO-$d_6$) 12.36 (s, 1H), 8.80 (s, 1H), 8.46 (d, J = 8.8 Hz, 1H), 7.77 (d, J = 9.1 Hz, 1H), 7.52 (t, J = 8.0 Hz, 1H), 7.39 (d, J = 7.8 Hz, 1H), 7.34-7.29 (m, 2H), 7.23 (d, J = 8.0 Hz, 1H), 6.92 (t, J = 8.0 Hz, 1H), 5.37 (s, 2H), 2.62 (s, 3H). |
| 18 | Method of Example 1 | 1-(3-Chloro-2-hydroxy-4-{3-[5-(1H-tetrazol-5-yl)-pyridin-2-yloxy]-benzyloxy}-phenyl)-ethanone | 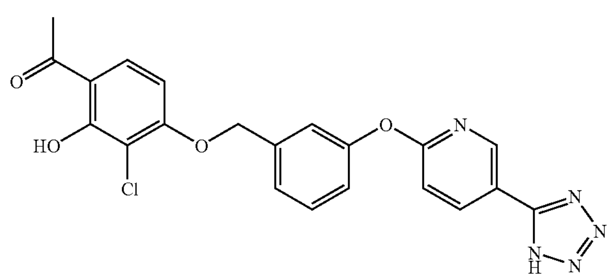 | MS (m/z): 435.9 (M − 1). $^1$H NMR (DMSO-$d_6$) 13.16 (s, 1H), 8.80 (s, 1H), 8.46 (d, J = 8.5 Hz, 1H), 7.98 (d, J = 9.2 Hz, 1H), 7.53 (t, J = 7.8 Hz, 1H), 7.39 (d, J = 7.8 Hz, 1H), 7.34-7.30 (m, 2H), 7.22 (d, J = 8.0 Hz, 1H), 6.93 (d, J = 9.2 Hz, 1H), 5.42 (s, 2H), 2.65 (s, 3H). |

-continued

| Ex. # | Method # | Chemical name | Structure | Physical data |
|---|---|---|---|---|
| 19 | Method of Example 1 | 1-(2-Hydroxy-3-methyl-4-{3-[5-(1H-tetrazol-5-yl)-pyridin-2-yloxy]-benzyloxy}-phenyl)-ethanone | 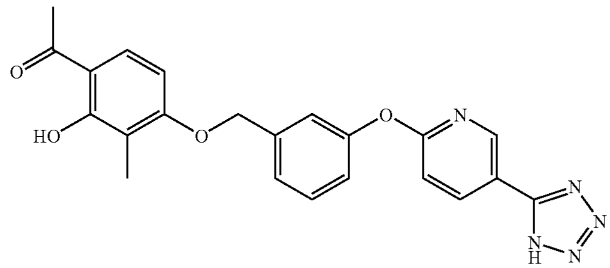 | MS (m/z): 416.0 (M − 1). $^1$H NMR (DMSO-$d_6$) 12.87 (s, 1H), 8.80 (s, 1H), 8.46 (d, J = 8.6 Hz, 1H), 7.84 (d, J = 9.1 Hz, 1H), 7.52 (t, J = 7.9 Hz, 1H), 7.38 (d, J = 7.6 Hz, 1H), 7.33-7.16 (m, 3H), 6.76 (t, J = 9.1 Hz, 1H), 5.32 (s, 2H), 2.60 (s, 3H), 2.06 (s, 3H). |
| 20 | Method of Example 1 | 1-(3-Chloro-2-hydroxy-4-{3-[4-(1H-tetrazol-5-yl)-pyridin-2-yloxy]-benzyloxy}-phenyl)-ethanone | 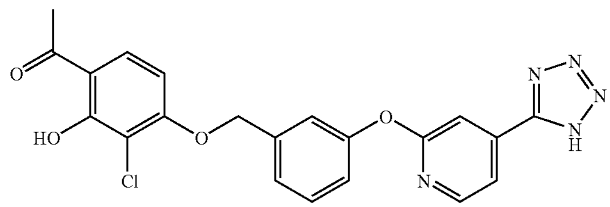 | MS (m/z): 435.9 (M − 1). $^1$H NMR (DMSO-$d_6$) 13.16 (s, 1H), 8.40 (d, J = 5.1 Hz, 1H), 7.97 (d, J = 9.2 Hz, 1H), 7.77 (d, J = 5.1 Hz, 1H), 7.62 (s, 1H), 7.52 (t, J = 8.1 Hz, 1H), 7.38 (d, J = 7.6 Hz, 1H), 7.33 (s, 1H), 7.21 (d, J = 8.1 Hz, 1H), 6.93 (d, J = 9.2 Hz, 1H), 5.42 (s, 2H), 2.65 (s, 3H). |
| 21 | Method of Example 1 | 1-(2-Hydroxy-3-methyl-4-{4-[4-(1H-tetrazol-5-yl)-pyridin-2-yloxy]-benzyloxy}-phenyl)-ethanone | 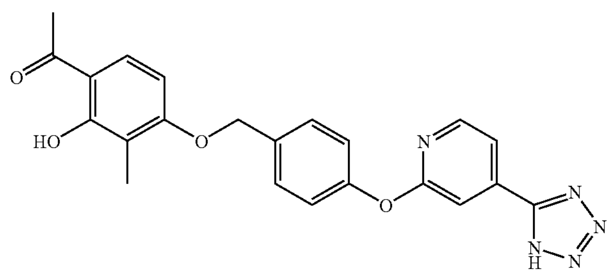 | MS (m/z): 416.0 (M − 1). $^1$H NMR (DMSO-$d_6$) 12.88 (s, 1H), 8.39 (d, J = 5.0 Hz, 1H), 7.86, J = 9.0 Hz, 1H), 7.75 (d, J = 5.0 Hz, 1H), 7.62 (s, 1H), 7.56 (d, J = 8.6 Hz, 2H), 7.26 (d, J = 8.6 Hz, 2H), 6.80 (d, J = 9.0 Hz, 1H), 5.31 (s, 2H), 2.61 (s, 3H), 2.08 (s, 3H). |
| 22 | Method of Example 1 | 1-(2-Hydroxy-3-methyl-4-{4-[3-(1H-tetrazol-5-yl)-phenoxy]-benzyloxy}-phenyl)-ethanone | 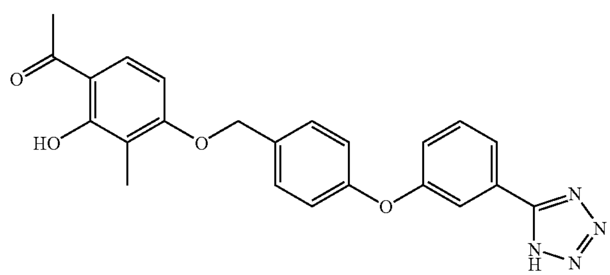 | MS (m/z): 416.0 (M − 1). $^1$H NMR (DMSO-$d_6$) 12.88 (s, 1H), 8.39 (d, J = 5.0 Hz, 1H), 7.86, J = 9.0 Hz, 1H), 7.75 (d, J = 5.0 Hz, 1H), 7.62 (s, 1H), 7.56 (d, J = 8.6 Hz, 2H), 7.26 (d, J = 8.6 Hz, 2H), 6.80 (d, J = 9.0 Hz, 1H), 5.31 (s, 2H), 2.61 (s, 3H), 2.08 (s, 3H). |
| 23 | Method of Example 3 | 1-(2-Hydroxy-4-{4-[3-(1H-tetrazol-5-yl)-phenoxy]-benzyloxy}-phenyl)-ethanone | 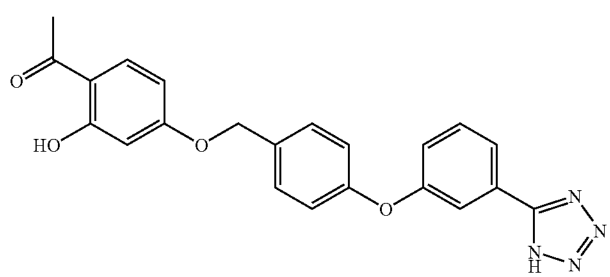 | $^1$H NMR (DMSO-$d_6$) 12.87 (s, 1H), 7.84 (d, J = 7.2 Hz, 2H), 7.70-7.61 (m, 2H), 7.56 (d, J = 7.2 Hz, 2H), 7.27 (d, J = 8.1 Hz, 1H), 7.17 (d, J = 7.2 Hz, 2H), 6.78 (d, J = 8.6 Hz, 1H), 5.28 (s, 2H), 2.60 (s, 3H), 2.06 (s, 3H). |

| Ex. # | Method # | Chemical name | Structure | Physical data |
|---|---|---|---|---|
| 24 | Method of Example 3 | 1-(2-Hydroxy-3-propyl-4-{6-[3-(1H-tetrazol-5-yl)-phenoxy]-pyridin-3-ylmethoxy}-phenyl)-ethanone | 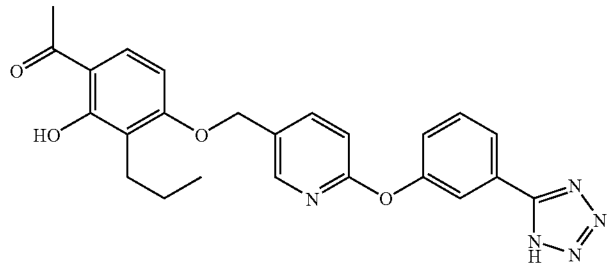 | $^1$H NMR (DMSO-d$_6$) 12.64 (s, 1H), 7.79 (d, J = 7.2 Hz, 1H), 7.71 (bs, 1H), 7.63 (dd, J = 2.0 Hz, 8.5 Hz, 1H), 7.50-7.31 (m, 3H), 7.06 (d, J = 7.2 Hz, 1H), 7.00 (d, J = 8.2 Hz, 2H), 6.47 (d, J = 9.0 Hz, 1H), 6.42 (s, 1H), 5.02 (s, 2H), 2.51 (s, 3H). |
| 25 | Method of Example 3 | 1-(2-Hydroxy-3-methyl-4-{6-[3-(1H-tetrazol-5-yl)-phenoxy]-pyridin-3-ylmethoxy}-phenyl)-propan-1-one | 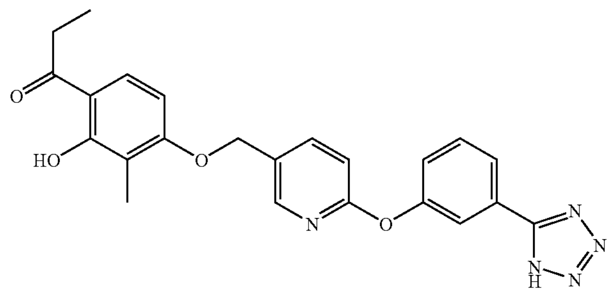 | $^1$H NMR (DMSO-d$_6$) 12.86 (s, 1H), 8.29 (s, 1H), 8.01 (dd, J = 2.2 Hz, 8.4 Hz, 1H), 7.93 (d, J = 8.0 Hz, 1H), 7.85 (d, J = 9.1 Hz, 1H), 7.81 (s, 1H), 7.69 (t, J = 8.0 Hz, 1H), 7.41 (d, J = 8.0 Hz, 1H), 7.23 (d, J = 8.4 Hz, 1H), 6.80 (d, J = 9.1 Hz, 1H), 5.27 (s, 2H), 2.60 (s, 3H), 2.57 (t, J = 7.5 Hz, 2H), 1.51-1.43 (m, 2H), 0.86 (t, J = 8.5 Hz, 3H). |
| 26 | Method of Example 1 | 1-(2-Hydroxy-4-{4-[3-(2H-tetrazol-5-yl)-phenoxy]-benzyloxy}-3-trifluoromethyl-phenyl)-ethanone | 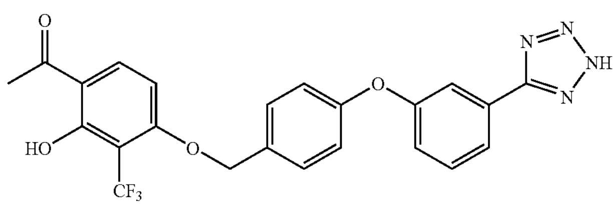 | $^1$H NMR (DMSO-d$_6$) 12.92 (s, 1H), 8.31 (s, 1H), 8.04 (dd, J = 2.2 Hz, 8.4 Hz, 1H), 7.93 (d, J = 7.6 Hz, 1H), 7.89 (d, J = 9.1 Hz, 1H), 7.82 (s, 1H), 7.69 (t, J = 8.2 Hz, 1H), 7.42 (d, J = 8.2 Hz, 1H), 7.22 (d, J = 8.4 Hz, 1H), 6.80 (d, J = 9.1 Hz, 1H), 5.26 (s, 2H), 3.07 (q, J = 7.2 Hz, 2H), 2.03 (s, 3H), 1.11 (t, J = 7.2 Hz, 2H). |
| 27 | Method of Example 1 | 1-(2-Hydroxy-4-{3-[4-(2H-tetrazol-5-yl)-pyridin-2-yloxy]-benzyloxy}-3-trifluoromethyl-phenyl)-ethanone | 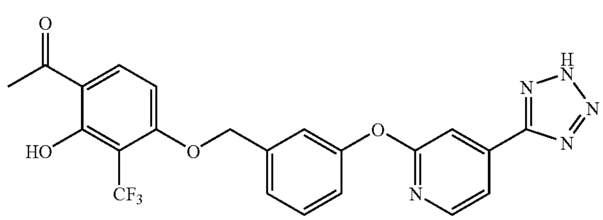 | LC-MS (m/e): 469 (M − 1); $^1$H NMR (DMSO-d$_6$) δ 13.81 (1H, s), 8.25 (1H, d), 7.85 (1H, d), 7.65 (2H, m), 7.53 (2H, d), 7.28 (1H, m), 7.18 (2H, d), 6.98 (1H, d), 5.40 (2H, s), 2.67 (3H, s) |
| 28 | Method of Example 1 | 1-(2-Hydroxy-4-{3-[5-(2H-tetrazol-5-yl)-pyridin-2-yloxy]-benzyloxy}-3-trifluoromethyl-phenyl)-ethanone | 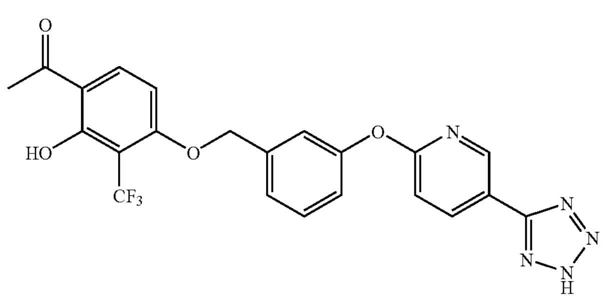 | LC-MS (m/e): 470 (M − 1); $^1$H NMR (DMSO-d$_6$) δ 13.80 (1H, s), 8.41 (1H, d), 8.23 (1H, d), 7.78 (1H, dd), 7.62 (1H, s), 7.51 (1H, dd), 7.35 (1H, d), 7.29 (1H, s), 7.21 (1H, d), 6.94 (1H, d), 5.44 (2H, s), 2.65 (3H, s). |

-continued

| Ex. # | Method # | Chemical name | Structure | Physical data |
|---|---|---|---|---|
| 29 | Method of Example 3 | 1-(2-Hydroxy-3-propyl-4-{3-[3-(2H-tetrazol-5-yl)-phenylsulfanyl]-benzyloxy}-phenyl)-ethanone | 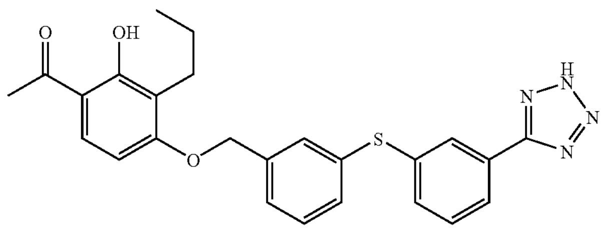 | LC-MS (m/e): 470 (M − 1); $^1$H NMR (DMSO-d$_6$) δ 13.53 (1H, s), 8.30 (1H, d), 8.47 (1H, dd), 8.23 (1H, d), 7.52 (1H, dd), 7.15-7.44 (4H, m), 6.95 (1H, d), 5.45 (2H, s), 2.65 (3H, s). |
| 30 | Method of Example 3 | 1-(2-Hydroxy-3-propyl-4-{2-[3-(2H-tetrazol-5-yl)-phenylsulfanyl]-benzyloxy}-phenyl)-ethanone | 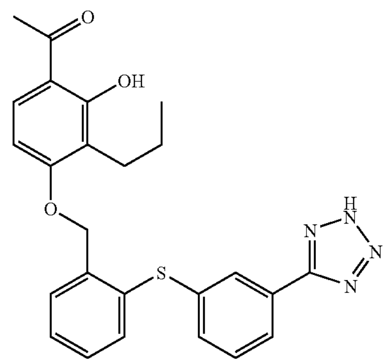 | $^1$H NMR (400 MHz, acetone-d$_6$) δ 0.85 (t, J = 7.4 Hz, 3H), 1.48 (sextuplet, J = 10.2 Hz, 2H), 2.57 (s, 3H), 2.60 (t, J = 7.4 Hz, 2H), 5.29 (s, 2H), 6.66 (d, J = 9.0 Hz, 1H), 7.43-7.60 (m, 6H), 7.76 (d, J = 9.0 Hz, 1H), 8.04 (d, J = 9.0 Hz, 1H), 8.11 (s, 1H), 12.87 (s, 1H). MS (m/z): 459 (M − 1). |
| 31 | Method of Example 3 | 1-(2-Hydroxy-3-propyl-4-{3-[4-(1H-tetrazol-5-yl)-phenylsulfanyl]-benzyloxy}-phenyl)-ethanone | 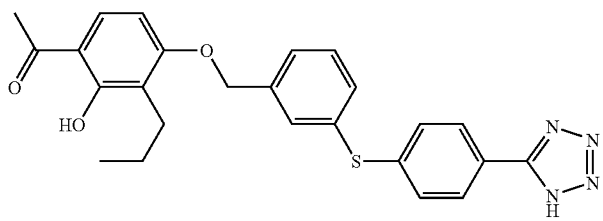 | $^1$H NMR (400 MHz, acetone-d$_6$) δ 0.89 (t, J = 7.2 Hz, 3H), 1.53 (q, J = 7.8 Hz, 2H), 2.54 (s, 3H), 2.63 (t, J = 7.6 Hz, 2H), 5.38 (s, 2H), 6.61 (d, J = 9.0 Hz, 1H), 7.44 (m, 2H), 7.49 (m, 1H), 7.58 (m, 2H), 7.70 (m, 2H), 7.99 (d, J = 9.0 Hz, 1H), 8.02 (s, 1H), 12.86 (s, 1H). MS (m/z): 459 (M − 1). |
| 32 | Method of Example 3 | 1-(2-Hydroxy-3-propyl-4-{2-[4-(2H-tetrazol-5-yl)-phenylsulfanyl]-benzyloxy}-phenyl)-ethanone | 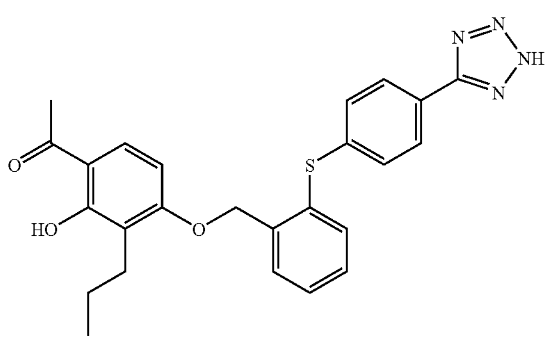 | $^1$H NMR (400 MHz, acetone-d$_6$) δ 0.85 (t, J = 7.4 Hz, 3H), 1.47 (m, 2H), 2.57 (s, 3H), 2.63 (t, J = 7.4 Hz, 2H), 5.30 (s, 1H), 6.68 (d, J = 9.0 Hz, 1H), 7.44-7.53 (m, 5H), 7.62 (s, 1H), 7.77 (d, J = 9.0 Hz, 1H), 8.07 (d, J = 9.0 Hz, 2H), 12.86 (s, 1H). MS (APCI-NEG) m/z (rel intensity) 459 (100). |
| 33 | Method of Example 1 | 1-(2-Hydroxy-3-propyl-4-{4-[2-(2H-tetrazol-5-yl)-phenylsulfanyl]-benzyloxy}-phenyl)-ethanone | 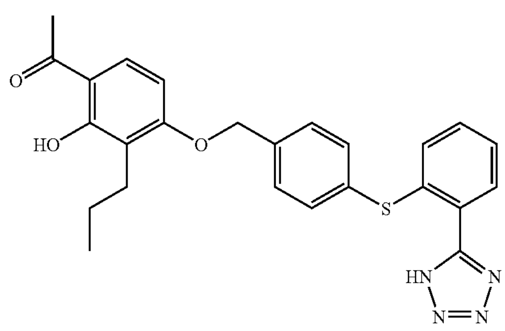 | $^1$H NMR (400 MHz, acetone-d$_6$) δ 0.90 (t, J = 7.4 Hz, 3H), 1.58-1.49 (m, 2H), 2.56 (s, 3H), 2.64 (t, J = 7.6 Hz, 2H), 5.38 (s, 2H), 6.61 (d, J = 9.0 Hz, 1H), 7.39 (d, J = 8.6 Hz, 2H), 7.49 (t, J = 8.4 Hz, 1H), 7.57 (t, J = 7.6 Hz, 15H), 7.62 (d, J = 7.8 Hz, 11H), 7.74 (d, J = 9.0 Hz, 2H), 8.06 (d, J = 8.6 Hz, 2H), 12.86 (s, 1H). MS (m/z): 459 (M − 1). |

| Ex. # | Method # | Chemical name | Structure | Physical data |
|---|---|---|---|---|
| 34 | Method of Example 1 | 1-(2-Hydroxy-3-propyl-4-{3-[2-(2H-tetrazol-5-yl)-phenylsulfanyl]-benzyloxy}-phenyl)-ethanone | 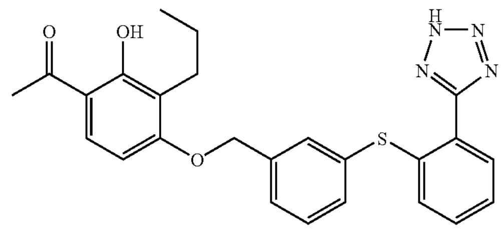 | $^1$H NMR (400 MHz, DMSO-d$_6$) δ 0.87 (t, J = 7.4 Hz, 3H), 1.46-1.50 (m, 2H), 2.51 (s, 3H), 2.58 (m, 2H), 5.28 (s, 2H), 6.73 (d, J = 9.0 Hz, 1H), 7.18 (d, J = 8.2 Hz, 1H), 7.37-7.44 (m, 2H), 7.47-7.51 (m, 4H), 7.82 (d, J = 9.0 Hz, 2H), 12.85 (s, 1H). MS (m/z): 459 (M − 1). |
| 35 | Method of Example 1 | 1-(2-Hydroxy-3-propyl-4-{4-[4-(2H-tetrazol-5-yl)-phenylsulfanyl]-benzyloxy}-phenyl)-ethanone | 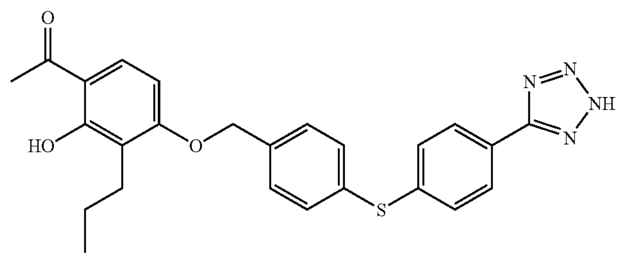 | $^1$H NMR (400 MHz, DMSO-d$_6$) δ 0.79 (s, 3H), 1.43 (q, J = 10.3 Hz, 2H), 2.50 (s, 3H), 2.57 (m, 2H), 5.25 (s, 2H), 6.69 (d, J = 9.0 Hz, 1H), 6.95 (m, 1H), 7.23 (m, 2H), 7.34 (s, 1H), 7.42 (s, 2H), 7.48 (s, 1H), 7.73 (m, 1H), 7.78 (d, J = 9.0 Hz, 1H), 12.83 (s, 1H). MS (m/z): 459 (M − 1). |
| 36 | Method of Example 1 | 1-(2-Hydroxy-3-propyl-4-{4-[3-(2H-tetrazol-5-yl)-phenylsulfanyl]-benzyloxy}-phenyl)-ethanone | 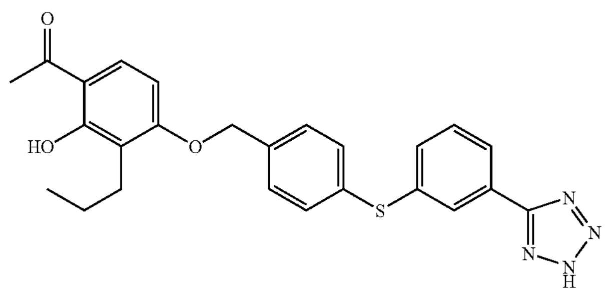 | $^1$H NMR (400 MHz, DMSO-d$_6$) δ 0.86 (t, J = 7.2 Hz, 3H), 1.48 (q, J = 9.8 Hz, 2H), 2.57 (s, 3H), 2.58 (m, 2H), 5.26 (s, 2H), 6.71 (d, J = 9.0 Hz, 1H), 7.37-7.40 (m, 4H), 7.45 (d, J = 8.2 Hz, 2H), 7.80 (d, J = 9.0 Hz, 1H), 7.98 (d, J = 8.6 Hz, 2H), 12.84 (s, 1H). MS (m/z): 459 (M − 1). |
| 37 | Method of Example 1 | 1-(2-Hydroxy-3-propyl-4-{3-[2-(2H-tetrazol-5-yl)-benzenesulfonyl]-benzyloxy}-phenyl)-ethanone | 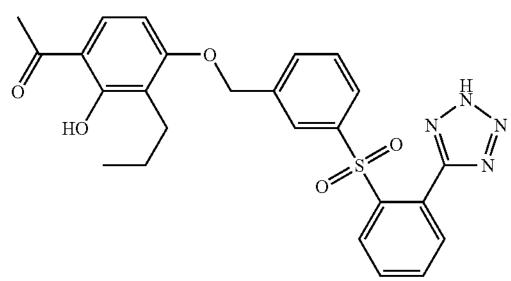 | $^1$H NMR (400 MHz, DMSO-d$_6$) δ 0.90 (t, J = 7.2 Hz, 3H), 1.54 (q, J = 10 Hz, 2H), 2.57 (s, 2H), 2.57 (s, 3H), 2.64 (q, J = 10 Hz, 2H), 5.26 (s, 2H), 6.67 (m, 1H), 7.29-7.44 (m, 6H), 7.79 (d, J = 9.0 Hz, 1H), 8.04 (m, 1H), 8.12 (s, 1H), 12.88 (s, 1H). MS (m/z): 459 (M − 1). |
| 38 | Method of Example 1 | 1-(2-Hydroxy-3-propyl-4-{3-[3-(2H-tetrazol-5-yl)-benzenesulfonyl]-benzyloxy}-phenyl)-ethanone | 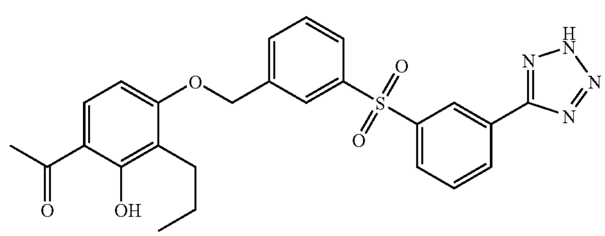 | $^1$H NMR (400 MHz, DMSO-d$_6$) δ 0.86 (t, J = 7.4 Hz, 3H), 1.47 (q, J = 9.6 Hz, 2H), 2.50 (s, 3H), 2.56 (m, 2H), 5.32 (s, 2H), 6.72 (d, J = 9.4 Hz, 1H), 7.45 (m, 1H), 7.58 (s, 1H), 7.65 (s, 1H), 7.71 (s, 2H), 7.79 (d, J = 9.0 Hz, 1H), 7.87 (m, 2H), 8.21 (m, 1H), 12.84 (s, 1H). MS (m/z): 491 (M − 1). |

| Ex. # | Method # | Chemical name | Structure | Physical data |
|---|---|---|---|---|
| 39 | Method of Example 1 | 1-(2-Hydroxy-3-propyl-4-{4-[4-(2H-tetrazol-5-yl)-benzenesulfonyl]-benzyloxy}-phenyl)-ethanone | 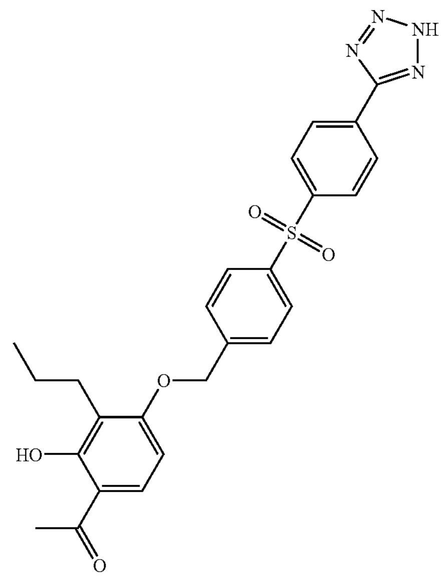 | $^1$H NMR (400 MHz, DMSO-d$_6$) δ0.83 (t, J = 7.4 Hz, 3H), 1.44 (m, 2H), 2.55 (s, 3H), 2.57 (m, 2H), 5.36 (s, 2H), 6.69 (d, J = 9.0 Hz, 1H), 7.65-7.70 (m, 2H), 7.74 (d, J = 7.4 Hz, 1H), 7.78 (d, J = 9.4 Hz, 1H), 7.90 (d, J = 8.2 Hz, 1H), 7.96 (d, J = 7.8 Hz, 1H), 8.08 (s, 1H), 8.27 (d, J = 7.8 Hz, 1H), 8.50 (s, 1H), 12.84 (s, 1H). MS (m/z): 491 (M − 1). |
| 40 | Method of Example 1 | 1-(2-Hydroxy-3-propyl-4-{4-[3-(2H-tetrazol-5-yl)-benzenesulfonyl]-benzyloxy}-phenyl)-ethanone | 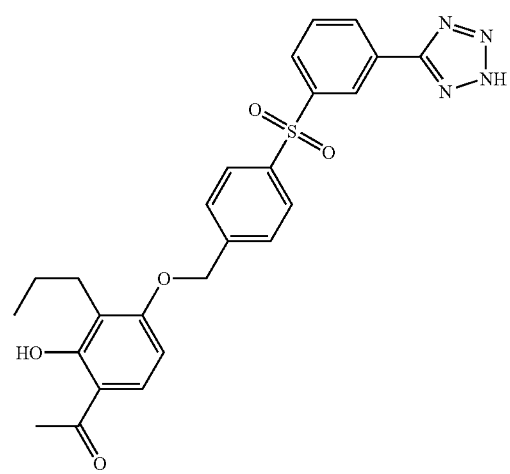 | $^1$H NMR (400 MHz, DMSO-d$_6$) δ0.87 (t, J = 7.4 Hz, 3H), 1.48 (m, 2H), 2.50 (s, 3H), 2.60 (t, J = 7.6 Hz, 2H), 5.36 (s, 2H), 6.65 (d, J = 9.0 Hz, 1H), 7.67 (d, J = 8.6 Hz, 2H), 7.78 (d, J = 9.0 Hz, 1H), 8.03 (d, J = 6.6 Hz, 2H), 8.05 (d, J = 7.0 Hz, 2H), 8.22 (d, J = 9.0 Hz, 2H), 12.84 (s, 2H). MS (m/z): 491 (M − 1). |
| 41 | Method of Example 1 | 1-(2-Hydroxy-3-propyl-4-{3-[4-(2H-tetrazol-5-yl)-benzenesulfonyl]-benzyloxy}-phenyl)-ethanone | 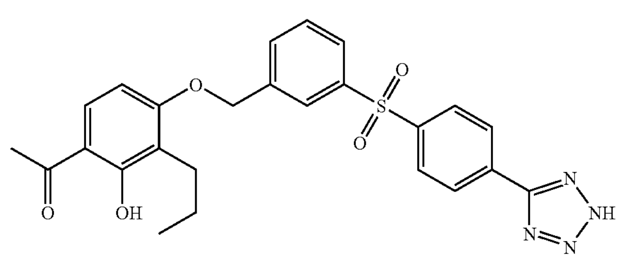 | $^1$H MAR (400 MHz, DMSO-d$_6$) δ 0.87 (t, J = 7.4 Hz, 3H), 1.48 (q, J = 9.5 Hz, 2H), 2.50 (s, 3H), 2.55 (m, 2H), 5.36 (s, 2H), 6.65 (d, J = 9.0 Hz, 1H), 7.67 (d, J = 7.8 Hz, 3H), 7.78 (d, J = 9.0 Hz, 1H), 7.89 (d, J = 8.2 Hz, 1H), 8.04 (d, J = 8.2 Hz, 2H), 8.24 (d, J = 8.2 Hz, 1H), 8.47 (s, 1H), 12.83 (s, 1H). MS (m/z): 491 (M − 1). |

-continued

| Ex. # | Method # | Chemical name | Structure | Physical data |
|---|---|---|---|---|
| 42 | Method of Example 2 | 1-(2-Hydroxy-3-propyl-4-{2-[3-(1H-tetrazol-5-yl)-benzenesulfinyl]-benzyloxy}-phenyl)-ethanone | 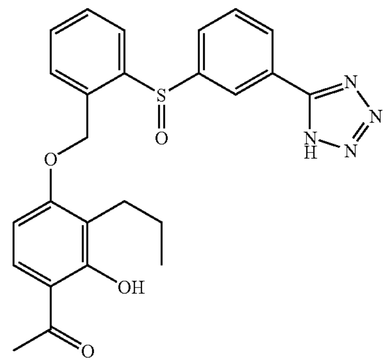 | $^1$H NMR (400 MHz, DMSO-d$_6$) δ 0.87 (t, J = 7.4 Hz, 3H), 1.48 (m, 2H), 2.56 (s, 3H), 2.59 (t, J = 7.4 Hz, 2H), 5.36 (s, 2H), 6.70 (d, J = 9.0 Hz, 1H), 7.68 (d, J = 7.8 Hz, 1H), 7.74 (d, J = 7.4 Hz, 1H), 7.80 (d, J = 9.0 Hz, 1H), 7.95 (d, J = 7.8 Hz, 1H), 7.98 (d, J = 8.6 Hz, 2H), 8.07 (s, 1H), 8.20 (d, J = 8.6 Hz, 2H), 12.85 (s, 1H). MS (m/z): 491 (M − 1). |
| 43 | Method of Example 2 | 1-(2-Hydroxy-3-propyl-4-{3-[2-(1H-tetrazol-5-yl)-benzenesulfinyl]-benzyloxy}-phenyl)-ethanone | 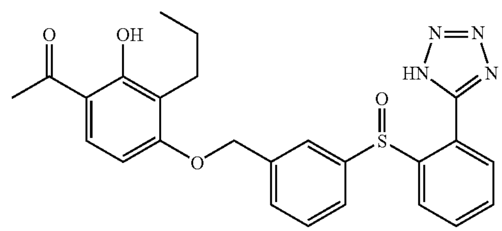 | $^1$H NMR (400 MHz, acetone-d$_6$) δ 0.86 (t, J = 7.4 Hz, 3H), 1.45-1.53 (m, 2H), 2.56 (s, 3H), 2.63 (m, 2H), 5.43 (d, J = 12.5 Hz, 1H), 5.53 (d, J = 12.5 Hz, 1H), 6.62 (d, J = 9.0 Hz, 1H), 7.65-7.72 (m, 3H), 7.76 (d, J = 8.6 Hz, 1H), 7.89 (d, J = 8.6 Hz, 2H), 8.01 (m, 1H), 8.26 (d, J = 8.6 Hz, 2H), 12.86 (s, 3H). MS (m/z): 475 (M − 1). |
| 44 | Method of Example 2 | 1-(2-Hydroxy-3-propyl-4-{4-[4-(1H-tetrazol-5-yl)-benzenesulfinyl]-benzyloxy}-phenyl)-ethanone | 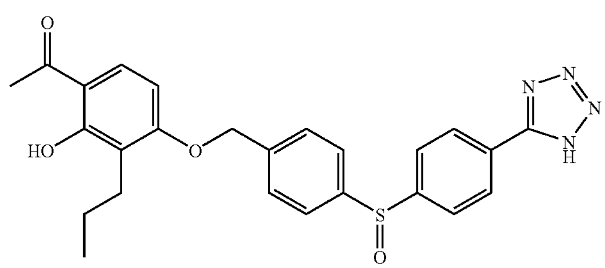 | $^1$H NMR (400 MHz, acetone-d$_6$) δ 0.88 (t, J = 7.4 Hz, 3H), 1.51 (m, 2H), 2.58 (s, 3H), 2.62 (t, J = 7.6 Hz, 2H), 5.29 (s, 1H), 6.62 (d, J = 9.0 Hz, 1H), 7.50 (t, J = 7.6 Hz, 1H), 7.55 (d, J = 7.8 Hz, 1H), 7.75 (m, 3H), 7.84 (m, 1H), 7.89 (s, 1H), 8.05 (m, 1H), 8.26 (m, 1H), 12.88 (s, 1H). MS (m/z): 475 (M − 1). |
| 45 | Method of Example 2 | 1-(2-Hydroxy-3-propyl-4-{4-[3-(1H-tetrazol-5-yl)-benzenesulfinyl]-benzyloxy}-phenyl)-ethanone | 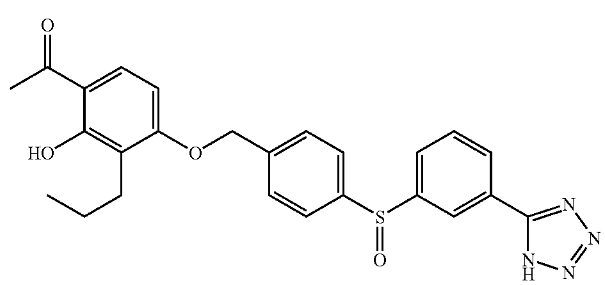 | $^1$H NMR (400 MHz, acetone-d$_6$) δ 0.90 (t, J = 7.4 Hz, 3H), 1.54 (m, 2H), 2.57 (s, 3H), 2.67 (t, J = 7.6 Hz, 2H), 5.34 (s, 2H), 6.68 (d, J = 9.0 Hz, 1H), 7.69 (d, J = 8.6 Hz, 2H), 7.77 (d, J = 9.0 Hz, 1H), 7.86 (d, J = 8.6 Hz, 2H), 7.98 (d, J = 8.2 Hz, 2H), 8.29 (d, J = 8.6 Hz, 2H), 12.88 (s, 1H). MS (m/z): 475 (M − 1). |

| Ex. # | Method # | Chemical name | Structure | Physical data |
|---|---|---|---|---|
| 46 | Method of Example 2 | 1-(2-Hydroxy-3-propyl-4-{3-[3-(2H-tetrazol-5-yl)-benzenesulfinyl]-benzyloxy}-phenyl)-ethanone | 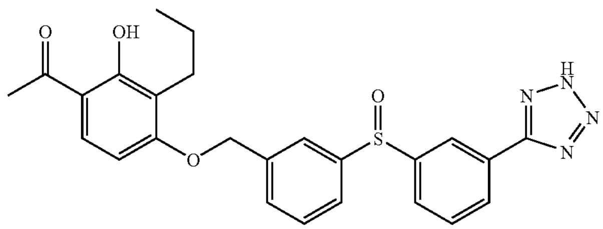 | ¹H NMR (400 MHz, acetone-d₆) δ 0.89 (t, J = 7.4 Hz, 3H), 1.54 (m, 2H), 2.57 (s, 3H), 2.67 (t, J = 7.4 Hz, 2H), 5.33 (s, 2H), 6.68 (d, J = 9.0 Hz, 1H), 7.68 (d, J = 7.8 Hz, 2H), 7.77 (d, J = 8.2 Hz, 2H), 7.88 (d, J = 8.2 Hz, 2H), 7.94 (d, J = 8.6 Hz, 1H), 8.25 (d, J = 8.2 Hz, 1H), 8.50 (s, 1H), 12.88 (s, 1H). MS (m/z): 475 (M − 1). |
| 47 | Method of Example 2 | 1-(2-Hydroxy-3-propyl-4-{3-[2-(1H-tetrazol-5-yl)-benzenesulfinyl]-benzyloxy}-phenyl)-ethanone | 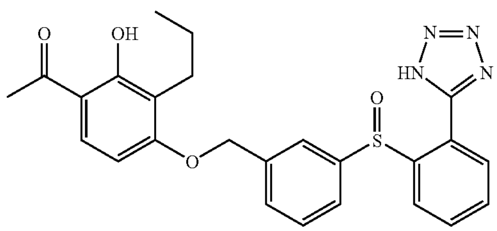 | ¹H NMR (400 MHz, acetone-d₆) δ 0.88 (t, J = 7.4 Hz, 3H), 1.47-1.57 (m, 2H), 2.57 (s, 3H), 5.34 (s, 2H), 6.67 (d, J = 9.0, 1H), 7.63 (m, 2H), 7.75 (m, 2H), 7.81 (d, J = 7.0, 1H), 7.90 (d, J = 8.2 Hz, 1H), 7.94 (s, 1H), 8.24 (d, J = 7.8 Hz, 1H), 8.49 (s, 1H), 12.87 (s, 1H). MS (m/z): 475 (M − 1). |

EXAMPLE 48

Synthesis of 1-(2-hydroxy-3-propyl-4-{3-[4-(2H-tetrazol-5-yl)-pyridin-2-ylsulfanyl]-benzyloxy}-phenyl)-ethanone

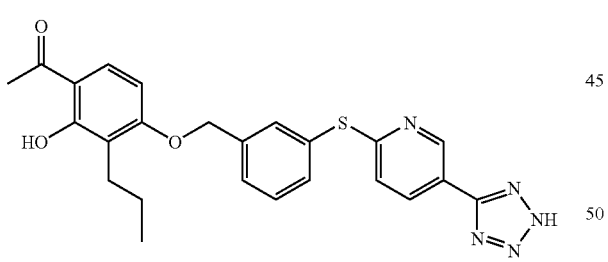

Employing the procedure essentially as described in Example 1 using 6-[3-(4-acetyl-3-hydroxy-2-propyl-phenoxymethyl)-phenylsulfanyl]-nicotinonitrile (430 mg, 1.03 mmol), sodium azide (668 mg, 10.3 mmol), and triethylamine hydrochloride (1.41 g, 10.3 mmol) purify by reverse phase chromatography eluting with methanol: acetic acid: water, the title compound is obtained as a white solid (77 mg, 16%): ¹H NMR (CD₃CN) δ 0.83 (t, 3H), 1.48 (sextuplet, 2H), 2.53 (s, 3H), 2.60 (t, 2H), 5.24 (s, 2H), 6.62 (d, 1H), 7.11 (d, 1H), 7.56 (m, 3H), 7.71 (m, 2H), 8.11 (dd, 1H), 8.96 (dd, 1H), 12.82 (bs, 1H); MS (esi negative) m/z 460 (m−1).

EXAMPLE 49

Synthesis of 1-(2-hydroxy-3-propyl-4-{3-[4-(2H-tetrazol-5-yl)-pyridin-2-ylsulfanyl]-benzyloxy}-phenyl)-ethanone

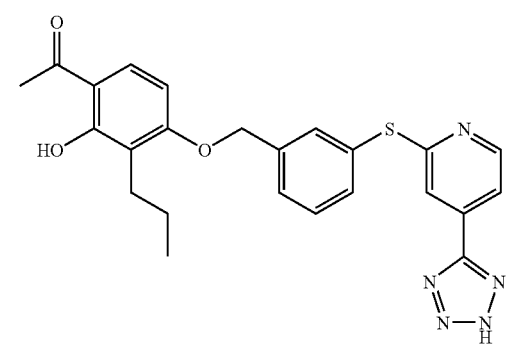

Employing the procedure essentially as described in Example 1 using 2-[3-(4-acetyl-3-hydroxy-2-propyl-phenoxymethyl)-phenylsulfanyl]-isonicotinonitrile (380 mg, 0.908 mmol), sodium azide (590 mg, 9.08 mmol), and triethylamine hydrochloride (1.25 g, 9.08 mmol), the title compound is obtained as a white solid (261 mg, 62%): ¹H NMR (DMSO-d₆) δ 0.760 (t, 3H), 1.39 (sextuplet, 2H), 2.52 (t, 2H), 2.56 (s, 3H), 5.32 (s, 2H), 6.71 (d, 1H), 7.59 (m, 4H), 7.73 (m, 2H), 7.79 (d, 1H), 8.64 (d, 1H), 12.82 (s, 1H); MS (esi negative) m/z 460 (m−1).

Preparation 100

Synthesis of 2-iodo-benzene-1,3-diol

Add sodium bicarbonate (27.9 g, 333 mmol) to a solution of benzene-1,3-diol (33.0 g, 300 mmol), and iodine (81.5 g, 321 mmol) in water (225 mL) chilled to 0° C. and stir. Warm the solution to ambient temperature gradually over 1 hour. Extract with diethyl ether, combine organic layers, dry with sodium sulfate, filter and concentrate under reduced pressure to yield a white solid. Triturate the solid in chloroform (100 mL) chilled to −10° C. After 30 minutes, filter the precipitate, washing with cold chloroform to yield the title compound as a white solid (49.0 g, 69%): $^1$H NMR (DMSO-$d_6$) δ 6.33 (d, 2H), 6.93 (t, 1H), 10.03 (s, 2H).

Preparation 101

Synthesis of 1,3-bis-benzyloxy-2-iodo-benzene

Add benzyl bromide (7.97 g, 46.6 mmol) to a solution of 2-iodo-benzene-1,3-diol (5.00 g, 21.2 mmol) and cesium carbonate (15.2 g, 46.6 mmol) in dimethylformamide (200 mL) and stir. After 18 hours, concentrate under reduced pressure. Add water (500 mL) and stir. After 1 hour, filter the resulting precipitate washing with water and hexanes to yield the title compound as an off-white solid (6.30 g, 71%): $^1$H NMR (CDCl$_3$) δ 5.18 (s, 4H), 6.55 (d, 2H), 7.19 (t, 1H), 7.29-7.53 (m, 10H).

Preparation 102

Synthesis of 1,3-bis-benzyloxy-2-trifluoromethyl-benzene

Add difluoro-fluorosulfonyl-acetic acid methyl ester (15.0 g, 78.1 mmol) to a solution of 1,3-bis-benzyloxy-2-iodo-benzene (6.50 g, 15.6 mmol), hexamethylphosphoramide (13.99 g, 78.1 mmol), and copper iodide (3.57 g, 18.7 mmol) in dimethylformamide (50 mL) and stir. Heat reaction to 80° C. After 18 hours, cool to ambient temperature. Add saturated aqueous ammonium chloride (250 mL) and extract with ether. Combine organic layers, and wash with saturated aqueous sodium bicarbonate, brine, dry with magnesium sulfate, filter and concentrate under reduced pressure to give a residue. Purify the residue by flash chromatography eluting with 20% ethyl acetate:hexanes to yield the title compound as a clear oil (4.60 g, 82%): $^1$H NMR (CDCl$_3$) δ 5.14 (s, 4H), 6.67 (d, 2H), 7.29-7.46 (m, 11H).

Preparation 103

Synthesis of 1,3-bis-benzyloxy-4-bromo-2-trifluoromethyl-benzene

Add N-bromosuccinimide (4.67 g, 26.23 mmol) to a solution of 1,3-bis-benzyloxy-2-trifluoromethyl-benzene (9.40 g, 26.2 mmol) in dimethylformamide (100 mL) and stir. After 18 hours add water and extract with diethyl ether. Combine organic layers, dry with sodium sulfate, filter and concentrate under reduced pressure to yield the title compound as an orange oil (11.20 g, 98%): $^1$H NMR (CD$_3$CN) δ 4.97 (2, 2H), 5.18 (s, 2H), 6.99 (d, 1H), 7.33-7.55 (m, 10H), 7.79 (d, 1H).

Preparation 104

Synthesis of 1-(2,4-bis-benzyloxy-3-trifluoromethyl-phenyl)-ethanone

Add tetrakis(triphenylphosphine)palladium (2.93 g, 2.54 mmol) to a solution of 1,3-bis-benzyloxy-4-bromo-2-trifluoromethyl-benzene (11.10 g, 25.4 mmol) and tributyl-(1-ethoxy-vinyl)-stannane (10.08 g, 27.92 mmol) in dioxane (250 mL) and stir. Purge reaction vessel with argon. Heat to 100° C. After 6 hours, cool to ambient temperature and concentrate under reduced pressure. Add 2N aqueous hydrochloric acid (50 mL), and tetrahydrofuran (200 mL) and stir. After 30 minutes add water and extract with ethyl acetate. Combine organic layers, dry with sodium sulfate, filter and concentrate under reduced pressure to yield a residue. Purify the residue by flash chromatography eluting with a gradient of 0-20% ethyl acetate:hexanes to yield the title compound as a clear oil (6.10 g, 60%): $^1$H NMR (CD$_3$CN) δ 2.48 (s, 3H), 4.89 (s, 2H), 5.25 (s, 2H), 7.08 (d, 1H), 7.33-7.48 (m, 10H), 7.83 (d, 1H).

Preparation 105

Synthesis of 1-(2,4-dihydroxy-3-trifluoromethyl-phenyl)-ethanone

Add 20% palladium hydroxide on carbon (11.0 g, 15 mmol) to a solution of 1-(2,4-bis-benzyloxy-3-trifluoromethyl-phenyl)-ethanone (6.00 g, 15 mmol) in ethanol (75 mL) and cyclohexene (75 mL) and stir. Purge the reaction vessel with argon. Heat to reflux. After 18 hours, cool to ambient temperature, filter and concentrate under reduced pressure to yield the title compound as a grey solid (3.00 g, 91%): $^1$H NMR (CD$_3$CN) δ 2.55 (s, 3H), 6.51 (d, 1H), 7.88 (d, 1H), 13.91 (bs, 1H).

EXAMPLE 50

Synthesis of 1-(2-hydroxy-3-propyl-4-{3-[3-(2H-tetrazol-5-yl)-benzenesulfinyl]-benzyloxy}-phenyl)-ethanone sodium salt (phenol)

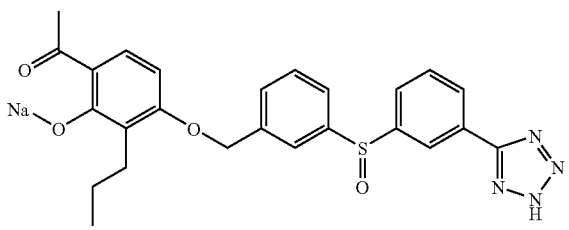

Add sodium hydride (12.1 mg, 0.504 mmol, 95%, dry, 1.00 mmol, Aldrich Chemical Co.) to a solution of 1-(2-hydroxy-3-propyl-4-{3-[3-(2H-tetrazol-5-yl)-benzenesulfinyl]-benzyloxy}-phenyl)-ethanone (0.240 g, 0.504 mmol) in tetrahydrofuran (0.2 M). Evaporate solvent and triturate with diethyl ether. Filter to collect the title compound as the resulting precipitate (180 mg, 0.361 mmol, 72%): $^1$H NMR (400 MHz, DMSO-$d_6$) δ 0.84 (t, J=7.2 Hz, 3H), 1.33-1.39 (m, 2H), 2.45-2.47 (m, 2H), 2.50 (s, 3H), 5.07 (s, 2H), 5.77 (d, J=9.4 Hz, 1H), 7.27 (d, J=9.0 Hz, 1H), 7.51-7.57 (m, 4H), 7.66 (d, J=7.0 Hz, 1H), 7.82 (s, 1H), 8.07 (d, J=7.0 Hz, 1H), 8.26 (s, 1H). MS (m/z): 475 (M−1).

EXAMPLE 51

Synthesis of 1-(2-hydroxy-3-propyl-4-{3-[3-(2Na-tetrazol-5-yl)-benzenesulfinyl]-benzyloxy}-phenyl)-ethanone sodium salt (tetrazole)

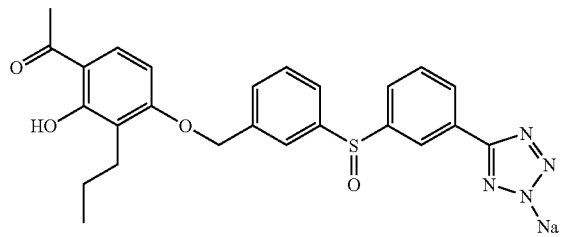

Add sodium methoxide (1.00 mmol, 0.5 M solution in methanol) to a solution of 1-(2-hydroxy-3-propyl-4-{3-[3-(2H-tetrazol-5-yl)-benzenesulfinyl]-benzyloxy}-phenyl)-ethanone (0.150 g, 0.315 mmol), and stir for 30 min. Evaporate solvent. Add 1:10 tetrahydrofuran/ether and sonicate the residue. Filter and collect the solid product. The title compound was obtained (0.150 g, 0.310 mmol, 96%): $^1$H NMR (400 MHz, DMSO-$d_6$) δ 0.86 (t, J=7.4 Hz, 3H), 1.46 (q, J=9.9 Hz, 2H), 2.55 (s, 3H), 2.57 (m, 2H), 5.32 (s, 2H), 6.65 (d, J=8.2 Hz, 1H), 7.53 (s, 1H), 7.56-7.61 (m, 4H), 7.71 (d, J=7.4 Hz, 1H), 7.75 (d, J=9.4 Hz, 1H), 7.84 (s, 1H), 8.06 (m, 1H), 8.24 (m, 1H), 12.85 (s, 1H). MS (m/z): 475 (M−1).

EXAMPLE 52

Synthesis of 6-[4-(4-acetyl-3-hydroxy-2-propyl-phenoxymethyl)-phenoxy]-nicotinic acid

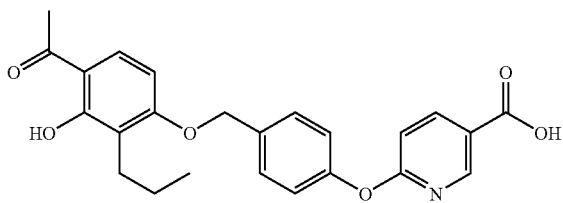

Mix 6-[4-(4-acetyl-3-hydroxy-2-propyl-phenoxymethyl)-phenoxy]-nicotinonitrile (,0.14 g, 0.34 mmol), powdered potassium hydroxide (0.69 g, 12.20 mmol), isopropyl alcohol (1.5 mL) and water (1.5 mL). Heat to 130° C. for 8 hrs. Allow to cool to ambient temperature. Pour into water (20 mL) and acidify to pH 1 with hydrochloric acid (37% in water, 1 mL). Extract with ethyl acetate (3×30 mL). Combine the organic extracts, dry over magnesium sulfate, filter and concentrate under reduced pressure to obtain a residue. Purification using 5% isopropyl alcohol/chloroformchloroform to 10% isopropyl alcohol/chloroformchloroform as gradient eluent gives the title compound (0.02 g, 17%): MS (m/z): 420.1 (M−1). $^1$H NMR (acetone-$d_6$) 12.94 (s, 1H), 8.77 (s, 1H), 8.40 (dd, J=2.4 Hz, 8.4 Hz, 1H), 7.84 (d, J=9.0 Hz, 1H), 7.62 (d, J=8.4 Hz, 2H), 7.30 (d, J=8.4 Hz, 2H), 7.15 (d, J=8.4 Hz, 1H), 6.79 (d, J=9.2 Hz, 1H), 5.34 (s, 2H), 2.73 (t, J=7.5 Hz, 2H), 2.63 (s, 3H), 1.66-1.56 (m, 2H), 0.96 (t, J=7.5 Hz, 3H).

EXAMPLE 53

Synthesis of 6-[3-(3-hydroxy-2-methyl-4-propionyl-phenoxymethyl)-phenoxy]-nicotinic acid

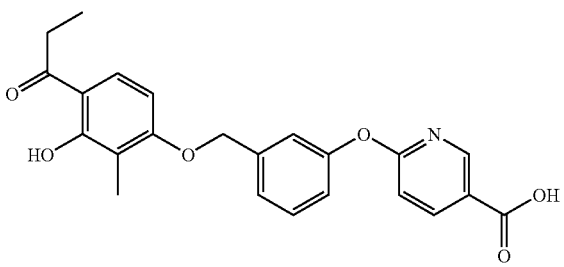

Dissolve 6-[3-(3-hydroxy-2-methyl-4-propionyl-phenoxymethyl)-phenoxy]-nicotinic acid methyl ester (0.10 g, 0.24 mmol) in tetrahydrofuran (2 mL). Add lithium hydroxide (0.007 g, 0.29 mmol) and water (0.5 mL). Stir at ambient temperature for 2 hrs. Add 1 N hydrochloric acid (5 mL) and extract with ethyl acetate (3×10 mL). Combine the organic extracts, dry over magnesium sulfate, filter and concentrate under reduced pressure to obtain a residue. Purification using 5% isopropyl alcohol/chloroformchloroform to 10% isopropyl alcohol/chloroform as gradient eluent gives the title compound (0.06 g, 58%): MS (m/z): 406.1 (M−1). $^1$H NMR (acetone-$d_6$) 13.00 (s, 1H), 8.76 (s, 1H), 8.40 (dd, J=1.7 Hz, 8.4 Hz, 1H), 7.86 (d, J=9.2 Hz, 1H), 7.54 (t, J=8.0 Hz, 1H), 7.44 (d, J=7.6 Hz, 1H), 7.38 (s, 1H), 7.22 (d, J=8.0 Hz, 1H), 7.15 (d, J=8.5 Hz, 1H), 6.76 (d, J=9.2 Hz, 1H), 5.36 (s, 2H), 3.09 (q, J=7.2 Hz, 2H), 2.14 (s, 3H), 1.20 (t, J=7.2 Hz, 3H).

The following examples are prepared essentially as described for Example 52 or 53.

| Ex. # | Method | Chemical name | Structure | Physical data |
|---|---|---|---|---|
| 54 | Method of Example 52 | 2-[3-(4-Acetyl-3-hydroxy-2-propyl-phenoxymethyl)-phenoxy]-isonicotinic acid | 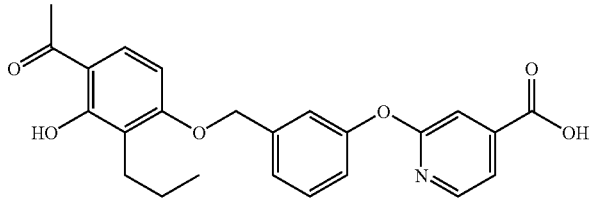 | MS (m/z): 420.1 (M − 1). $^1$H NMR (DMSO-$d_6$) 13.82 (bs, 1H), 12.85 (s, 1H), 8.35 (d, J = 5.1 Hz, 1H), 7.83 (d, J = 9.1 Hz, 1H), 7.57 (d, J = 5.1 Hz, 1H), 7.49 (t, J = 7.9 Hz, 1H), 7.38 (s, 1H), 7.33 (d, J = 7.6 Hz, 1H), 7.24 (s, 1H), 7.16 (d, J = 7.9 Hz, 1H), 6.73 (d, J = 9.1 Hz, 1H), 5.30 (s, 2H), 2.59 (s, 3H), 2.57 (t, J = 7.6 Hz, 2H), 1.49-1.40 (m, 2H), 0.81 (t, J = 7.6 Hz, 3H). |

-continued

| Ex. # | Method | Chemical name | Structure | Physical data |
|---|---|---|---|---|
| 55 | Method of Example 53 | 6-[3-(4-Acetyl-3-hydroxy-2-trifluoromethyl-phenoxymethyl)-phenoxy]-nicotinic acid | 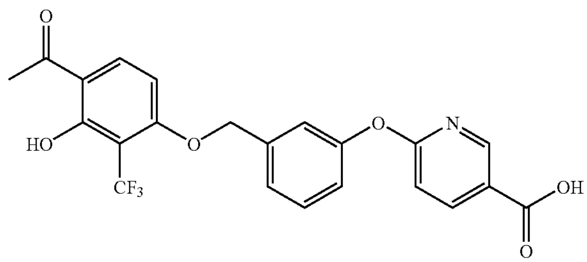 | LC-MS (m/e): 446 (M − 1); $^1$H NMR (DMSO-d$_6$) δ 13.80 (1H, s), 8.68 (1H, d), 8.32 (1H, dd), 8.23 (1H, d), 7.51 (1H, dd), 7.35 (1H, d), 7.27 (1H, m), 7.18 (2H, m), 6.84 (1H, d), 5.43 (2H, s), 2.66 (3H, s). |
| 56 | Method of Example 53 | 3-[3-(4-Acetyl-3-hydroxy-2-propyl-phenoxymethyl)-benzenesulfonyl]-benzoic acid | 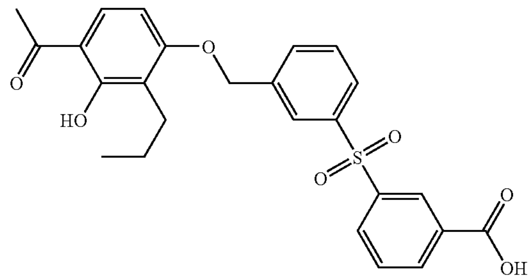 | $^1$H NMR (400 MHz, acetone-d$_6$) δ 0.93 (t, J = 7.4 Hz, 3H), 1.56 (m, 2H), 2.58 (s, 3H), 2.68 (t, J = 7.4 Hz, 2H), 5.40 (s, 2H), 6.70 (d, J = 9.0 Hz, 1H), 7.18-7.25 (m, 2H), 7.77-7.84 (m, 2H), 8.04 (d, J = 7.8 Hz, 1H), 8.16 (s, 1H), 8.23 (d, J = 6.6 Hz, 1H), 8.30 (d, J = 9.0 Hz, 1H), 8.58 (s, 1H), 12.9 (s, 1H). MS (m/z): 467 (M − 1). |
| 57 | Method for Example 53 | 3-[4-(4-Acetyl-3-hydroxy-2-propyl-phenoxymethyl)-benzenesulfonyl]-benzoic acid | 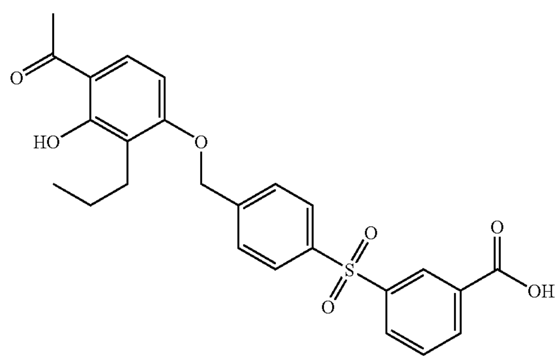 | $^1$H NMR (400 MHz, acetone-d$_6$) δ 0.91 (t, J = 7.4 Hz, 3H), 1.55 (m, 2H), 2.56 (s, 3H), 2.69 (t, J = 7.6 Hz, 2H), 5.38 (s, 2H), 6.65 (d, J = 9.0 Hz, 1H), 7.18 (m, 2H), 7.73 (m, 2H), 8.10 (d, J = 7.0 Hz, 2H), 8.28 (t, J = 9.2 Hz, 2H), 8.60 (s, 1H), 12.89 (s, 1H). MS (m/z): 467 (M − 1). |
| 58 | Method for Example 53 | 4-[4-(4-Acetyl-3-hydroxy-2-propyl-phenoxymethyl)-benzenesulfonyl]-benzoic acid | 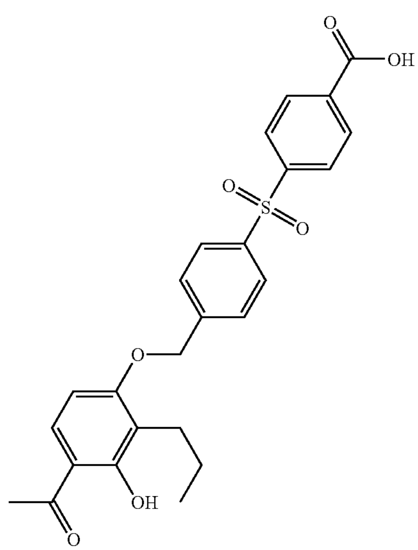 | $^1$H NMR (400 MHz, acetone-d$_6$) δ 0.92 (t, J = 7.4 Hz, 3H), 1.56 (m, 2H), 2.57 (s, 3H), 2.69 (t, J = 7.4 Hz, 2H), 5.40 (s, 2H), 6.67 (d, J 9.0 Hz, 1H), 7.75 (m, 3H), 8.09 (d, J = 7.0 Hz, 2H), 8.15 (d, J = 8.2 Hz, 2H), 8.23 (d, J = 8.6 Hz, 2H), 12.89 (s, 1H). MS (m/z): 467 (M − 1). |

EXAMPLE 59

Synthesis of 2-[3-(4-acetyl-2-carboxy-3-hydroxy-phenoxymethyl)-phenoxy]-isonicotinic acid

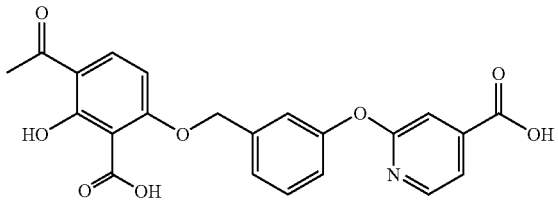

The title compound is prepared essentially as described for 4-[4-(4-acetyl-3-hydroxy-2-propyl-benzyloxy)-benzene-sulfinyl]-benzoic acid (Example 57) employing 2-[3-(4-acetyl-3-hydroxy-2-trifluoromethyl-phenoxymethyl)-phenoxy]-isonicotinonitrile. Heat in microwave reactor for 35 min. at 150° C. (33%). LC-MS (m/e): 422 (M−1); $^1$H NMR (DMSO-d$_6$) δ 8.34 (1H, d), 8.00 (1H, d), 7.57 (1H, dd), 7.48 (1H, dd), 7.39 (1H, s), 7.31 (1H, d), 7.25 (1H, s), 7.15 (1H, m), 6.80 (1H, d), 5.35 (2H, s), 2.52 (3H, s)

Preparation 106

Synthesis of dimethyl-thiocarbamic acid S-(4-acetyl-3-hydroxy-2-propyl-phenyl) ester Stir a mixture of 1-(2,4-dihydroxy-3-propyl-phenyl)-ethanone (2 g, 10.3 mmol), triethylamine (1.6 mL 11.3 mmol), and dichloromethane (40 mL) at room temperature. Add dimethylthiocarbamoyl chloride (1.27 g, 10.3 mmol) and stir at room temperature overnight. Wash the mixture with 1M hydrochloric acid (25 mL), dry over magnesium sulfate, filter and concentrate. Purify the residue via silica chromatography eluting with hexanes to 7:3 hexanes:ethyl acetate to afford dimethyl-thiocarbamic acid O-(4-acetyl-3-hydroxy-2-propyl-phenyl) ester (1.2 g, 41%) as a light yellow solid. Stir the yellow solid in tetradecane (10 mL) at 250° C. for an hour and purify by silica chromatography eluting with hexanes to 6:4 hexanes:ethyl acetate to give the title compound (1.08 g, 90%) as a white solid. LCMS (m/z) 280 m−1.

Preparation 107

Synthesis of 1-(2-hydroxy-4-mercapto-3-propyl-phenyl)-ethanone

Reflux a stirred mixture of dimethyl-thiocarbamic acid S-(4-acetyl-3-hydroxy-2-propyl-phenyl) ester (1.08 g, 3.84 mmol), potassium hydroxide (1.1 g, 19.2 mmol), ethanol (25 mL), and water (10 mL) for 2 hours. Cool the reaction in an ice/water bath and adjust the pH to 2 with aqueous 5N hydrochloric acid. Extract the mixture with ethyl acetate (3×50 mL). Combine the extracts and wash with water (50 mL) and brine (50 mL) and dry over magnesium sulfate, filter, and concentrate to afford the title compound (0.76 g, 94%) as a brown oil which solidifies on standing. LCMS (m/z) 211 m−1.

Preparation 108

Synthesis of 2-fluoro-3-methoxy-phenol

A mixture of 2-fluoroanisole (1.8 ml, 15.85 mmol), pentamethyldiethyenetriamine (3.6 mL, 17.45 mmol) and tetrahydrofuran (10 mL) is stirred at −78° C. A 2.5 M solution of n-butyllithium in hexanes (7 ml, 17.45 mmol) is added dropwise and the resulting solution is stirred at −78° C. 2 hr. Trimethylborate (2 mL, 17.45 mmol) is added and the reaction is warmed to room temperature and stirred 1 hr. Acetic acid (1.4 ml, 23.8 mmol) is added followed by an aqueous 30% solution of hydrogen peroxide (1.8 mL, 17.45 mmol) and the resulting mixture is stirred rapidly 18 hr at room temperature. The reaction mixture is diluted with water and extracted with ethyl acetate (3×50 mL). The combined extracts are dried over magnesium sulfate, filtered and concentrated to about 10 mL volume. The resulting mixture is purified via silica chromatography eluting with hexanes to 8:1 hexanes:ethyl acetate to give the title compound (1.65 g, 73%) as a colorless oil. MS ES 141 m−1.

Preparation 109

Synthesis of 1-(3-fluoro-2,4-dihydroxy-phenyl)-ethanone

A solution of 2-fluoro-3-methoxy-phenol (0.5 g, 3.53 mmol) and dichloromethane is stirred at −78° C. A 1M solution of boron tribromide in dichloromethane (3.9 mL, 3.9 mmol) is added slowly and the mixture is stirred 10 min cold, then warmed to 0° C. and stirred 1 hr. The reaction is quenched with ice and stirred at room temperature overnight. The product is extracted with ethyl acetate (2×50 mL), dried over magnesium sulfate, filtered, and concentrated. The resulting residue is combined with boron trifluoride diethyl etherate (1.3 mL, 10.3 mmol) and acetic acid (0.2 mL, 3.28 mmol) and heated to reflux 8 hr. The mixture is cooled to room temperature, diluted with water (50 mL), and extracted with ethyl acetate (3×50 mL). The combined extracts are dried over magnesium sulfate, filtered and concentrated to about 10 mL volume. The resulting mixture is diluted with hexanes (50 mL), cooled to 0° C., and filtered to give the title compound (310 mg, 58%) as a tan solid. MS ES171 m+1.

Preparation 110

Synthesis of 1-(3-chloro-2,4-dihydroxy-phenyl)-ethanone

A solution of 2,4,-dihydroxyacetophenone (6 g, 39.4 mmol), aqueous 1M sodium hydroxide (41.4 mL, 41.4 mmol) and water (200 mL) is stirred at room temperature. An aqueous 1.6M solution of sodium hypochlorite (32 mL) is added over a 1 hr period. The resulting dark brown solution is stirred 18 hr at room temperature. The reaction mixture is adjusted to a pH of 2-3 with concentrated aqueous hydrochloric acid. The resulting suspension is filtered and washed with water (4×100 mL). The filtered solid was dried under vacuum at 45° C. for 2.5 days to give the title compound (4.8 g, 65%) as a brown solid. LCMS 1 187 m+.

Preparation 111

Synthesis of 1-(3-chloro-2,4-dihydroxy-phenyl)-propan-1-one

The title compound was prepared in a similar manner to 1-(3-chloro-2,4-dihydroxy-phenyl)-ethanone (Preparation 111) employing 2,4-dihydroxypropiophenone to give 4.5 g, 37% of an off-white solid. LCMS1 201 m+.

Preparation 112

Synthesis of 1-[2-hydroxy-4-(4-nitro-benzyloxy)-3-propyl-phenyl]-ethanone

To 2',4'-dihydroxy-3'-propyl acetophenone (3.0 g, 15.4 mmol) and 4-nitrobenzyl bromide (3.6 g, 17 mmol) in acetone (62 mL) is added $K_2CO_3$ (3.2 g, 23 mmol). The reaction mixture is refluxed for 1 h and cooled to room temperature. The precipitate is filtered, washed with water (5×70 mL), and dried to give the title compound (4.8 g, 94%). LC-MS (m/z): 328 (M−1).

Preparation 113

Synthesis of 1-[4-(4-amino-benzyloxy)-2-hydroxy-3-propyl-phenyl]-ethanone

To 1-[2-Hydroxy-4-(4-nitro-benzyloxy)-3-propyl-phenyl]-ethanone (1.0 g, 3.0 mmol) in tetrahydrofuran (13 mL) is added concentrated hydrochloric acid (2.7 mL) and stannous chloride dihydrate (2.2 g, 9.9 mmol). The reaction mixture is stirred at room temperature overnight. The reaction mixture is quenched into saturated aqueous $NH_4Cl$ (100 mL). The resulting emulsion is filtered and the filtrate extracted with ethyl acetate (3×100 mL). The combined organic layers are washed with brine, dried over sodium sulfatesodium sulfate, and concentrated to provide the title compound in crude form (980 mg,). LC-MS (m/z): 298 (M−1).

Preparation 114

Synthesis of 1-(2,6-dihydroxy-biphenyl-3-yl)-ethanone

To a solution of 1-(2,4-dihydroxy-3-iodo-phenyl)-ethanone (1.0 g, 3.59 mmol; 581938, may be prepared as described in G. Batu and R. Stevenson, *J. Org. Chem.* 1979, 44, 3948) in tetrahydrofuran/water (15 mL/3 mL) at room temperature is added phenyl boronic acid (0.877 g, 7.19 mmol), Pd(dppf)$_2$Cl$_2$ (0.088 g, 0.107 mmol), and cesium hydroxide monohydrate (1.81 g, 10.8 mmol). After stirring for 15 hours, the mixture is filtered through a pad of Celite®, washing with ethyl acetate. The residue is diluted with 30 mL of 1N hydrochloric acid and extracted with ethyl acetate. The combined organic phases are washed with brine; dried over magnesium sulfate; filtered and concentrated under reduced pressure. The resulting residue is purified by flash chromatography, eluting with 30% ethyl acetate/hexanes to give the title compound as a colorless solid: MS (m/z) 228(M+); $^1$H NMR (DMSO-d$_6$) δ 13.1 (s, 1H), 10.6 (bs, 1H), 7.81 (d, J=8.8 Hz, 1H), 7.41-7.28 (m, 5H), 6.61 (d, J=8.8 Hz, 1H), 2.58 (s, 3H); R$_f$=0.58 in 40% ethyl acetate/hexanes.

Preparation 115

Synthesis of 1-(4'-fluoro-2,6-dihydroxy-biphenyl-3-yl)-ethanone

The title compound is prepared essentially as described in Preparation 119 using 4-fluorophenylboronic acid: mass spectrum (m/e): 245(M−1); $^1$H NMR (acetone-d$_6$) δ 13.2 (s, 1H), 7.82 (d, J=8.4 Hz, 1H), 7.44-7.40 (m, 2H), 7.18-7.13 (m, 2H), 6.61 (d J=8.8 Hz, 1H), 2.60 (s, 3H); R$_f$=0.40 in 40% ethyl acetate/hexanes.

Preparation 116

Synthesis of (6-bromo-pyridin-2-yl)-methanol

Add n-butyl lithium (16.2 mL, 2.5 M in hexanes, 40.5 mmol) dropwise to a solution of 2,6-dibromopyridine (8.00 g, 33.8 mmol) in tetrahydrofuran (100 mL) at −78° C. Stir 30 minutes then add dimethylformamide (12.3 g, 169 mmol) via syringe. Allow solution to warm to ambient temperature then pour it into a solution of sodium borohydride (17.85 g, 338 mmol) in ethanol (50 mL) at −10° C. After 10 minutes, remove the cooling bath. After 1 hour at ambient temperature, add water and 1N hydrochloric acid (gas evolution), then add saturated sodium bicarbonate solution until the mixture is neutralized. Extract the aqueous phase with ethyl acetate, dry over sodium sulfate, filter and concentrate under reduced pressure. Dissolve the residue in diethyl ether and add an excess of hydrogen chloride (2N in diethyl ether). Decant the organic phase and add saturated sodium bicarbonate solution to the residue. Extract with ethyl acetate (3×), dry over sodium sulfate, filter and concentrate under reduced pressure to afford the title compound as a brown oil (2.73 g, 14.5 mmol): MS (m/z): 189 (M+1).

Preparation 117

Synthesis of 1-[4-(6-bromo-pyridin-2-ylmethoxy)-2-hydroxy-3-propyl-phenyl]-ethanone Combine (6-bromo-pyridin-2-yl)-methanol (1.00 g, 5.32 mmol), 1-(2,4-dihydroxy-3-propyl-phenyl)-ethanone (1.033 g, 5.32 mmol) and tri-n-butylphosphine (1.46 mL, 5.85 mmol, Aldrich Chemical Co.) in tetrahydrofuran (5.3 mL), add 1,1'-(azodicarbonyl)dipiperidine (1.48 g, 5.85 mmol, Aldrich Chemical Co.). After 12 hours at ambient temperature, add diethyl ether (white precipitate forms) and filter, collect liquid and remove solvents under reduced pressure. Purify residue by flash chromatography to obtain the title compound as a white solid (854 mg, 2.35 mmol): MS (m/z): 286 (M−Br+1).

The following compound is prepared essentially by the method of Preparation 117.

| Prep. No. | Chemical name | Structure | Physical data |
|---|---|---|---|
| 118 | 1-[4-(2-Chloro-pyridin-4-ylmethoxy)-2-hydroxy-3-propyl-phenyl]-ethanone | 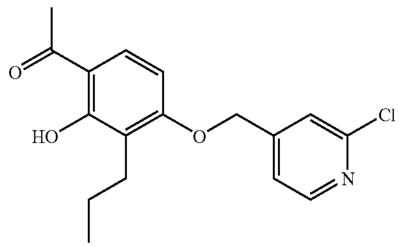 | MS (m/z): 318 (M − 1). |

EXAMPLE 60

Synthesis of 3-[6-(4-acetyl-3-hydroxy-2-propyl-phenoxymethyl)-pyridin-2-ylsulfanyl]-benzoic acid

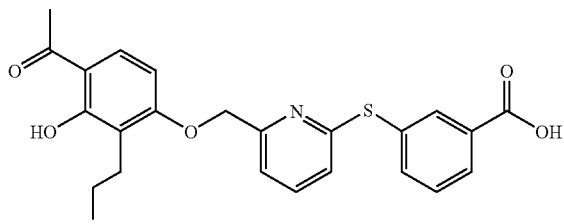

To a solution of 3-mercaptobenzoic acid (361 mg, 2.35 mmol) in dimethylformamide (15 mL) add sodium hydride (23 mg, 9.38 mmol) at 0° C., stir 10 min. Add 1-[4-(6-bromo-pyridin-2-ylmethoxy)-2-hydroxy-3-propyl-phenyl]-ethanone (854 mg, 2.35 mmol), heat to 100° C. for 6 hours. Cool to ambient temperature and add diethyl ether, collect the resulting red precipitate by filtration (290 mg). Purify by the residue by preparative LC (inject 110 mg) to yield the title compound as a white solid (50 mg, 0.12 mmol): $^1$H NMR (DMSO-$d_6$) δ 0.88 (t, 3H), 1.50 (q, 2H), 2.55 (s, 3H), 2.61 (m, 2H), 5.25 (s, 2H), 6.65 (d, 1H), 6.97 (d, 1H), 7.26 (d, 1H), 7.62 (t, 1H), 7.76 (m, 1H), 7.83 (m, 1H), 8.02 (m, 1H), 8.07 (m, 1H), 12.85 (s, 1H), 13.25 (br s, 1H); MS (m/z): 436 (M−1).

The following compound is prepared essentially by the method of Example 60.

Preparation 119

Synthesis of 3-(5-hydroxymethyl-pyridin-3-ylsulfanyl)-benzoic acid methyl ester

Dissolve 3-bromo-5-hydroxymethyl-pyridinium chloride$^i$ [Kelly, T. R., Howard, H. R., Koe, K., Sarges, R. *J. Med. Chem.* 1985, 28, 1368-1371] (1.00 g, 4.45 mmol) in saturated aqueous sodium bicarbonate, extract three times with ethyl acetate, dry combined organic phases over sodium sulfate, condense to afford (5-bromo-pyridin-3-yl)-methanol. Employing the procedure of general method 1 using (5-bromo-pyridin-3-yl)-methanol (832 mg) and 3-mercaptobenzoic acid methyl ester (1.50 g, 8.91 mmol). Purify by SCX column, elute with dichloromethane, then 1:1 dichloromethane/methanol then 1:1 dichloromethane/methanol, 10% ammonia, compound elutes in the ammonia, to yield the title compound as a dark brown oil (380 mg, 1.38 mmol): MS (m/z): 276 (M+1).

The following compound is prepared essentially by the method of Preparation 119.

| Ex. | Chemical name | Structure | Physical data |
|---|---|---|---|
| 61 | 3-[4-(4-Acetyl-3-hydroxy-2-propyl-phenoxymethyl)-pyridin-2-ylsulfanyl]-benzoic acid | 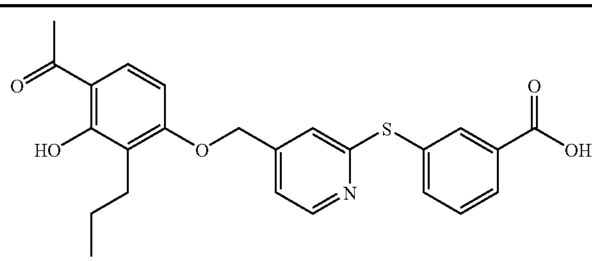 | $^1$H NMR (DMSO-$d_6$) δ 0.77 (t, 3H), 1.36 (m, 2H), 2.44 (m, 2H), 2.57 (s, 3H), 5.25 (s, 2H), 6.58 (d, 1H), 7.02 (m, 1H), 7.20 (m, 1H), 7.59 (t, 1H), 7.79 (m, 2H), 8.04 (m, 2H), 8.44 (d, 1H), 12.83 (s, 1H), 13.24 (br s, 1H); MS (m/z): 438 (M + 1). |

| Prep. No. | Chemical name | Structure | Physical data |
|---|---|---|---|
| 120 | 3-(6-Hydroxymethyl-pyridin-3-ylsulfanyl)-benzoic acid methyl ester | 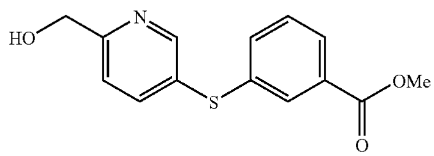 | MS (m/z): 276 (M + 1). |

Preparation 121

Synthesis of 3-[5-(4-acetyl-3-hydroxy-2-propyl-phenoxymethyl)-pyridin-3-ylsulfanyl]-benzoic acid methyl ester Using the procedure essentially of Preparation 117 using 3-(5-hydroxymethyl-pyridin-3-ylsulfanyl)-benzoic acid methyl ester (370 mg, 1.34 mmol), 1-(2,4-dihydroxy-3-propyl-phenyl)-ethanone (261 mg, 1.34 mmol) provides the title compound as colorless oil (379 mg, 0.84 mmol): MS (m/z): 452 (M+1).

The following compounds are prepared essentially by the method of Preparation 121.

EXAMPLE 62

Synthesis of 3-[5-(4-acetyl-3-hydroxy-2-propyl-phenoxymethyl)-pyridin-3-ylsulfanyl]-benzoic acid

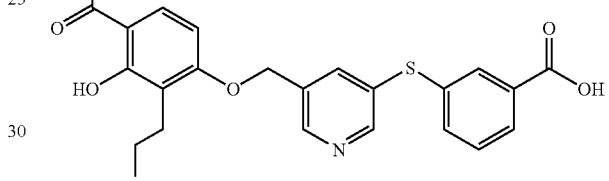

| Prep. No. | Chemical name | Structure | Physical data |
|---|---|---|---|
| 122 | 3-[6-(4-Acetyl-3-hydroxy-2-propyl-phenoxy methyl)-pyridin-3-ylsulfanyl]-benzoic acid methyl ester | 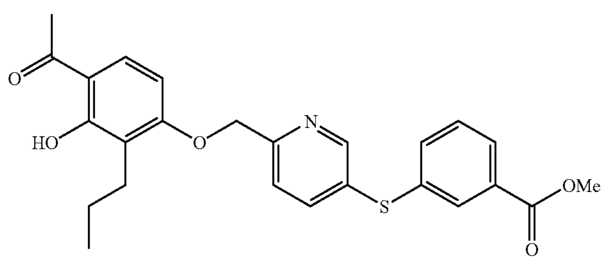 | MS (m/z): 450 (M − 1). |
| 123 | 6-(4-Acetyl-3-hydroxy-2-propyl-phenoxymethyl)-pyridine-2-carboxylic acid methyl ester | 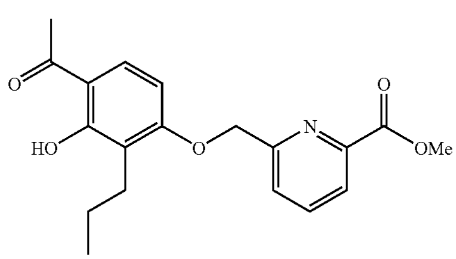 | MS (m/z): 344 (M + 1). |

Dissolve 3-[5-(4-acetyl-3-hydroxy-2-propyl-phenoxymethyl)-pyridin-3-ylsulfanyl]-benzoic acid methyl ester (379 mg, 0.84 mmol) in methanol (2 mL) and water (0.5 mL). Add 2N aqueous lithium hydroxide solution (0.42 mL, 0.84 mmol). After 12 hours, concentrate under reduced pressure and dissolve residue in 4N hydrochloric acid in dioxane. Add water until white precipitate forms, and collect by filtration. Triturate in ethyl acetate, then methanol. Collect the title compound by filtration as a white solid (317 mg, 0.73 mmol): $^1$H NMR (DMSO-$d_6$) δ 0.76 (t, 3H), 1.37 (m, 2H), 2.47 (m, 2H), 2.58 (s, 3H), 5.30 (s, 2H), 6.70 (d, 1H), 7.52 (t, 1H), 7.63 (m, 1H), 7.77 (m, 1H), 7.80 (m, 1H), 7.86 (m, 1H), 7.90 (d, 1H), 8.60 (m, 2H), 12.83 (s, 1H), 13.21 (br s, 1H); MS (m/z): 438 (M+1).

The following compound is prepared essentially by the method of Example 62.

| Ex. # | Chemical name | Structure | Physical data |
|---|---|---|---|
| 63 | 3-[6-(4-Acetyl-3-hydroxy-2-propyl-phenoxymethyl)-pyridin-3-ylsulfanyl]-benzoic acid | 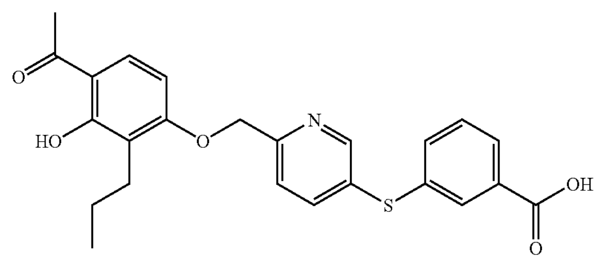 | $^1$H NMR (DMSO-$d_6$) δ 0.87 (t, 3H), 1.48 (m, 2H), 2.57 (s, 3H), 2.62 (m, 2H), 5.32 (s, 2H), 6.69 (d, 1H), 7.38 (m, 2H), 7.49 (d, 1H), 7.81 (m, 4H), 8.51 (1, 1H), 12.83 (s, 1H), (acid proton not observed): MS (m/z): 436 (M − 1). |

Preparation 124

Synthesis of 1-[4-(6-chloro-pyridin-3-ylmethoxy)-2-hydroxy-3-propyl-phenyl]-ethanone Add 5-chloromethyl-2-chloropyridine (4.12 g, 25.4 mmol) to a solution of 1-(2,4-dihydroxy-3-propyl-phenyl)-ethanone (4.94 g, 25.4 mmol) in dimethylformamide (40 mL). After 10 minutes add potassium carbonate (5.27 g, 38.1 mmol) and cesium carbonate (8.28 g, 25.4 mmol). Stir at room temperature for one hour, and then heat to 70° C. for 2 hours. Cool, partition between ethyl acetate (300 mL) and water (300 mL). Wash twice with water, brine, dry, and concentrate. Dissolve the crude solid in dichloromethane, and add hexane (70 mL) slowly. Triturate and filter to afford the title compound as an orange powder (2.95 g, 36%): $^1$H NMR (CDCl$_3$) δ 0.94 (t, 3H), 1.55 (sextet, 2H), 2.58 (s, 3H), 2.67 (t, 2H), 5.14 (s, 2H), 6.47 (d, 1H), 7.38 (d, 1H), 7.60 (d, 1H), 7.73 (d, 1H), 8.47 (s, 1H), 12.75 (s, 1H).

EXAMPLE 64

Synthesis of 3-[5-(4-acetyl-3-hydroxy-2-propyl-phenoxymethyl)-pyridin-2-ylsulfanyl]-benzoic acid

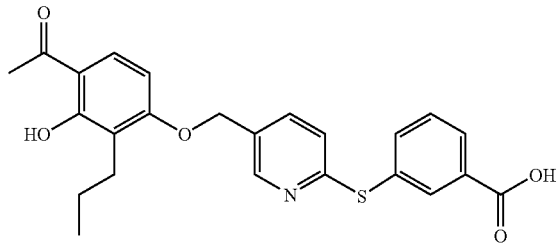

Dissolve 3-mercapto-benzoic acid (482 mg, 3.13 mmol, commercially available) in dimethylformamide (20 mL) at 0° C. Add washed sodium hydride (300 mg), and stir the mixture for 10 minutes. Add 1-[4-(6-chloro-pyridin-3-ylmethoxy)-2-hydroxy-3-propyl-phenyl]-ethanone (1.00 g, 3.13 mmol). Stir the mixture at room temperature for 2 hours; then stir at 65° C. for 2 hours and finally stir at 120° C. overnight. Dilute in ethyl acetate, and wash with water twice. Extract the organic layer with saturated aqueous sodium bicarbonate. Acidify the aqueous layer with 2N hydrochloric acid hydrochloric acid to pH 3. Extract with ethyl acetate, wash with brine, dry and concentrate to afford 620 mg of a crude red solid. Purify the residue via chromatography, eluting with 1:1 hexane:ethyl acetate to afford the title compound as a light yellow powder (120 mg): $^1$H NMR (DMSO-$d_6$) δ 0.84 (s, 3H), 1.44 (sextet, 2H), 2.55 (t, 2H), 2.58 (s, 3H), 5.24 (s, 2H), 6.74 (d, 1H), 7.14 (d, 1H), 7.63 (t, 1H), 7.75 (d, 1H), 7.81-7.84 (m, 2H), 8.02 (d, 1H), 8.05 (s, 1H), 8.51 (s, 1H), 12.84 (s, 1H), 13.21 (bs, 1H); MS (APCI-neg mode) m/z (rel intensity) 436 (100).

Preparation 125

Synthesis of 1-[2-hydroxy-4-(3-nitro-benzyloxy)-3-propyl-phenyl]-ethanone

Add 3-bromomethyl nitrobenzene (10.00 g, 46.3 mmol) to a solution of 1-(2,4-dihydroxy-3-propyl-phenyl)-ethanone (8.99 g, 46.3 mmol) in dimethylformamide (60 mL). After 10 minutes add potassium carbonate (9.60 g, 69.4 mmol) and cesium carbonate (15.08 g, 46.3 mmol). Stir at room temperature for one hour, then heat to 70° C. for 1.5 hours. Cool and add water (250 mL). Triturate for 15 minutes. Filter. Wash the solid with water several times, and then wash with hexanes. Dry to afford the title compound as an off white/light gray powder (12.9 g, 85%): $^1$H NMR (DMSO-$d_6$) δ 0.91 (t, 3H), 1.52 (m, 2H), 2.58 (s, 3H), 2.63 (m, 2H), 5.42 (s, 2H), 6.72 (d, 1H), 7.73 (t, 1H), 7.83 (d, 1H), 7.90 (d, 1H), 8.21 (d, 1H), 8.34 (s, 1H), 12.88 (bs, 1H).

The following compound is prepared essentially by the method of Preparation 125.

| Prep. No. | Chemical name | Structure | Physical data |
|---|---|---|---|
| 126 | 1-[2-Hydroxy-4-(2-nitro-benzyloxy)-3-propyl-phenyl]-ethanone | 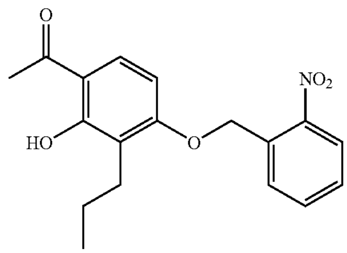 | $^1$H NMR (DMSO-$d_6$) δ 0.87 (t, 3H), 1.46 (sextet, 2H), 2.54 (t, 2H), 2.58 (s, 3H), 5.58 (s, 2H), 6.72 (d, 1H), 7.65 (t, 1H), 7.76-7.85 (m, 3H), 8.15 (d, 1H), 12.86 (s, 1H). |

Preparation 127

Synthesis of 1-[4-(3-amino-benzyloxy)-2-hydroxy-3-propyl-phenyl]-ethanone

Add zinc (21.6 g, 331 mmol) slowly to a solution of 1-[2-hydroxy-4-(3-nitro-benzyloxy)-3-propyl-phenyl]-ethanone (10.9 g, 6.07 mmol) in glacial acetic acid (120 mL). Stir the mixture for 3 hours. Dilute with dichloromethane (600 mL). Filter the reaction mixture through celite. Wash the celite pad several times with dichloromethane. Concentrate the combined filtrates. Partition the residue between ethyl acetate and saturated sodium bicarbonate. Wash the organic layer with brine, dry and concentrate to afford the title compound as a yellow solid (9.75 g, 98%): $^1$H NMR (CDCl$_3$) δ 0.96 (t, 3H), 1.58 (sextet, 2H), 2.54 (s, 3H), 2.71 (t, 2H), 5.07 (s, 2H), 6.46 (d, 1H), 6.62 (d, 1H), 6.71 (s, 1H), 6.78 (d, 1H), 7.16 (t, 1H), 7.54 (d, 1H), 12.75 (s, 1H).

The following compound is prepared essentially by the method of Preparation 127.

| Prep. No. | Chemical name | Structure | Physical data |
|---|---|---|---|
| 128 | 1-[4-(2-Amino-benzyloxy)-2-hydroxy-3-propyl-phenyl]-ethanone | 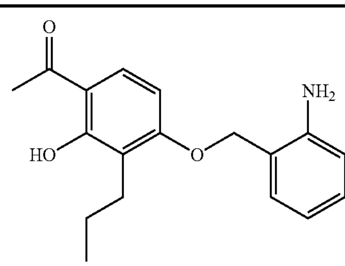 | $^1$H NMR (CDCl$_3$) δ 0.92 (t, 3H), 1.51 (sextet, 2H), 2.57 (s, 3H), 2.63 (t, 2H), 5.10 (s, 2H), 6.61 (d, 1H), 6.73 (d, 1H), 6.75 (t, 1H), 7.15-7.21 (m, 2H), 7.60 (d, 1H), 12.74 (s, 1H). |

Preparation 129

Synthesis of 3-[3-(4-acetyl-3-hydroxy-2-propyl-phenoxymethyl)-phenylamino]-benzoic acid methyl ester Combine 1-[4-(3-amino-benzyloxy)-2-hydroxy-3-propyl-phenyl]-ethanone (500 mg, 1.67 mmol), 3-bromo-benzoic acid methyl ester (326 mg, 1.52 mmol) and cesium carbonate (693 mg, 2.13 mmol) in toluene (25 mL) and stir. Purge reaction vessel with argon. Add BINAP [rac-2,2'-Bis(diphenyl-phosphino)-1,1'-binaphthyl] (142 mg, 0.228 mmol), and palladium acetate (34 mg, 0.152 mmol). Purge reaction vessel with argon. Heat to 100° C. After 18 hours, cool to ambient temperature. Add 10% aqueous citric acid, and extract with ethyl acetate. Combine the organic layers, dry with sodium sulfate, filter and concentrate to dryness. Purify the resulting residue by flash chromatography eluting with ethyl acetate: hexanes to yield the title compound as a white solid (280 mg, 43%): $^1$H NMR (DMSO-$d_6$) δ 0.81 (t, 3H), 1.46 (sextet, 2H), 2.57 (m, 5H), 3.82 (s, 3H), 5.23 (s, 2H), 6.71 (d, 1H), 6.95 (d, 1H), 7.01 (d, 1H), 7.19 (m, 1H), 7.28-7.41 (m, 4H), 7.65 (m, 1H), 7.81 (d, 1H), 8.49 (bs, 1H), 12.84 (s, 1H).

Preparation 130

Synthesis of 5-[3-(4-acetyl-3-hydroxy-2-propyl-phenoxymethyl)-phenylamino]-nicotinic acid methyl ester Combine 1-[4-(3-amino-benzyloxy)-2-hydroxy-3-propyl-phenyl]-ethanone (500 mg, 1.67 mmol), 5-bromo-nicotinic acid methyl ester (328 mg, 1.52 mmol) and cesium carbonate (693 mg, 2.13 mmol) in toluene (25 mL) and stir. Purge reaction vessel with Argon. Add BINAP [rac-2,2'-Bis(diphenyl-phosphino)-1,1'-binaphthyl] (142 mg, 0.228 mmol), and palladium acetate (34 mg, 0.152 mmol). Purge reaction vessel with argon. Heat to 100° C. After 18 hours, cool to ambient temperature. Add 10% aqueous citric acid, and extract with ethyl acetate. Combine the organic layers, dry with sodium sulfate, filter and concentrate to yield a residue. Purify the residue by flash chromatography eluting with ethyl acetate: hexanes to yield a yellow solid (250 mg, 38%): $^1$H NMR (DMSO-$d_6$) δ 0.81 (t, 3H), 1.46 (sextet, 2H), 2.57 (m, 5H), 3.86 (s, 3H), 5.25 (s, 2H), 6.72 (d, 1H), 7.03 (d, 1H), 7.08 (d, 1H), 7.24 (bs, 1H), 7.35 (t, 1H), 8.54 (dd, 1H), 8.69 (bs, 1H), 12.84 (s, 1H).

EXAMPLE 65

Synthesis of 3-[3-(4-acetyl-3-hydroxy-2-propyl-phenoxymethyl)-phenylamino]-benzoic acid

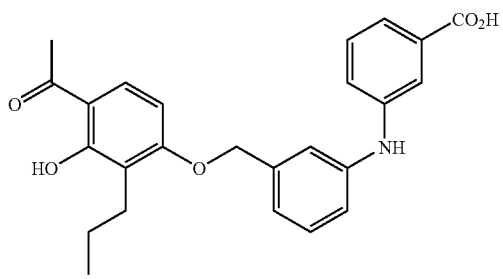

Add 1M aqueous lithium hydroxide (3.23 mL, 3.23 mmol) to a solution of 3-[3-(4-acetyl-3-hydroxy-2-propyl-phenoxymethyl)-phenylamino]-benzoic acid methyl ester (280 mg, 0.646 mmol) in isopropanol (25 mL) and stir. Heat to 80° C. After 1 hour, pour reaction into 1N aqueous hydrochloric acid (50 mL) and extract with ethyl acetate. Combine organic layers, dry with sodium sulfate, filter and concentrate to dryness. Purify the resulting residue by trituration (ether:hexanes) to yield the title compound as a yellow solid (200 mg, 74%): $^1$H NMR (DMSO-$d_6$) δ 0.81 (t, 3H), 1.46 (sextuplet, 2H), 2.58 (m, 5H), 5.23 (s, 2H), 6.71 (d, 1H), 6.94 (d, 1H), 7.02 (d, 1H), 7.19 (s, 1H), 7.29 (m, 3H), 7.40 (d, 1H), 7.65 (s, 1H), 7.81 (d, 1H), 8.44 (s, 1H), 12.73-12.92 (bs, 1H), 12.84 (s, 1H); MS (esi negative) m/z (rel intensity) 418 (100).

EXAMPLE 66

Synthesis of sodium 5-[3-(4-acetyl-3-hydroxy-2-propyl-phenoxymethyl)-phenylamino]-nicotinate

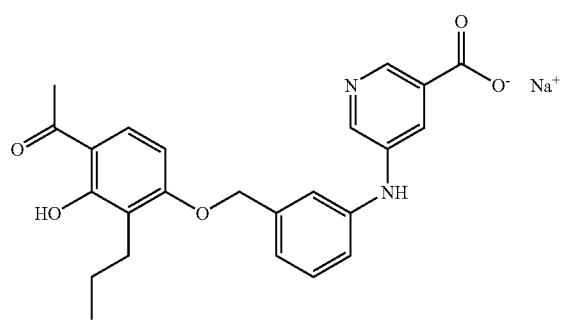

Add 1M aqueous lithium hydroxide (2.88 mL, 2.88 mmol) to a solution of 5-[3-(4-acetyl-3-hydroxy-2-propyl-phenoxymethyl)-phenylamino]-nicotinic acid methyl ester (250 mg, 0.575 mmol) in isopropanol (10 mL):tetrahydrofuran (5 mL) and stir. Heat to 80° C. After 1 hour, pour reaction into water (50 mL) and wash with methyl tert-butyl ether. Acidify with 2N aqueous hydrochloric acid, and extract with ethyl acetate. Combine organic layers, dry with sodium sulfate, filter and concentrate to dryness. Dissolve the resulting residue in ethyl acetate (10 mL), and add a solution of sodium ethyl hexanoate (83 mg, 0.499 mmol) in ethyl acetate (5 mL). After 30 minutes, filter the resulting precipitate to yield the title product as a white solid (77 mg, 30%): $^1$H NMR (Methanol) δ 0.88 (t, 3H), 1.54 (sextuplet, 2H), 2.56 (s, 3H), 2.67 (t, 2H), 3.64 (s, 1H), 5.19 (s, 2H), 6.66 (d, 1H), 7.02 (d, 1H), 7.11 (dd, 1H), 7.25 (s, 1H), 7.31 (t, 1H), 7.74 (d, 1H), 8.05 (m, 1H), 8.28 (d, 1H), 8.52 (d, 1H); MS (esi negative) m/z (rel intensity) 419 (100).

EXAMPLE 67

Synthesis of 2-[3-(4-acetyl-3-hydroxy-2-propyl-phenoxymethyl)-phenylamino]-nicotinic acid

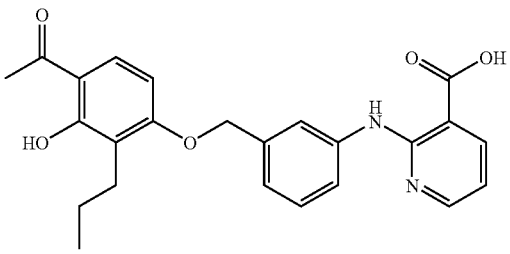

Heat a mixture of 2-chloro-nicotinic acid (132 mg, 0.835 mmol) and 1-[4-(3-amino-benzyloxy)-2-hydroxy-3-propyl-phenyl]-ethanone (250 mg, 0.835 mmol) to 130° C. After 18 hours, cool to ambient temperature and purify via flash chromatography (ethyl acetate:hexanes) to give a residue which was further purified by reverse phase chromatography (methanol:acetic acid:water) to yield the title product as a yellow solid (32 mg, 9%): $^1$H NMR (DMSO-$d_6$) δ 0.88 (t, 3H), 1.51 (sextet, 2H), 2.57 (s, 3H), 2.63 (t, 2H), 5.27 (s, 2H), 6.73 (d, 1H), 6.87 (dd, 1H), 7.06 (d, 1H), 7.34 (t, 1H), 7.67 (d, 1H), 7.81 (d, 1H), 7.88 (s, 1H), 8.26 (dd, 1H), 8.36 (dd, 1H), 10.66 (bs, 1H), 12.85 (s, 1H), 13.63 (bs, 1H); MS (esi negative) m/z (rel intensity) 419 (100).

Preparation 131

Synthesis of 2-[3-(4-acetyl-3-hydroxy-2-propyl-phenoxymethyl)-phenylamino]-isonicotinic acid methyl ester Combine 1-[4-(3-amino-benzyloxy)-2-hydroxy-3-propyl-phenyl]-ethanone (500 mg, 1.67 mmol), 2-chloro-isonicotinic acid methyl ester (287 mg, 1.67 mmol) and cesium carbonate (762 mg, 2.34 mmol) in toluene (25 mL) and stir. Purge reaction vessel with argon. Add 2-(bicyclohexylphosphino)biphenyl (234 mg, 0.668 mmol), and tris(dibenzylideneacetone)dipalladium (153 mg, 0.167 mmol). Purge reaction vessel with argon. Heat to 110° C. After 18 hours, cool to ambient temperature. Add diethyl ether (25 mL) and filter. Concentrate filtrate under reduced pressure to dryness. Purify the resulting residue by flash chromatography eluting with ethyl acetate:hexanes to yield the title compound as a yellow solid (282 mg, 39%): $^1$H NMR (DMSO-$d_6$) δ 0.86 (t, 3H), 1.52 (sextet, 2H), 2.57 (s, 3H), 2.63 (t, 2H), 3.88 (s, 3H), 5.25 (bs, 2H), 6.72 (d, 1H), 6.99 (d, 1H), 7.14 (d, 1H), 7.31 (t, 1H), 7.39 (s, 1H), 7.58 (d, 1H), 7.80 (d, 1H), 7.91 (s, 1H), 8.29 (d, 1H), 9.43 (s, 1H), 12.85 (s, 1H).

EXAMPLE 68

Synthesis of 2-[3-(4-acetyl-3-hydroxy-2-propyl-phenoxymethyl)-phenylamino]-isonicotinic acid

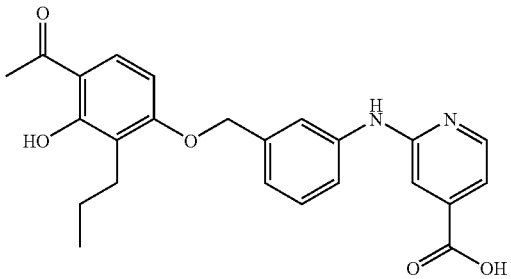

Add 1M aqueous lithium hydroxide (2.14 mL, 2.14 mmol) to a solution of 2-[3-(4-acetyl-3-hydroxy-2-propyl-phenoxymethyl)-phenylamino]-isonicotinic acid methyl ester (282 mg, 0.649 mmol) in tetrahydrofuran (20 mL):water (20 mL) and stir. Heat to 80° C. After 1 hour, pour reaction into 1N aqueous hydrochloric acid (50 mL) and filter the resulting precipitate to yield the title compound as a yellow solid (59 mg, 22%): $^1$H NMR (DMSO-$d_6$) δ 0.86 (t, 3H), 1.52 (sextet, 2H), 2.57 (s, 3H), 2.63 (t, 2H), 5.25 (s, 2H), 6.72 (d, 1H), 6.99 (d, 1H), 7.13 (d, 1H), 7.30 (t, 1H), 7.37 (s, 1H), 7.56 (d, 1H), 7.80 (d, 1H), 7.91 (s, 1H), 8.28 (d, 1H), 9.37 (s, 1H), 12.85 (s, 1H), 13.44 (bs, 1H); MS (esi negative) m/z (rel intensity) 419 (100).

EXAMPLE 69

Synthesis of 2-[3-(4-acetyl-3-hydroxy-2-propyl-phenoxymethyl)-phenylamino]-nicotinic acid

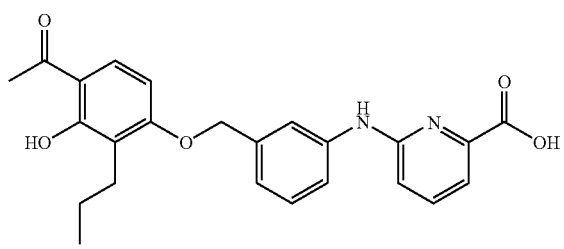

Heat a mixture of 6-chloro-pyridine-2-carboxylic acid (263 mg, 1.67 mmol) and 1-[4-(3-amino-benzyloxy)-2-hydroxy-3-propyl-phenyl]-ethanone (500 mg, 1.67 mmol) to 130° C. After 18 hours, cool to ambient temperature. Purify the resulting residue by reverse phase chromatography (methanol:acetic acid:water) to yield the title product as a yellow solid (75 mg, 11%): $^1$H NMR (DMSO-$d_6$) δ 0.84 (t, 3H), 1.48 (sextet, 2H), 2.57 (s, 3H), 2.60 (t, 2H), 5.22 (s, 2H), 6.73 (d, 1H), 6.99 (d, 1H), 7.03 (d, 1H), 7.31 (t, 1H), 7.43 (d, 1H), 7.70 (t, 1H), 7.77 (s, 1H), 7.79 (d, 1H), 7.89 (d, 1H), 9.34 (s, 1H), 12.84 (s, 1H), 12.89 (bs, 1H); MS (esi negative) m/z (rel intensity) 419 (100).

Preparation 132

Synthesis of 3-[3-(4-acetyl-3-hydroxy-2-propyl-phenoxymethyl)-phenylamino]-benzonitrile Combine 1-[4-(3-amino-benzyloxy)-2-hydroxy-3-propyl-phenyl]-ethanone (1.65 g, 5.51 mmol), 3-bromo-benzonitrile (912 mg, 5.01 mmol), cesium carbonate (2.29 g, 7.01 mmol), and 18-crown-6 (132 mg, 0.501 mmol) in toluene (25 mL) and stir. Purge reaction vessel with argon. Add BINAP [rac-2,2'-bis(diphenyl-phosphino)-1,1'-binaphthyl] (468 mg, 0.752 mmol), and palladium acetate (112 mg, 0.501 mmol). Purge reaction vessel with argon. Heat to 100° C. for 18 hours and cool to ambient temperature. Add 10% aqueous citric acid, and extract with ethyl acetate. Combine the organic layers, dry with sodium sulfate, filter and concentrate to dryness. Purify the resulting residue by flash chromatography eluting with 30% ethyl acetate:hexanes to yield a yellow oil (1.36 g, 68%): $^1$H NMR (CDCl$_3$) δ 0.92 (t, 3H), 1.56 (sextet, 2H), 2.56 (s, 3H), 2.69 (t, 2H), 5.15 (s, 2H), 5.86 (bs, 1H), 6.49 (d, 1H), 7.06 (m, 2H), 7.15-7.21 (m, 3H), 7.27-7.37 (m, 3H), 7.59 (d, 1H), 12.75 (s, 1H).

Preparation 133

Synthesis of 4-[3-(4-acetyl-3-hydroxy-2-propyl-phenoxymethyl)-phenylamino]-benzonitrile Combine 1-[4-(3-amino-benzyloxy)-2-hydroxy-3-propyl-phenyl]-ethanone (1.00 g, 3.34 mmol), 4-bromo-benzonitrile (553 mg, 3.03 mmol), cesium carbonate (1.39 g, 4.25 mmol), and 18-crown-6 (80 mg, 0.304 mmol) in toluene (25 mL) and stir. Purge reaction vessel with argon. Add BINAP [rac-2,2'-bis(diphenyl-phosphino)-1,1'-binaphthyl] (284 mg, 0.456 mmol), and palladium acetate (68 mg, 0.304 mmol). Purge reaction vessel with argon. Heat to 100° C. After 18 hours, cool to ambient temperature. Add 10% aqueous citric acid, and extract with ethyl acetate. Combine the organic layers, dry with sodium sulfate, filter and concentrate to dryness. Purify the resulting residue by flash chromatography eluting with 30% ethyl acetate:hexanes to yield the title compound as a yellow solid (760 mg, 63%): $^1$H NMR (CDCl$_3$) δ 0.92 (t, 3H), 1.58 (sextet, 2H), 2.56 (s, 3H), 2.69 (t, 2H), 5.15 (s, 2H), 6.07 (bs, 1H), 6.47 (d, 1H), 6.98 (d, 2H), 7.13 (t, 2H), 7.23 (m, 1H), 7.38 (t, 1H), 7.49 (d, 2H), 7.58 (d, 1H), 12.75 (s, 1H).

EXAMPLE 69

Synthesis of 1-(2-hydroxy-3-propyl-4-{3-[3-(2H-tetrazol-5-yl)-phenylamino]-benzyloxy}-phenyl)-ethanone

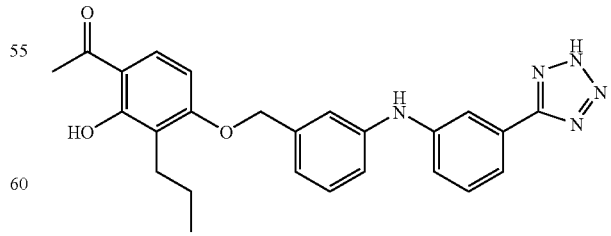

Using the general procedure for formation of tetrazole (Et$_3$NHCl method) of Example 1 using 3-[3-(4-acetyl-3-hydroxy-2-propyl-phenoxymethyl)-phenylamino]-benzonitrile (1.36 g, 3.39 mmol), sodium azide (662 mg, 10.2 mmol), and triethylamine hydrochloride (1.40 g, 10.2 mmol) to yield the title product as a yellow solid (313 mg, 21%): $^1$H NMR (DMSO-d$_6$) δ 0.791 (t, 3H), 1.43 (sextuplet, 2H), 2.57 (m, 5H), 5.24 (s, 2H), 6.72 (d, 1H), 6.98 (d, 1H), 7.08 (d, 1H), 7.24 (m, 2H), 7.32 (t, 1H), 7.44 (m, 2H), 7.79 (m, 2H), 8.55 (s, 1H), 12.84 (s, 1H); MS (esi negative) m/z (rel intensity) 442 (100).

EXAMPLE 70

Synthesis of 1-(2-hydroxy-3-propyl-4-{3-[4-(2H-tetrazol-5-yl)-phenylamino]-benzyloxy}-phenyl)-ethanone

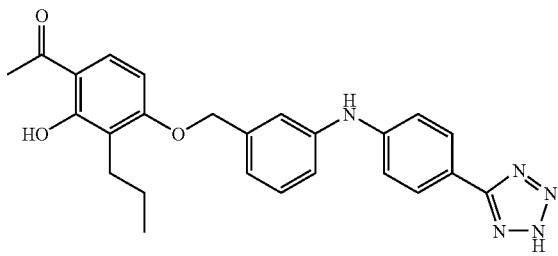

Using the general procedure for formation of tetrazole (Et$_3$NHCl method) of Example 1 using 4-[3-(4-acetyl-3-hydroxy-2-propyl-phenoxymethyl)-phenylamino]-benzonitrile (380 mg, 0.949 mmol), sodium azide (308 mg, 4.74 mmol), and triethylamine hydrochloride (653 mg, 4.74 mmol) to yield the title product as a white solid (120 mg, 29%): $^1$H NMR (DMSO-d$_6$) δ 0.785 (t, 3H), 1.44 (sextuplet, 2H), 2.52 (s, 3H), 2.55 (t, 2H), 5.20 (s, 2H), 6.68 (d, 1H), 6.97 (d, 1H), 7.04 (d, 1H), 7.15 (d, 2H), 7.24 (s, 1H), 7.29 (t, 1H), 7.76 (d, 1H), 7.82 (d, 2H), 8.69 (s, 1H), 12.80 (s, 1H); MS (esi negative) m/z (rel intensity) 442 (100).

Preparation 134

Synthesis of 1-[4-(4-bromomethyl-benzyloxy)-3-chloro-2-hydroxy-phenyl]-ethanone

Combine 1-(3-chloro-2,4-dihydroxy-phenyl)-ethanone (6.00 g, 32.2 mmol) and 1,4-bis-bromomethyl-benzene (8.48 g, 31.2 mmol) and potassium carbonate (4.44 g, 32.2 mmol) in acetone (400 ml) and heat to reflux. After 1 h, cool to room temperature and add 10% hydrochloric acid (300 mL). Filter to collect and triturate resultant solid in 1:1 ether/hexanes. Purify by column chromatography, eluting with 40% tetrahydrofuran/hexanes to obtain 1-[4-(4-bromomethyl-benzyloxy)-3-chloro-2-hydroxy-phenyl]-ethanone (3.00 g, 8.12 mmol) as a white solid. MS (m/z): 368.9 (M−1).

Preparation 135

Synthesis of 1-(3-bromo-phenyl)-3-dimethylamino-propenone

Combine 1-(3-bromo-phenyl)-ethanone (10 g, 50.2 mmol) and dimethylformamide dimethylacetal (60 g, 502 mmol) in a sealed tube, heat to 150° C. for 12 hours. Cool the solution and evaporate the excess dimethylformamide dimethylacetal. Purify residue by column chromatography to obtain the title compound (3.05 g, 12.0 mmol) as a white solid. MS (m/z): 254.1 (M).

Preparation 136

Synthesis of 4-(3-bromo-phenyl)-pyrimidin-2-ol

Combine 1-(3-bromo-phenyl)-3-dimethylamino-propenone (3.00 g, 11.8 mmol), urea (544 mg, 11.8 mmol), sodium ethoxide (4.00 g, 21% wt in ethanol) and ethanol (24 mL) and heat to 150° C. in sealed tube overnight. Cool to room temperature and pour into 1% hydrochloric acid (50 mL). Collect white solid by filtration to obtain 4-(3-bromo-phenyl)-pyrimidin-2-ol (2.60 g, 10.4 mmol). MS (m/z): 251.2 (M+1).

Preparation 137

Synthesis of 4-[3-(5,5-dimethyl-[1,3,2]dioxaborinan-2-yl)-phenyl]-pyrimidin-2-ol Combine 4-(3-bromo-phenyl)-pyrimidin-2-ol (1.50 g, 5.97 mmol), bis(neopentyl glycolato)diboron (1.62 g, 7.17 mmol), Pd(dppf)Cl$_2$ (505 mg, 0.597 mmol) and potassium acetate (1.76 g, 17.9 mmol) in a purged (N2) flask, add dry DMSO (50 mL) and plunge into a 80° C. bath. Heat overnight, then pour into 1% hydrochloric acid (100 mL). Neutralize with sodium bicarbonate, and extract with ethyl acetate, dry, filter and condense to afford 4-[3-(5,5-dimethyl-[1,3,2]dioxaborinan-2-yl)-phenyl]-pyrimidin-2-ol (300 mg) as a brown solid. MS (m/z): 173.1 (M-C5H$_{10}$BO$_2$+1).

Preparation 138

Synthesis of 4-(3-bromo-phenyl)-pyrimidin-2-ylamine

Combine 1-(3-bromo-phenyl)-3-dimethylamino-propenone (3.00 g, 11.8 mmol) and guanidinium chloride (1.12 g, 11.8 mmol), sodium ethoxide (5 mL, 21% wt solution in ethanol), absolute EtOH (24 mL) and heat to reflux overnight. Cool to room temperature and pour into 1% hydrochloric acid (200 mL). Extract with ethyl acetate, dry over sodium sulfate and condense to afford 4-(3-bromo-phenyl)-pyrimidin-2-ylamine (930 mg, 3.72 mmol) as a white solid. MS (m/z): 250.2 (M).

Preparation 139

Synthesis of 4-[3-(5,5-dimethyl-[1,3,2]dioxaborinan-2-yl)-phenyl]-pyrimidin-2-ylamine The title compound is prepared essentially as described for Preparation 137 using 4-(3-bromo-phenyl)-pyrimidin-2-ylamine (2.00 g, 8.00 mmol). The title compound is isolated (1.71 g, 6.04 mmol) as a brown solid. MS (m/z): 216.2 (M-C5H$_8$+1).

Preparation 140

Synthesis of 3-(tetrahydro-pyran-2-yloxymethyl)-benzonitrile

Add p-toluene sulphonic acid (2.11 g, 12.2 mmol) to a solution of 3-hydroxymethyl-benzonitrile (16.30 g, 122.4 mmol) and 3,4-dihydro-2H-pyran (51.5 g, 612 mmol) in diclioromethane (500 ml) and stir. After 90 minutes, pour reaction into saturated sodium bicarbonate, remove organics, dry with sodium sulfate, filter and concentrate to give a dark brown oil. Purify the residue by flash chromatography eluting with a gradient of 10-15% ethyl acetate:hexanes to yield the title product as a clear oil (16.20 g, 61%): $^1$H NMR (CDCl$_3$) δ 1.53-1.91 (m, 6H), 3.56 (m, 1H), 3.88 (m, 1H), 4.53 (d, 1H), 4.72 (t, 1H), 4.81 (d, 1H), 7.45 (t, 1H), 7.58 (m, 2H), 7.69 (s, 1H)

Preparation 141

Synthesis of 3-[3-(tetrahydro-pyran-2-yloxymethyl)-phenyl]-4H-[1,2,4]oxadiazol-5-one Add 50% aqueous hydroxylamine (9.73 g, 147 mmol) dropwise to a refluxing solution of 3-(tetrahydro-pyran-2-yloxymethyl)-benzonitrile (8.00 g, 36.8 mmol) in isopropanol (0.1M). After 2 hours, cool to room temperature and concentrate under reduced pressure to give a residue. Dissolve the residue in dioxane (0.1M). Add carbonyldiimidazole (7.16 g, 44.2 mmol) and heat to 110° C. After 30 minutes, cool to room temperature and pour into water. Extract with ethyl acetate. Combine the organic layers, dry with sodium sulfate, filter and concentrate under reduced pressure to yield the title product as a white solid (90.10 g, 89%): $^1$H NMR (CDCl$_3$) δ 1.53-1.95 (m, 6H), 3.59 (m, 1H), 3.93 (m, 1H), 4.58 (d, 1H), 4.77 (t, 1H), 4.88 (d, 1H), 7.52 (t, 1H), 7.57 (d, 1H), 7.71 (d, 1H), 7.82 (s, 1H), 11.16 (bs, 1H)

Preparation 142

Synthesis of 3-(3-hydroxymethyl-phenyl)-4H-[1,2,4]oxadiazol-5-one

Add 10% hydrochloric acid (100 ml) to a solution of 3-[3-(tetrahydro-pyran-2-yloxymethyl)-phenyl]-4H-[1,2,4]oxadiazol-5-one (4.50 g, 16.3 mmol) in tetrahydrofuran (0.1M) and stir. After 18 hours, pour reaction into brine and extract with ethyl acetate. Combine the organic layers, dry with sodium sulfate, filter and concentrate under reduced pressure to yield the title product as a white solid (3.10 g, 99%): $^1$H NMR (DMSO-d$_6$) δ 4.57 (s, 2H), 7.55 (m, 2H), 7.67 (dt, 1H), 7.81 (m, 1H), 12.95 (bs, 1H).

Preparation 143

Synthesis of 3-(5-oxo-4,5-dihydro-[1,2,4]oxadiazol-3-yl)-benzaldehyde

Add pyrdinium chloro chromate (5.22 g, 24.2 mmol) to a solution of 3-(3-hydroxymethyl-phenyl)-4H-[1,2,4]oxadiazol-5-one (3.10 g, 16.1 mmol) in tetrahydrofuran:dichloromethane (125 mL:125 mL) and stir. After 4 hours concentrate under reduced pressure to give a residue. Purify the residue by flash chromatography eluting with ethyl acetate: hexanes:acetic acid (50%:50%:0.1%) to yield the title product as a white solid (2.20 g, 72%): $^1$H NMR (DMSO-d$_6$) δ 7.83 (t, 1H), 8.10-8.17 (m, 2H), 8.35 (m, 1H), 10.09 (s, 1H), 13.15 (bs, 1H).

Preparation 144

Synthesis of 1-[2-hydroxy-4-(4-iodo-benzyloxy)-3-propyl-phenyl]-ethanone

Add 1-bromomethyl-4-iodo-benzene (10.00 g, 33.7 mmol) to a solution of 1-(2,4-dihydroxy-3-propyl-phenyl)-ethanone (6.54 g, 33.7 mmol) and cesium carbonate (13.2 g, 40.4 mmol) in acetone (500 mL) and stir. After 48 hours, pour the reaction into water and extract with ethyl acetate. Combine the organic layers, dry with sodium sulfate, filter and concentrate under reduced pressure to give a residue. Purify the residue by flash chromatography eluting with a gradient of ethyl acetate:hexanes to yield the title product as a yellow solid (7.20 g, 52%): $^1$H NMR (CDCl$_3$) δ 0.95 (t, 3H), 1.56 (sextet, 2H), 2.56 (s, 3H), 2.69 (t, 2H), 5.09 (s, 2H), 6.43 (d, 1H), 7.15 (d, 2H), 7.57 (d, 1H), 7.73 (d, 2H), 12.74 (s, 1H).

Preparation 145

Synthesis of 1-(4-iodo-benzyloxy)-2-propyl-3-trimethylsilanyloxy-4-(1-trimethylsilanyloxy-vinyl)-benzene Add lithium hexamethyldisilazide (1M solution in tetrahydrofuran, 5.36 ml, 5.36 mmol) to a solution of 1-[2-hydroxy-4-(4-iodo-benzyloxy)-3-propyl-phenyl]-ethanone (1.00 g, 2.44 mmol) in tetrahydrofuran (25 mL) cooled to −78° C. After 1 hour, add trimethylsilyl chloride (794 mg, 7.31 mmol). After 1 hour, warm reaction to room temperature and stir overnight. Pour the reaction into saturated sodium bicarbonate and extract with ethyl acetate. Combine the organic layers, dry with sodium sulfate, filter, and concentrate. Dry on high-vac overnight to yield the title product as a dark yellow oil (1.35 g, 99%): $^1$H NMR (CDCl$_3$) δ 0.16 (s, 9H), 0.23 (s, 9H), 0.94 (t, 3H), 1.52 (sextet, 2H), 2.60 (t, 2H), 4.49 (s, 1H), 4.53 (s, 1H), 4.99 (s, 2H), 6.49 (d, 1H), 7.10 (d, 1H), 7.17 (d, 2H), 7.71 (d, 2H).

Preparation 146

Synthesis of 1-[3-chloro-2-hydroxy-4-(4-iodo-benzyloxy)-phenyl]-ethanone

Add 1-bromomethyl-4-iodo-benzene (10.00 g, 33.7 mmol) to a solution of 1-(3-chloro-2,4-dihydroxy-phenyl)-ethanone (7.92 g, 42.4 mmol) and cesium carbonate (16.6 g, 50.9 mmol) in dimethylformamide (250 mL) and stir. After 18 hours, pour reaction into water and extract with ethyl acetate. Combine organic layers and wash with 2N NaOH. Dry with sodium sulfate, filter, and concentrate under reduced pressure to give a residue. Purify the residue by flash chromatography eluting with a gradient of ethyl acetate:hexanes to yield the title product as a tan solid (4.00 g, 23%): $^1$H NMR (DMSO-d$_6$) δ 2.62 (s, 3H), 5.33 (s, 2H), 6.87 (d, 1H), 7.27 (d, 2H), 7.78 (d, 2H), 7.94 (d, 1H), 13.13 (s, 1H).

Preparation 147

Synthesis of 2-chloro-1-(4-iodo-benzyloxy)-3-trimethylsilanyloxy-4-(1-trimethylsilanyloxy-vinyl)-benzene Add sodium hexamethyldisilazide (1M solution in tetrahydrofuran, 21.9 mL, 21.9 mmol) to a solution of 1-[3-chloro-2-hydroxy-4-(4-iodo-benzyloxy)-phenyl]-ethanone (4.00 g, 9.94 mmol) in tetrahydrofuran (100 mL) chilled to −78° C. After 1 hour, add trimethylsilyl chloride (3.24 g, 29.8 mmol). After 1 hour, warm reaction to room temperature and stir overnight. Pour reaction into saturated sodium bicarbonate and extract with ethyl acetate. Combine organic layers, dry with sodium sulfate, filter, and concentrate. Dry in vacuo overnight to yield the title product as a dark yellow oil (5.30 g, 98%): $^1$H NMR (CDCl$_3$) δ 0.21 (s, 9H), 0.28 (s, 9H), 4.55 (s, 1H), 4.79 (s, 1H), 5.08 (s, 2H), 6.56 (d, 1H), 7.22 (m, 3H), 7.71 (d, 2H)

Preparation 148

Synthesis of 3-(tert-butyl-dimethyl-silanyloxymethyl)-benzonitrile

Add tert-butyl-chloro-dimethyl-silane (11.9 g, 78.9 mmol) to a solution of 3-hydroxymethyl-benzonitrile (10.00 g, 75.10 mmol) and imidazole (6.14 g, 90.1 mmol) in dichloromethane (1 L) and stir. After 18 hours, pour reaction into 1% hydrochloric acid. Remove organic layer, dry with sodium sulfate, filter, and concentrate under reduced pressure to yield the title product as a clear yellow oil (18.5 g, 99%): $^1$H NMR (CDCl$_3$) δ 0.12 (s, 6H), 0.95 (s, 9H), 4.75 (s, 2H), 7.43 (t, 1H), 7.53 (d, 2H), 7.63 (s, 1H).

Preparation 149

Synthesis of [3-(2-oxo-2,3-dihydro-2λ$^4$-[1,2,3,5]oxathiadiazol-4-yl)-phenyl]-methanol Add hydroxylainine (50% aqueous solution, 5.34 g, 80.8 mmol) dropwise to a refluxing solution of 3-(tert-butyl-dimethyl-silanyloxymethyl)-benzonitrile (5.00 g, 20.2 mmol) in isopropanol (0.1 M). After 2 hours, concentrate the reaction under reduced pressure and azeotrope with toluene. Add dichloromethane (0.1 M) and pyridine (1.92 g, 24.3 mmol) and cool reaction to −78° C. Add thionyl chloride (2.64 g, 22.2 mmol) via syringe. After 4 hours, warm the reaction to room temperature. Concentrate the reaction under reduced pressure. Add tetrahydrofuran (0.1M) and 10% hydrochloric acid (0.1M) and stir. After 18 hours, add brine and extract with 25% isopropyl alcohol:75% dichloromethane. Combine organic layers, dry with sodium sulfate, filter and concentrate under reduced pressure to yield the title product as a yellow solid (3.90 g, 91%): $^1$H NMR (DMSO-d$_6$) δ 4.63 (s, 2H), 5.42 (bs, 1H), 7.59 (m, 2H), 7.75 (dt, 1H), 7.88 (s, 1H), 12.23 (bs, 1H).

Preparation 150

Synthesis is of 1-[3-chloro-2-hydroxy-4-(3-iodo-benzyloxy)-phenyl]-ethanone

Add triphenylphosphine (13.6 g, 51.7 mmol) and DIAD (10.5 g, 51.7 mmol) to a solution of (3-iodo-phenyl)-methanol (11.0 g, 47.0 mmol) and 1-(3-Chloro-2,4-dihydroxyphenyl)-ethanone (8.77 g, 47.0 mmol) in dichloromethane:tetrahydrofuran (250 ml:250 ml) and stir. After 18 hours, concentrate the reaction, and load directly onto silica. Purify the residue by flash chromatography eluting with acetone:hexanes to yield the title product as a white solid (12.2 g, 64%): $^1$H NMR (DMSO-d$_6$) δ 2.62 (s, 3H), 5.34 (s, 2H), 6.88 (d, 1H), 7.23 (t, 1H), 7.48 (d, 1H), 7.72 (d, 1H), 7.87 (s, 1H), 7.96 (d, 1H), 13.14 (s, 1H)

Preparation 151

Synthesis of 2-chloro-1-(3-iodo-benzyloxy)-3-trimethylsilanyloxy-4-(1-trimethyl-silanyloxy-vinyl)-benzene Add sodium hexamethyldisilazide (1 M solution in tetrahydrofuran, 20.2 ml, 20.2 mmol) to a solution of 1-[3-chloro-2-hydroxy-4-(4-iodo-benzyloxy)-phenyl]-ethanone (3.70 g, 9.19 mmol) in tetrahydrofuran (100 mL) chilled to −78° C. After 1 hour, add trimethylsilyl chloride (3.00 g, 27.6 mmol). After 1 hour, warm reaction to room temperature and stir overnight. Pour reaction into saturated sodium bicarbonate and extract with ethyl acetate. Combine organic layers, dry with sodium sulfate, filter, and concentrate. Dry on high-vac overnight to yield the title product as a dark yellow oil (5.0 g, 99%): $^1$H NMR (CDCl$_3$) δ 0.21 (s, 9H), 0.28 (s, 9H), 4.55 (d, 1H), 4.79 (d, 1H), 5.08 (s, 2H), 6.56 (d, 1H), 7.12 (t, 1H), 7.24 (d, 1H), 7.42 (d, 1H), 7.65 (d, 1H), 7.82 (s, 1H)

Preparation 152

Synthesis of 2-hydroxymethyl-isonicotinonitrile

Add ammonium persulfate (70.1 g, 307 mmol) to a solution of isonicotinonitrile (16.00 g, 154 mmol) in methanol:water:sulfuric acid (275 mL:135 mL:11 mL). Heat solution to reflux. After 24 hours, pour reaction onto ice and neutralize with ammonium hydroxide (70 ml). Extract solution with chloroform (3×600 ml). Combine the organic layers, dry with sodium sulfate, filter, and concentrate under reduced pressure to give a residue. Purify the residue by flash chromatography eluting with acetone:dichloromethane (1:6) to yield the title compound as a white solid (5.86 g, 28%): $^1$H NMR (CDCl$_3$) δ 3.17 (t, 1H), 4.84 (d, 1H), 7.45 (m, 1H), 7.58 (s, 1H), 8.74 (d, 1H)

Preparation 153

Synthesis of 5-(3-(hydroxymethyl)phenylthio)nicotinonitrile

Add K$_2$CO$_3$ (6.91 g, 50.0 mmol) to a solution of (3-mercaptophenyl)methanol (2.94 g, 21.0 mmol) and 5-bromonicotinonitrile (3.66 g, 20.0 mmol) in DMA (100 mL). Heat the mixture at 110° C. for 2 h. Cool to room temperature. Dilute with EtOAc. Filter. Wash the residue with EtOAc. Concentrate. Dissolve the residue in EtOAc and filter. Concentrate to afford the title compound (4.80 g, quant.): $^1$H NMR (CDCl$_3$) δ 2.20 (t, J=5.5 Hz, 1H), 4.74 (d, J=5.5 Hz, 2H), 7.38-7.44 (m, 3H), 7.52-7.53 (m, 1H), 7.62 (dd, J=2.0, 2.3 Hz, 1H), 8.62 (dd, J=2.0, 2.3 Hz, 2H).

Preparation 154

Synthesis of 5-(4-(hydroxymethyl)phenylthio)nicotinonitrile

Using the method of Preparation 153 using (4-mercaptophenyl)methanol (4.42 g, 31.5 mmol) and 5-bromonicotinonitrile (5.49 g, 30.0 mmol) affords the title compound (3.60 g, 50%): $^1$H NMR (CDCl$_3$) δ 1.92 (t, J=5.9 Hz, 1H), 4.77 (d, J=5.9 Hz, 2H), 7.48 (q, J=8.2 Hz, 4H), 7.58 (t, J=2.0 Hz, 1H), 8.61 (dd, J=2.0, 3.1 Hz, 2H).

Preparation 155

Synthesis of 5-(3-(Hydroxymethyl)phenylthio)picolinonitrile

Add NaHCO$_3$ (12.0 g, 143 mmol) to a solution of (3-mercaptophenyl)methanol (10.0 g, 71.3 mmol) and 5-bromopicolinonitrile (13.0 g, 71.3 mmol) in DMF. Heat the mixture overnight. Dilute with ethyl acetate. Wash the mixture with water. Dry, filter and concentrate to afford the title compound (10.1 g, 59%) (Solidifies after standing). MS (APCI-pos) m/z (rel intensity): 243 (M+H, 100%).

Preparation 156

Synthesis of 5-(4-(hydroxymethyl)phenylthio)picolinonitrile

Using the method of Preparation 155 using (4-mercaptophenyl)methanol (10.0 g, 71.3 mmol) and 5-bromopicolinonitrile (13.0 g, 71.3 mmol) affords the title compound (4.90 g, 28%).): 243 (M+H, 100%).

Preparation 157

Synthesis of 6-(3-(hydroxymethyl)phenylthio)nicotinonitrile

Using the method of Preparation 155 using (3-mercaptophenyl)methanol (10.0 g, 71.3 mmol) and 6-chloronicotinonitrile (19.8 g, 142.7 mmol) affords the title compound (13.1 g, 76%): 243 (M+H, 100%).

Preparation 158

Synthesis of 2-(3-(hydroxymethyl)phenylthio)isonicotinonitrile

Using the method of Preparation 155 using (3-mercaptophenyl)methanol (6.00 g, 42.8 mmol) and 2-chloroisonicotinitrile (5.65 g, 40.8 mmol) affords the title compound (6.22 g, 63%): 243 (M+H, 100%).

Preparation 159

Synthesis of 6-(4-(hydroxymethyl)phenylthio)isonicotinonitrile

Using the method of Preparation 155 using (4-mercaptophenyl)methanol (6.00 g, 42.8 mmol) and 6-chloronicotinonitrile (5.65 g, 40.8 mmol) affords the title compound (7.24 g, 73%): 243 (M+H, 100%).

Preparation 160

Synthesis of 5-(3-((4-acetyl-3-hydroxy-2-methylphenoxy)methyl)phenylthio)nicotinonitrile

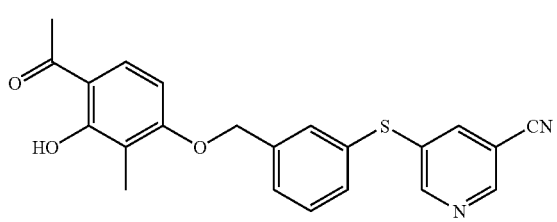

Add triphenylphosphine (5.24 g, 20.0 mmol) and diisopropylazodicarboxylate (4.04 g, 20.0 mmol) to a solution of 5-(3-(hydroxymethyl)phenylthio)nicotinonitrile (4.84 g, 20.0 mmol) and 1-(2,4-dihydroxy-3-methylphenyl)ethanone (3.32 g, 20.0 mmol) in THF (100 mL). Stir the reaction for 24 h. Quench the reaction with water and extract with EtOAc. Dry, filter and concentrate. Purify the residue by flash chromatography on silica gel eluting with a mixture of EtOAc and hexanes (15:85 to 20:80) to give an off-white solid. Recrystallize the solid from a mixture of EtOAc and hexanes to afford the title compound (3.94 g, 50%): $^1$H NMR (CDCl$_3$) δ 2.14 (s, 3H), 2.57 (s, 3H), 5.18 (s, 2H), 6.44 (d, J=9.0 Hz, 1H), 7.46-7.49 (m, 3H), 7.52 (s, 1H), 7.59 (d, J=9.0 Hz, 1H), 7.62-7.63 (m, 1H), 8.63-8.64 (m, 2H), 12.78 (s, 1H).

Preparation 161

Synthesis of 5-(3-((4-acetyl-3-hydroxy-2-propylphenoxy)methyl)phenylthio)nicotinonitrile Using the method of Preparation 160 using 5-(3-(hydroxymethyl)phenylthio) nicotinonitrile (3.90 g, 16.1 mmol) and 1-(2,4-dihydroxy-3-propylphenyl)ethanone (3.13 g, 16.1 mmol) affords the title compound (4.80 g, 71%): $^1$H NMR (CDCl$_3$) δ 0.92 (t, J=7.2 Hz, 3H), 1.50-1.59 (m, 2H), 2.57 (s, 3H), 2.68 (t, J=7.6 Hz, 2H), 5.18 (s, 2H), 6.43 (d, J=9.0 Hz, 1H), 7.44-7.49 (m, 3H), 7.53 (s, 1H), 7.59 (d, J=9.0 Hz, 1H), 7.62 (dd, J=1.6, 2.3 Hz, 1H), 8.63 (dd, J=1.6, 2.3 Hz, 2H), 12.75 (s, 1H).

Preparation 162

Synthesis of 5-(3-((4-acetyl-2-ethyl-3-hydroxyphenoxy)methyl)phenylthio)nicotinonitrile Using the method of Preparation 160 using 5-(3-(hydroxymethyl)phenylthio) nicotinonitrile (3.90 g, 16.1 mmol) and 1-(3-ethyl-2,4-dihydroxyphenyl)ethanone (2.90 g, 16.1 mmol) affords the title compound (2.20 g, 34%): $^1$H NMR (CDCl$_3$) δ 1.10 (t, J=7.4 Hz, 3H), 2.57 (s, 3H), 2.71 (q, J=7.4 Hz, 2H), 5.18 (s, 2H), 6.43 (d, J=9.0 Hz, 1H), 7.44-7.49 (m, 3H), 7.51 (s, 1H), 7.59 (d, J=9.0 Hz, 1H), 7.63 (dd, J=2.0, 2.3 Hz, 1H), 8.64 (t, J=2.0 Hz, 2H), 12.75 (s, 1H).

Preparation 163

Synthesis of 5-(4-((4-acetyl-3-hydroxy-2-methylphenoxy)methyl)phenylthio)nicotinonitrile Using the method of Preparation 160 using 5-(4-(hydroxymethyl)phenylthio) nicotinonitrile (1.20 g, 4.95 mmol) and 1-(2,4-dihydroxy-3-methylphenyl)ethanone (0.86 g, 5.20 mmol) affords the title compound (787 mg, 41%): $^1$H NMR (d$_6$-DMSO) δ 2.06 (s, 3H), 2.58 (s, 3H), 5.30 (s, 2H), 6.72 (d, J=9.0 Hz, 1H), 7.51-7.55 (m, 4H), 7.81 (d, J=9.0 Hz, 1H), 8.23 (t, J=2.0 Hz, 1H), 8.72 (d, J=2.0 Hz, 2H), 8.91 (d, J=2.0 Hz, 1H), 12.85 (s, 1H).

Preparation 164

Synthesis of 5-(4-((4-acetyl-3-hydroxy-2-propylphenoxy)methyl)phenylthio)nicotinonitrile Using the method of Preparation 160 using 5-(4-(hydroxymethyl)phenylthio) nicotinonitrile (1.20 g, 4.95 nmol) and 1-(2,4-dihydroxy-3-propylphenyl)ethanone (1.01 g, 5.20 mmol) affords the title compound. MS (APCI-neg) m/z (rel intensity): 417 (M−H, 100%).

Preparation 165

Synthesis of 5-(4-((4-acetyl-2-ethyl-3-hydroxyphenoxy)methyl)phenylthio)nicotinonitrile Using the method of Preparation 160 using 5-(4-(hydroxymethyl)phenylthio) nicotinonitrile (1.20 g, 4.95 mmol) and 1-(3-ethyl-2,4-dihydroxyphenyl)ethanone (937 mg, 5.20 mmol) affords the title compound (750 mg, 37%): $^1$H NMR (CDCl$_3$) δ 1.15 (t, J=7.64 Hz, 3H), 2.57 (s, 3H), 2.76 (q, J=7.6 Hz, 2H), 5.22 (s, 2H), 6.47 (d, J=9.0 Hz, 1H), 7.49 (d, J=8.2 Hz, 2H),), 7.52 (d, J=8.2 Hz, 2H), 7.60 (d, J=9.0 Hz, 1H), 7.63 (dd, J=2.0, 2.3 Hz, 1H), 8.64 (t, J=2.0 Hz, 2H), 12.75 (s, 1H).

Preparation 166

Synthesis of 5-(3-((4-acetyl-3-hydroxy-2-methylphenoxy)methyl)phenylthio) picolinonitrile

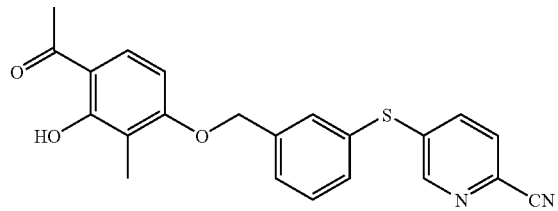

Add triphenylphosphine (1.84 g, 7.02 mmol) and diisopropylazodicarboxylate (1.42 g, 7.02 mmol) to a solution of 5-(3-(hydroxymethyl)phenylthio)picolinonitrile (1.70 g, 7.02 mmol) and 1-(2,4-dihydroxy-3-methylphenyl)ethanone (1.17 g, 7.02 mmol) in THF (35.1 mL). Stir overnight. Dilute with ethyl acetate. Wash the mixture with water and brine. Dry, filter and concentrate to afford the title compound (2.00 g, 73%). Use as is. MS (APCI-neg) m/z (rel intensity): 390 (M+H, 100%).

Preparation 167

Synthesis of 5-(3-((4-acetyl-2-ethyl-3-hydroxyphenoxy)methyl)phenylthio) picolinonitrile Using the method of Preparation 166 using 5-(3-(hydroxymethyl)phenylthio) picolinonitrile (1.70 g, 7.02 mmol) and 1-(3-ethyl-2,4-dihydroxyphenyl)ethanone (1.26 g, 7.02 mmol) affords the title compound (2.20 g, 78%). MS (APCI-neg) m/z (rel intensity): 403 (M−H, 100%).

Preparation 168

Synthesis of 5-(3-((4-acetyl-3-hydroxy-2-propylphenoxy)methyl)phenylthio) picolinonitrile Using the method of Preparation 166 using 5-(3-(hydroxymethyl)phenylthio) picolinonitrile (1.70 g, 7.02 mmol) and 1-(2,4-dihydroxy-3-propylphenyl)ethanone (1.36 g, 7.02 mmol) affords the title compound (1.25 g, 43%). MS (APCI-neg) m/z (rel intensity): 417 (M−H, 100%).

Preparation 169

Synthesis of 5-(4-((4-Acetyl-3-hydroxy-2-methylphenoxy)methyl)phenylthio) picolinonitrile Using the method of Preparation 166 using 5-(4-(hydroxymethyl)phenylthio) picolinonitrile (1.90 g, 7.84 mmol) and 1-(2,4-dihydroxy-3-methylphenyl)ethanone (1.30 g, 7.84 mmol) affords the title compound (1.98 g, 65%). MS (APCI-neg) m/z (rel intensity): 389 (M−H, 100%).

Preparation 170

Synthesis of 6-(3-((4-acetyl-3-hydroxy-2-propylphenoxy)methyl)phenylthio) nicotinonitrile Using the method of Preparation 166 using 6-(3-(hydroxymethyl)phenylthio) nicotinonitrile (1.25 g, 5.15 mmol) and 1-(2,4-dihydroxy-3-propylphenyl)ethanone (1.00 g, 5.15 mmol) affords the title compound (3.00 g). MS (APCI-neg) m/z (rel intensity): 417 (M−H, 100%).

Preparation 171

Synthesis of 6-(3-((4-acetyl-3-hydroxy-2-methylphenoxy)methyl)phenylthio) nicotinonitrile Using the method of Preparation 166 using 6-(3-(hydroxymethyl)phenylthio) nicotinonitrile (1.46 g, 6.02 mmol) and 1-(2,4-dihydroxy-3-methylphenyl)ethanone (1.00 g, 6.02 mmol) affords the title compound (3.00 g). MS (APCI-neg) m/z (rel intensity): 389 (M−H, 100%).

Preparation 172

Synthesis of 2-(3-((4-acetyl-3-hydroxy-2-methylphenoxy)methyl)phenylthio) isonicotinonitrile Using the method of Preparation 166 using 2-(3-(hydroxymethyl)phenylthio) isonicotinonitrile (1.46 g, 6.02 mmol) and 1-(2,4-dihydroxy-3-methylphenyl)ethanone (1.00 g, 6.02 mmol) affords the title compound (1.22 g, 52%). MS (APCI-neg) m/z (rel intensity): 389 (M−H, 100%).

Preparation 173

Synthesis of 2-(3-((4-acetyl-3-hydroxy-2-propylphenoxy)methyl)phenylthio) isonicotinonitrile Using the method of Preparation 166 using 2-(3-(hydroxymethyl)phenylthio) isonicotinonitrile (1.25 g, 5.15 mmol) and 1-(2,4-dihydroxy-3-propylphenyl)ethanone (1.00 g, 5.15 mmol) affords the title compound (1.75 g, 81%). MS (APCI-neg) m/z (rel intensity): 417 (M−H, 100%).

Preparation 174

Synthesis of 6-(3-((4-acetyl-2-ethyl-3-hydroxyphenoxy)methyl)phenylthio) isonicotinonitrile Using the method of Preparation 166 using 6-(3-(hydroxymethyl)phenylthio) isonicotinonitrile (1.35 g, 5.56 mmol) and 1-(3-ethyl-2,4-dihydroxyphenyl)ethanone (1.00 g, 5.56 mmol) affords the title compound (1.80 g, 80%). MS (APCI-neg) m/z (rel intensity): 403 (M−H, 100%).

Preparation 175

Synthesis of 6-(4-((4-acetyl-3-hydroxy-2-methylphenoxy)methyl)phenylthio) isonicotinonitrile Using the method of Preparation 166 using 6-(4-(hydroxymethyl)phenylthio) isonicotinonitrile (1.10 g, 4.54 mmol) and 1-(2,4-dihydroxy-3-methylphenyl)ethanone (754 mg, 4.54 mmol) affords the title compound (1.23 g, 69%). MS (APCI-neg) m/z (rel intensity): 389 (M–H, 100%).

Preparation 176

Synthesis of 6-(4-((4-acetyl-2-ethyl-3-hydroxyphenoxy)methyl)phenylthio) isonicotinonitrile Using the method of Preparation 166 using 6-(4-(hydroxymethyl)phenylthio) isonicotinonitrile (1.10 g, 4.54 mmol) and 1-(3-ethyl-2,4-dihydroxyphenyl)ethanone (818 mg, 4.54 mmol) affords the title compound (1.84 g, quant.). MS (APCI-neg) m/z (rel intensity): 403 (M–H, 100%).

Preparation 177

Synthesis of 6-(4-((4-acetyl-3-hydroxy-2-propylphenoxy)methyl)phenylthio) isonicotinonitrile Using the method of Preparation 166 using 6-(4-(hydroxymethyl)phenylthio) isonicotinonitrile (1.00 g, 4.13 mmol) and 1-(3-ethyl-2,4-dihydroxyphenyl)ethanone (802 mg, 4.13 mmol) affords the title compound (1.50 g, 87%). MS (APCI-neg) m/z (rel intensity): 417 (M–H, 100%).

EXAMPLE 71

Synthesis of 5-(3-((4-acetyl-3-hydroxy-2-methylphenoxy)methyl)phenylthio)nicotinic acid

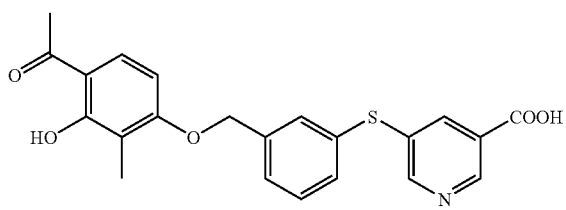

Add LiOH monohydrate (1.29 g, 30.7 mmol) to a solution of 5-(3-((4-acetyl-3-hydroxy-2-methylphenoxy)methyl)phenylthio)nicotinonitrile (1.20 g, 3.07 mmol) in a mixture of dioxane (30 mL) and water (15 mL). Heat the mixture at reflux for 2.5 h. Cool to room temperature. Add 17 mL of 2.0 M HCl aq. solution (pH 2-3). Extract with EtOAc. Dry, filter and concentrate. Add EtOAc (30 mL) and CH$_2$Cl$_2$ (15 mL) to the white solid. Sonicate for 2 min. Filter to afford the title compound (1.25 g, 99%): $^1$H NMR (d$_6$-DMSO) δ 1.96 (s, 3H), 2.58 (s, 3H), 5.26 (s, 2H), 6.68 (d, J=9.0 Hz, 1H), 7.42-7.50 (m, 4H), 7.78 (d, J=9.0 Hz, 1H), 8.06 (t, J=2.0 Hz, 1H), 8.74 (d, J=2.3 Hz, 1H), 8.95 (d, J=1.6 Hz, 1H), 12.83 (s, 1H), 13.62 (s, 1H); MS (APCI-neg mode) m/z (rel intensity): 408 (M–H, 100%).

EXAMPLE 72

Synthesis of 5-(3-((4-acetyl-3-hydroxy-2-propylphenoxy)methyl)phenylthio)nicotinic acid

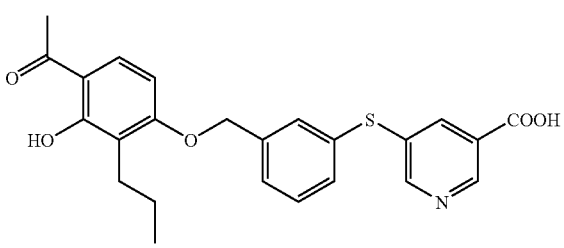

Using the method of Example 71 using 5-(3-((4-acetyl-3-hydroxy-2-propylphenoxy) methyl)phenylthio)nicotinonitrile (1.29 g, 3.08 mmol) affords the title compound (1.35 g, quant.): $^1$H NMR (CDCl$_3$) δ 0.91 (t, J=7.4 Hz, 3H), 1.48-1.58 (m, 2H), 2.55 (s, 3H), 2.65 (t, J=7.6 Hz, 2H), 5.15 (s, 2H), 6.42 (d, J=9.0 Hz, 1H), 7.39-7.42 (m, 3H), 7.46 (s, 1H), 7.56 (d, J=9.0 Hz, 1H), 8.22 (dd, J=2.0, 2.3 Hz, 1H), 8.71 (d, J=2.3 Hz, 1H), 9.10 (d, J=2.0 Hz, 1H), 12.73 (s, 1H); MS (APCI-neg mode) m/z (rel intensity): 436 (M–H, 100%).

EXAMPLE 73

Synthesis of 5-(3-((4-acetyl-2-ethyl-3-hydroxyphenoxy)methyl)phenylthio)nicotinic acid

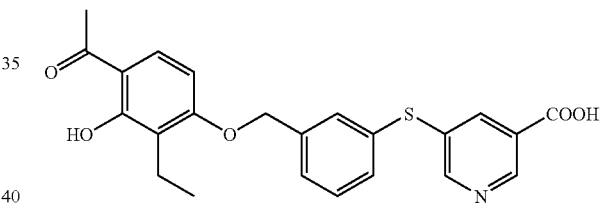

Using the method of Example 71 using 5-(3-((4-acetyl-2-ethyl-3-hydroxyphenoxy)methyl)phenylthio)nicotinonitrile (1.02 g, 2.52 mmol) affords the title compound (1.04 g, 97%): $^1$H NMR (CDCl$_3$) δ 1.08 (t, J=7.4 Hz, 3H), 2.56 (s, 3H), 2.69 (q, J=7.4 Hz, 2H), 5.15 (s, 2H), 6.42 (d, J=9.0 Hz, 1H), 7.39-7.42 (m, 3H), 7.44 (s, 1H), 7.56 (d, J=9.0 Hz, 1H), 8.21 (dd, J=2.0, 2.3 Hz, 1H), 8.71 (d, J=2.3 Hz, 1H), 9.09 (d, J=2.0 Hz, 1H), 12.73 (s, 1H); MS (APCI-neg mode) m/z (rel intensity): 422 (M–H, 100%).

EXAMPLE 74

Synthesis of 5-(4-((4-acetyl-3-hydroxy-2-methylphenoxy)methyl)phenylthio)nicotinic acid

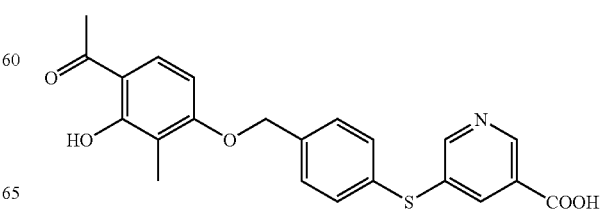

Using the method of Example 71 using 5-(4-((4-acetyl-3-hydroxy-2-methylphenoxy)methyl)phenylthio)nicotinonitrile (787 mg, 2.02 mmol) affords the title compound (790 mg, 96%): $^1$H NMR (d$_6$-DMSO) δ 2.05 (s, 3H), 2.58 (s, 3H), 5.30 (s, 2H), 6.72 (d, J=9.0 Hz, 1H), 7.50-7.55 (m, 4H), 7.81 (d, J=9.0 Hz, 1H), 8.02 (dd, J=2.0, 2.3 Hz, 1H), 8.73 (d, J=2.3 Hz, 1H), 8.93 (d, J=2.0 Hz, 1H), 12.85 (s, 1H), 13.61 (s, 1H); MS (APCI-neg mode) m/z (rel intensity): 408 (M−H, 100%).

EXAMPLE 75

Synthesis of 5-(4-((4-acetyl-3-hydroxy-2-propylphenoxy)methyl)phenylthio)nicotinic acid

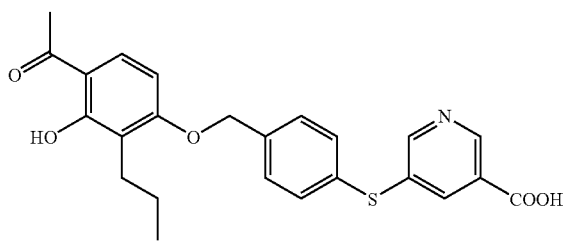

Using the method of Example 71 using 5-(4-((4-acetyl-3-hydroxy-2-propylphenoxy)methyl)phenylthio)nicotinonitrile (2.0 g) affords the title compound (134 mg, 6% (over 2 steps)): $^1$H NMR (CDCl$_3$) δ 0.95 (t, J=7.2 Hz, 3H), 1.53-1.63 (m, 2H), 2.56 (s, 3H), 2.70 (t, J=7.6 Hz, 2H), 5.17 (s, 2H), 6.46 (d, J=9.0 Hz, 1H), 7.45 (q, J=8.6 Hz, 4H), 7.58 (d, J=9.0 Hz, 1H), 8.22 (dd, J=2.0, 2.3 Hz, 1H), 8.70 (d, J=2.3 Hz, 1H), 9.10 (d, J=2.0 Hz, 1H), 12.75 (s, 1H); MS (APCI-neg mode) m/z (rel intensity): 436 (M−H, 100%).

EXAMPLE 76

Synthesis of 5-(4-((4-acetyl-2-ethyl-3-hydroxyphenoxy)methyl)phenylthio)nicotinic acid

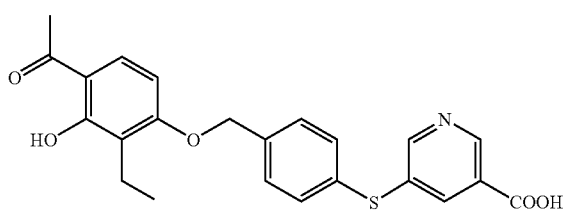

Using the method of Example 71 using 5-(4-((4-acetyl-2-ethyl-3-hydroxyphenoxy)methyl)phenylthio)nicotinonitrile (750 mg, 1.85 mmol) affords the title compound (350 mg, 45%): $^1$H NMR (d$_6$-DMSO) δ 1.04 (t, J=7.4 Hz, 3H), 2.58 (s, 3H), 2.62 (q, J=7.4 Hz, 2H), 5.30 (s, 2H), 6.72 (d, J=9.0 Hz, 1H), 7.52 (s, 4H), 7.81 (d, J=9.0 Hz, 1H), 8.03 (dd, J=2.0, 2.3 Hz, 1H), 8.73 (d, J=2.3 Hz, 1H), 8.93 (d, J=2.0 Hz, 1H), 12.84 (s, 1H); MS (APCI-neg mode) m/z (rel intensity): 422 (M−H, 100%).

EXAMPLE 77

Synthesis of 5-(3-((4-acetyl-3-hydroxy-2-methylphenoxy)methyl)phenylthio)picolinic acid

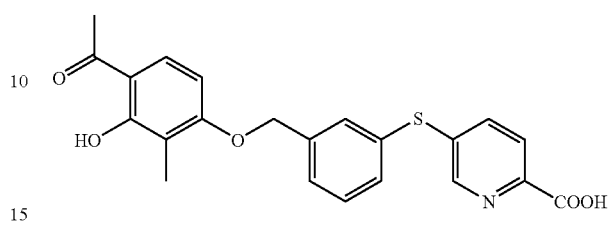

Using the method of Example 71 using 5-(3-((4-acetyl-3-hydroxy-2-methylphenoxy)methyl)phenylthio)picolinonitrile (2.70 g, 6.92 mmol) affords the title compound (mg, %): $^1$H NMR (d$_6$-DMSO) δ 1.98 (s, 3H), 2.58 (s, 3H), 5.27 (s, 2H), 6.69 (d, J=9.0 Hz, 1H), 7.41 (m, 1H), 7.48 (m, 3H), 7.73 (m, 1H), 7.80 (d, J=9.0 Hz, 1H), 7.94 (d, J=8.2 Hz, 1H), 8.48 (s, 1H), 12.85 (s, 1H); MS (APCI-neg mode) m/z (rel intensity): 408 (M−H, 100%).

EXAMPLE 78

Synthesis of 5-(3-((4-acetyl-2-ethyl-3-hydroxyphenoxy)methyl)phenylthio)picolinic acid

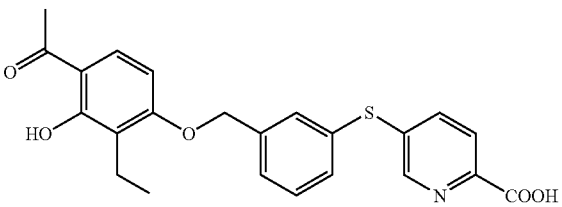

Using the method of Example 71 using 5-(3-((4-acetyl-2-ethyl-3-hydroxy-phenoxy)methyl)phenylthio)picolinonitrile (2.8 g, 6.9 mmol) affords the title compound (2.11 g, 72%): $^1$H NMR (d$_6$-DMSO) δ 0.96 (t, J=7.2 Hz, 3H), 2.54 (q, J=7.4 Hz, 2H), 2.57 (s, 3H), 5.29 (s, 2H), 6.68 (d, J=9.0 Hz, 1H), 7.50-7.53 (m, 4H), 7.72 (m, 1H), 7.80 (d, J=9.0 Hz, 1H), 7.95 (d, J=8.2 Hz, 1H), 8.55 (d, J=2.3 Hz, 1H), 12.83 (s, 1H); MS (APCI-neg mode) m/z (rel intensity): 422 (M−H, 100%).

EXAMPLE 79

Synthesis of 5-(3-((4-acetyl-3-hydroxy-2-propylphenoxy)methyl)phenylthio)picolinic acid

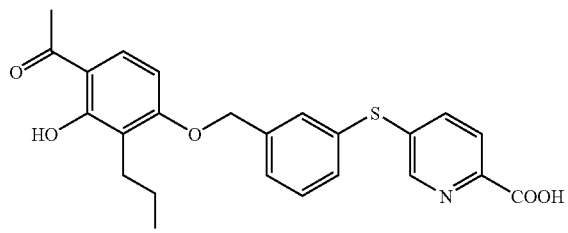

Using the method of Example 71 using 5-(3-((4-acetyl-3-hydroxy-2-propylphenoxy)methyl)phenylthio)picolinonitrile (2.90 g, 6.93 mmol) affords the title compound (1.97 g, 65%): $^1$H NMR (d$_6$-DMSO) δ 0.80 (t, J=7.2 Hz, 3H), 1.46-1.37 (m, 2H), 2.53-2.55 (m, 2H) 2.58 (s, 3H), 5.28 (s, 2H), 6.69 (d, J=9.0 Hz, 1H), 7.44-7.56 (m, 4H), 7.71 (m, 1H), 7.80 (d, J=9.0 Hz, 1H), 7.93 (d, J=8.6 Hz, 1H), 8.53 (s, 1H), 12.84 (s, 1H); MS (APCI-neg mode) m/z (rel intensity): 436 (M−H, 100%).

EXAMPLE 80

Synthesis of 5-(4-((4-acetyl-3-hydroxy-2-methylphenoxy)methyl)phenylthio)picolinic acid

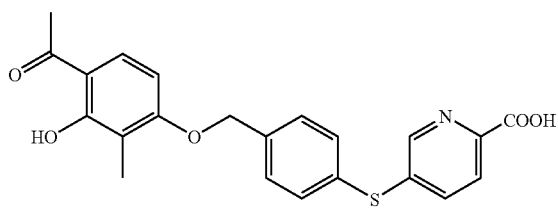

Using the method of Example 71 using 5-(4-((4-acetyl-3-hydroxy-2-methylphenoxy)-methyl)phenylthio)picolinonitrile (3.0 g, 7.7 mmol) affords the title compound (2.25 g, 72%): $^1$H NMR (d$_6$-DMSO) δ 2.06 (s, 3H), 2.59 (s, 3H), 5.32 (s, 2H), 6.74 (d, J=9.0 Hz, 1H), 7.56 (s, 4H), 7.70 (m, 1H), 7.82 (d, J=9.0 Hz, 1H), 7.97 (d, J=8.2 Hz, 1H), 8.52 (m 1H), 12.85 (s, 1H); MS (APCI-neg mode) m/z (rel intensity): 408 (M−H, 100%).

EXAMPLE 81

Synthesis of 6-(3-((4-acetyl-3-hydroxy-2-propylphenoxy)methyl)phenylthio)nicotinic acid

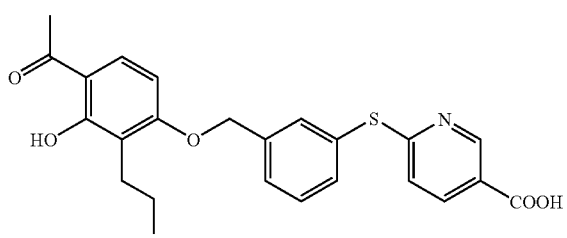

Using the method of Example 71 using 6-(3-((4-acetyl-3-hydroxy-2-propylphenoxy)methyl)phenylthio)nicotinonitrile (2.16 g, 5.15 mmol) affords the title compound (700 mg, 31%): $^1$H NMR (d$_6$-DMSO) δ 0.83 (t, J=7.4 Hz, 3H), 1.46 (q, J=9.9 Hz, 2H), 2.52 (s, 3H), 2.62 (t, J=7.4 Hz, 2H), 5.30 (s, 2H), 6.68 (d, J=9.0 Hz, 1H), 6.91 (d, J=8.6 Hz, 1H), 7.57 (s, 3H), 7.61 (m, 1H), 7.68 (s, 1H), 7.99 (q, J=6.9 Hz, 1H), 8.82 (s, 1H), 13.8 (s, 1H).

EXAMPLE 82

Synthesis of 2-(3-((4-acetyl-3-hydroxy-2-methylphenoxy)methyl)phenylthio)nicotinic acid

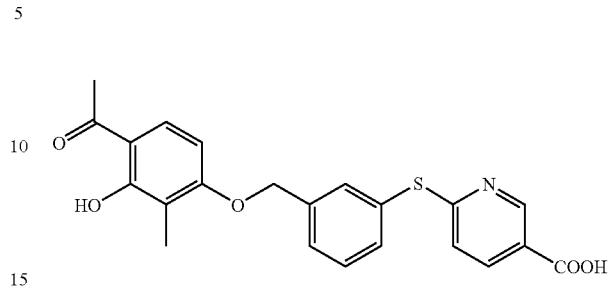

Using the method of Example 71 using 2-(3-((4-acetyl-3-hydroxy-2-methylphenoxy)methyl)phenylthio)nicotinonitrile (2.35 g, 6.02 mmol) affords the title compound (80 mg, 3%): $^1$H NMR (d$_6$-DMSO) δ 2.08 (s, 3H), 2.52 (s, 3H), 5.33 (s, 2H), 6.68 (d, J=9.0 Hz, 1H), 6.85 (d, J=8.2 Hz, 1H), 7.58-7.60 (m, 5H), 7.95 (q, J=7.2 Hz, 1H), 8.79 (d, J=2.0 Hz, 1H), 12.84 (s, 1H), 13.82 (s, 1H); MS (APCI-neg mode) m/z (rel intensity): 408 (M−H, 100%).

EXAMPLE 83

Synthesis of 6-(3-((4-acetyl-3-hydroxy-2-methylphenoxy)methyl)phenylthio)isonicotinic acid

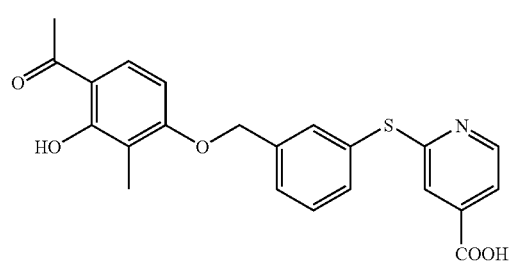

Using the method of Example 71 using 6-(3-((4-acetyl-3-hydroxy-2-methylphenoxy)methyl)phenylthio)isonicotinonitrile (250 mg, 0.640 mmol) affords the title compound (60.5 mg, 23%): $^1$H NMR (d$_6$-DMSO) δ 2.13 (s, 3H), 2.56 (s, 3H), 5.18 (s, 2H), 6.47 (d, J=9.0 Hz, 1H), 7.49 (s, 2H), 7.55 (d, J=5.9 Hz, 2H), 7.58 (s, 2H), 7.65 (s, 1H), 8.59 (d, J=5.1 Hz, 1H), 12.76 (s, 1H); MS (APCI-neg mode) m/z (rel intensity): 408 (M−H, 100%).

EXAMPLE 84

Synthesis of 6-(3-((4-acetyl-3-hydroxy-2-propylphenoxy)methyl)phenylthio)isonicotinic acid

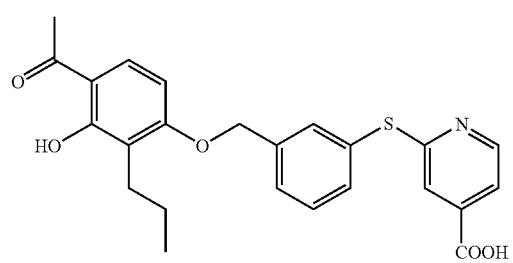

Using the method of Example 71 using 6-(3-((4-acetyl-3-hydroxy-2-propylphenoxy)methyl)phenylthio)isonicotinonitrile (2.16 g, 5.15 mmol) affords the title compound (700 mg, 31%): $^1$H NMR (d$_6$-DMSO) δ 0.78 (t, J=7.4 Hz, 3H), 1.43 (m, 2H), 2.51 (s, 3H), 2.56 (t, J=8.4 Hz, 2H), 5.32 (s, 2H), 6.72 (d, J=9.0 Hz, 1H), 7.35 (s, 1H), 7.57 (m, 4H), 7.70 (s, 1H), 7.81 (d, J=9.0 Hz, 1H), 8.59 (d, J=5.1 Hz, 1H), 12.84 (s, 1H); MS (APCI-neg mode) m/z (rel intensity): 436 (M−H, 100%).

EXAMPLE 85

Synthesis of 6-(3-((4-acetyl-2-ethyl-3-hydroxyphenoxy)methyl)phenylthio)isonicotinic acid

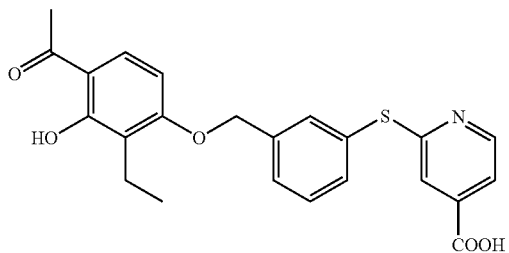

Using the method of Example 71 using 6-(3-((4-acetyl-2-ethyl-3-hydroxyphenoxy)methyl)phenylthio)isonicotinonitrile (2.25 g, 5.55 mmol) affords the title compound (750 mg, 32%): $^1$H NMR (d$_6$-DMSO) δ 0.98 (t, J=7.4 Hz, 3H), 2.50 (s, 3H), 2.57 (m, 2H), 5.32 (s, 2H), 6.71 (d, J=9.0 Hz, 1H), 7.36 (s, 1H), 7.56 (m, 4H), 7.69 (s, 1H), 7.80 (d, J=9.0 Hz, 1H), 8.59 (d, J=5.1 Hz, 1H), 12.83 (s, 1H); MS (APCI-neg mode) m/z (rel intensity): 422 (M−H, 100%).

EXAMPLE 86

Synthesis of 6-(4-((4-acetyl-3-hydroxy-2-methylphenoxy)methyl)phenylthio)isonicotinic acid

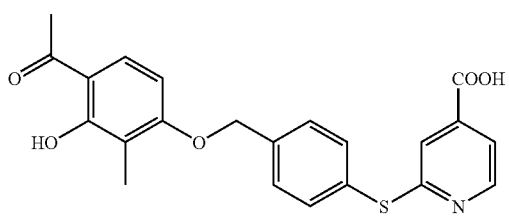

Using the method of Example 71 using 6-(4-((4-acetyl-3-hydroxy-2-methylphenoxy)methyl)phenylthio)isonicotinonitrile (1.77 g, 4.54 mmol) affords the title compound (750 mg, 40%): $^1$H NMR (d$_6$-DMSO) δ 2.08 (s, 3H), 2.59 (s, 3H), 5.36 (s, 2H), 6.75 (d, J=9.0 Hz, 1H), 7.35 (s, 1H), 7.54 (m, 1H), 7.61 (d, J=8.2 Hz, 2H), 7.67 (d, J=8.2 Hz, 2H), 7.83 (d, J=9.0 Hz, 1H), 8.59 (d, J=5.1 Hz, 1H), 12.86 (s, 1H); MS (APCI-neg mode) m/z (rel intensity): 408 (M−H, 100%).

EXAMPLE 87

Synthesis of 6-(4-((4-acetyl-2-ethyl-3-hydroxyphenoxy)methyl)phenylthio)isonicotinic acid

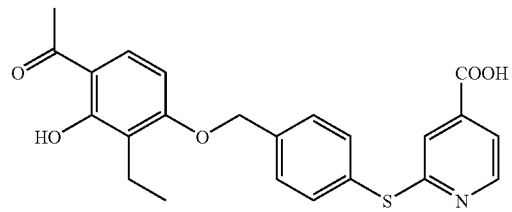

Using the method of Example 71 using 6-(4-((4-acetyl-2-ethyl-3-hydroxyphenoxy)methyl)phenylthio)isonicotinonitrile (1.84 g, 4.54 mmol) affords the title compound (300 mg, 16%): $^1$H NMR (d$_6$-DMSO) δ 1.07 (t, J=7.4 Hz, 3H), 2.50 (s, 3H), 2.65 (q, J=9.9 Hz, 2H), 5.36 (s, 2H), 6.74 (d, J=9.0 Hz, 1H), 7.35 (s, 1H), 7.55 (d, J=5.1 Hz, 1H), 7.59 (d, J=8.2 Hz, 2H), 7.67 (d, J=8.2 Hz, 2H), 7.82 (d, J=9.0 Hz, 1H), 8.59 (d, J=5.1 Hz, 1H), 12.85 (s, 1H); MS (APCI-neg mode) m/z (rel intensity): 422 (M−H, 100%).

EXAMPLE 88

Synthesis of 6-(4-((4-acetyl-3-hydroxy-2-propylphenoxy)methyl)phenylthio)isonicotinic acid

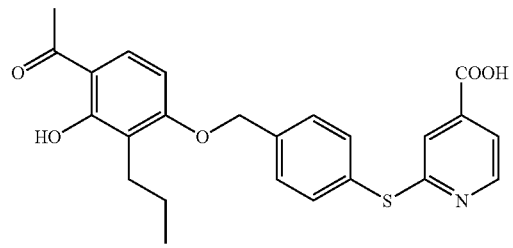

Using the method of Example 71 using 6-(4-((4-acetyl-3-hydroxy-2-propyl-phenoxy)methyl)phenylthio)isonicotinonitrile (1.73 g, 4.13 mmol) affords the title compound (350 mg, 19%): $^1$H NMR (d$_6$-DMSO) δ 0.89 (t, J=7.4 Hz, 3H), 1.51 (q, J=9.9 Hz, 2H), 2.59 (s, 3H), 2.62 (t, J=7.4 Hz, 2H), 5.35 (s, 2H), 6.74 (d, J=9.4 Hz, 1H), 7.35 (m, 2H), 7.58 (d, J=8.2 Hz, 2H), 7.67 (d, J=8.2 Hz, 2H), 7.83 (d, J=9.0 Hz, 1H), 8.59 (d, J=5.1 Hz, 1H), 12.86 (s, 1H); MS (APCI-neg mode) m/z (rel intensity): 436 (M−H, 100%).

EXAMPLE 89

Synthesis of 5-(3-((4-acetyl-3-hydroxy-2-methylphenoxy)methyl)phenylsulfinyl)nicotinic acid

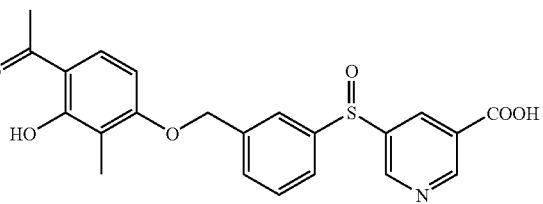

Add a 0.5 M solution of potassium peroxymonosulfate (0.61 g, 1.00 mmol) in water (2.0 mL) to a solution of 5-(3-((4-acetyl-3-hydroxy-2-methylphenoxy)methyl)phenylthio)nicotinic acid (205 mg, 0.50 mmol) in methanol (7.5 mL) at 0° C. Allow the solution to warm to room temperature and stir for 1.5 d. Add water and 2.2 mL of 2.0 M HCl to the mixture. Extract the mixture with EtOAc. Dry, filter and concentrate. Recrystallize the residue from a mixture of $CH_2Cl_2$ and hexanes to give a light yellow solid. Purify the yellow solid by flash chromatograhpy on silica gel eluting with a mixture of acetone, hexanes, and acetic acid (50:50:1 to 90:10) to afford the title compound (31 mg, 15%): $^1$H NMR (d$_6$-DMSO) δ 2.01 (s, 3H), 2.58 (s, 3H), 5.33 (s, 2H), 6.67 (d, J=9.0 Hz, 1H), 7.61-7.63 (m, 2H), 7.77 (d, J=9.0 Hz, 1H), 7.81-7.83 (m, 1H), 7.88 (s, 1H), 8.49 (t, J=2.0 Hz, 1H), 9.08 (d, J=2.0 Hz, 1H), 9.12 (d, J=2.0 Hz, 1H), 12.84 (s, 1H); MS (APCI-neg mode) m/z (rel intensity): 424 (M−H, 100%).

EXAMPLE 90

Synthesis of 5-(3-((4-acetyl-3-hydroxy-2-propylphenoxy)methyl)phenylsulfinyl)nicotinic acid

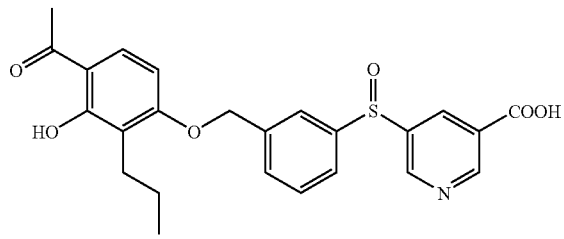

Using the method of Example 89 using 5-(3-((4-acetyl-3-hydroxy-2-propyl-phenoxy)methyl)phenylthio)nicotinic acid (219 mg, 0.50 mmol) affords the title compound (90 mg, 40%): $^1$H NMR (CDCl$_3$) δ 0.93 (t, J=7.2 Hz, 3H), 1.50-1.60 (m, 2H), 2.56 (s, 3H), 2.67 (t, J=7.6 Hz, 2H), 5.20 (s, 2H), 6.39 (d, J=9.0 Hz, 1H), 7.55 (d, J=9.0 Hz, 1H), 7.57-7.58 (m, 2H), 7.69 (dt, J=1.6, 4.3 Hz, 1H), 7.76 (s, 1H), 8.64 (t, J=2.0 Hz, 1H), 8.99 (d, J=2.0 Hz, 1H), 9.32 (d, J=2.0 Hz, 1H), 12.73 (s, 1H); MS (APCI-neg mode) m/z (rel intensity): 452 (M−H, 100%).

EXAMPLE 91

Synthesis of 5-(3-((4-acetyl-2-ethyl-3-hydroxyphenoxy)methyl)phenylsulfinyl)nicotinic acid

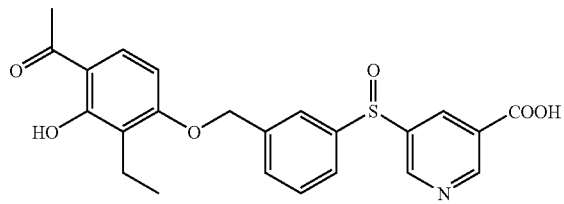

Using the method of Example 89 using 5-(3-((4-acetyl-2-ethyl-3-hydroxyphenoxy)methyl)phenylthio)nicotinic acid (212 mg, 0.50 mmol) affords the title compound (50 mg, 23%): $^1$H NMR (d$_6$-DMSO) δ 1.00 (t, J=7.4 Hz, 3H), 2.57 (s, 3H), 2.57 (q, J=7.4 Hz, 2H), 5.33 (s, 2H), 6.67 (d, J=9.0 Hz, 1H), 7.61-7.63 (m, 2H), 7.76 (d, J=9.4 Hz, 1H), 7.82-7.85 (m, 1H), 7.87 (s, 1H), 8.48 (dd, J=2.0, 2.3 Hz, 1H), 9.08 (d, J=2.3 Hz, 1H), 9.11 (d, J=2.0 Hz, 1H), 12.83 (s, 1H), 13.83 (s, 1H); MS (APCI-neg mode) m/z (rel intensity): 438 (M−H, 100%).

EXAMPLE 92

Synthesis of 5-(4-((4-acetyl-3-hydroxy-2-methylphenoxy)methyl)phenylsulfinyl)nicotinic acid

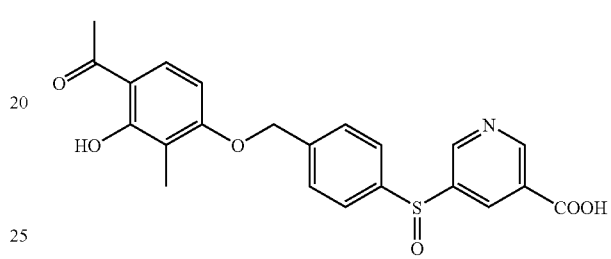

Using the method of Example 89 using 5-(4-((4-acetyl-3-hydroxy-2-methyl-phenoxy)methyl)phenylthio)nicotinic acid (205 mg, 0.50 mmol) affords the title compound (100 mg, 47%): $^1$H NMR (d$_6$-DMSO) δ 2.04 (s, 3H), 2.57 (s, 3H), 5.32 (s, 2H), 6.69 (d, J=9.0 Hz, 1H), 7.65 (d, J=8.2 Hz, 2H), 7.79 (d, J=9.4 Hz, 1H), 7.87 (d, J=8.2 Hz, 2H), 8.50 (dd, J=2.0, 2.3 Hz, 1H), 9.12 (d, J=2.3 Hz, 1H), 9.13 (d, J=2.0 Hz, 1H), 12.84 (s, 1H); MS (APCI-neg mode) m/z (rel intensity): 424 (M−H, 100%).

EXAMPLE 93

Synthesis of 5-(4-((4-acetyl-2-ethyl-3-hydroxyphenoxy)methyl)phenylsulfinyl)nicotinic acid

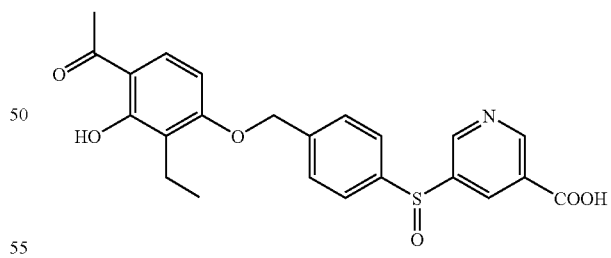

Using the method of Example 89 using 5-(4-((4-acetyl-2-ethyl-3-hydroxyphenoxy)methyl)phenylthio)nicotinic acid (126 mg, 0.30 mmol) affords the title compound (20 mg, 15%): $^1$H NMR (d$_6$-DMSO) δ 1.03 (t, J=7.4 Hz, 3H), 2.56 (s, 3H), 2.62 (q, J=7.4 Hz, 2H), 5.32 (s, 2H), 6.69 (d, J=9.0 Hz, 1H), 7.64 (d, J=8.6 Hz, 2H), 7.79 (d, J=9.0 Hz, 1H), 7.88 (d, J=8.6 Hz, 2H), 8.50 (dd, J=2.0, 2.3 Hz, 1H), 9.12 (d, J=2.3 Hz, 1H), 9.13 (d, J=2.0 Hz, 1H), 12.83 (s, 1H), 13.82 (s, 1H); MS (APCI-neg mode) m/z (rel intensity): 438 (M−H, 100%).

EXAMPLE 94

Synthesis of 6-(3-((4-acetyl-3-hydroxy-2-methylphenoxy)methyl)phenylsulfinyl) isonicotinic acid

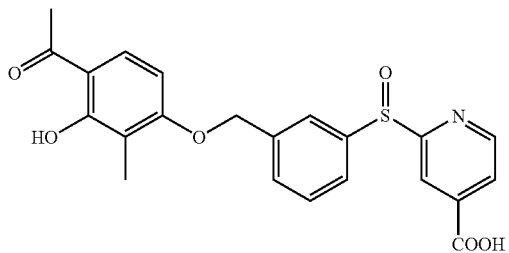

Using the method of Example 89 using 6-(3-((4-acetyl-3-hydroxy-2-methyl)phenoxy)methyl)phenylthio)isonicotinic acid (130 mg, 0.317 mmol) affords the title compound (40.2 mg, 30%): $^1$H NMR (d$_6$-acetone) δ 2.10 (s, 3H), 2.58 (s, 3H), 5.34 (s, 2H), 6.66 (d, J=9.0 Hz, 1H), 7.59-7.64 (m, 2H), 7.75 (d, J=9.4 Hz, 1H), 7.81 (d, J=7.4 Hz, 1H), 7.94 (s, 2H), 8.51 (s, 1H), 8.78 (d, J=5.1 Hz, 1H), 12.89 (s, 1H); MS (APCI-neg mode) m/z (rel intensity): 424 (M−H, 100%).

EXAMPLE 95

Synthesis of 6-(3-((4-acetyl-2-ethyl-3-hydroxyphenoxy)methyl)phenylsulfinyl) isonicotinic acid

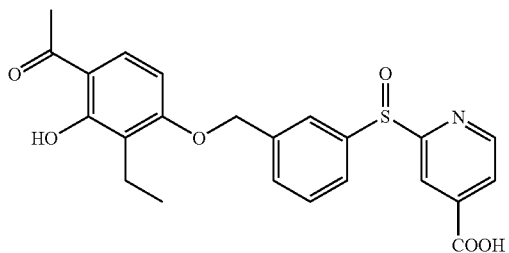

Using the method of Example 89 using 6-(3-((4-acetyl-2-ethyl-3-hydroxy-phenoxy)methyl)phenylthio)isonicotinic acid (200 mg, 0.472 mmol) affords the title compound (18 mg, 9%): $^1$H NMR (d$_6$-DMSO) δ 1.02 (t, J=7.4 Hz, 3H), 2.57 (m, 2H), 2.57 (s, 3H), 5.32 (s, 2H), 6.66 (d, J=9.0 Hz, 1H), 7.59 (d, J=5.1 Hz, 2H), 7.74 (m, 3H), 7.84 (d, J=5.1 Hz, 1H), 8.31 (s, 1H), 8.71 (d, J=4.7 Hz, 1H), 12.83 (s, 1H); MS (APCI-neg mode) m/z (rel intensity): 438 (M−H, 100%).

EXAMPLE 96

Synthesis of 5-(3-((4-acetyl-3-hydroxy-2-methylphenoxy)methyl)phenylsulfonyl)nicotinic acid

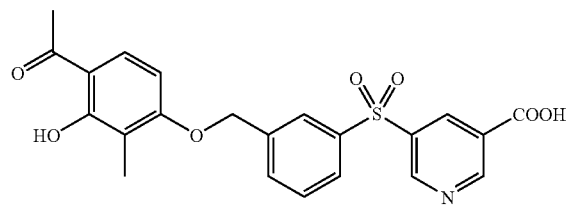

Add a 0.5 M solution of potassium peroxymonosulfate (1.54 g, 2.50 mmol) in water (5.0 mL) to a solution of 5-(3-((4-acetyl-3-hydroxy-2-methylphenoxy)methyl)phenylthio)nicotinic acid (205 mg, 0.50 mmol) in methanol (7.5 mL) at room temperature. Heat the reaction mixture at 40° C. for 3 d. Add a 0.5 M solution of potassium peroxymonosulfate (1.54 g, 2.50 mmol) in water (5.0 mL) and DMF (10 mL) to the mixture. Heat the mixture at 80° C. for 19 h. Cool to room temp. Add water and 0.50 mL of 2.0 M HCl to the mixture. Extract the mixture with EtOAc. Dry, filter and concentrate. Purify the residue by flash chromatograhpy on silica gel eluting with a mixture of acetone, CH$_2$Cl$_2$, and acetic acid (20:80:1) to afford the title compound (74 mg, 34%): $^1$H NMR (d$_6$-DMSO) δ 2.03 (s, 3H), 2.58 (s, 3H), 5.37 (s, 2H), 6.70 (d, J=9.4 Hz, 1H), 7.71 (t, J=7.8 Hz, 1H), 7.79 (d, J=9.0 Hz, 1H), 7.82 (d, J=7.8 Hz, 1H), 8.07 (d, J=7.8 Hz, 1H), 8.16 (s, 1H), 8.63 (dd, J=2.0, 2.3 Hz, 1H), 9.28 (d, J=2.0 Hz, 1H), 9.35 (d, J=2.3 Hz, 1H), 12.84 (s, 1H); MS (APCI-neg mode) m/z (rel intensity): 440 (M−H, 100%).

EXAMPLE 97

Synthesis of 5-(3-((4-acetyl-3-hydroxy-2-propylphenoxy)methyl)phenylsulfonyl)nicotinic acid

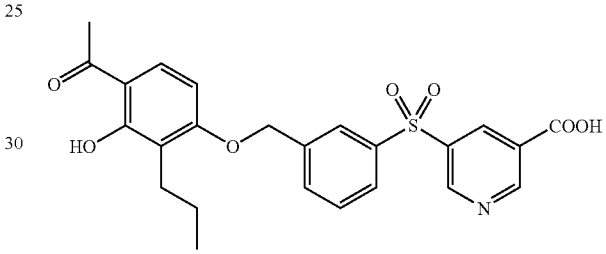

Using the method of Example 96 using 5-(3-((4-acetyl-3-hydroxy-2-propylphenoxy)methyl)phenylthio)nicotinic acid (219 mg, 0.50 mmol) affords the title compound (135 mg, 58%): $^1$H NMR (CDCl$_3$) δ 0.95 (t, J=7.2 Hz, 3H), 1.52-1.62 (m, 2H), 2.57 (s, 3H), 2.69 (t, J=7.6 Hz, 2H), 5.22 (s, 2H), 6.41 (d, J=9.0 Hz, 1H), 7.57 (d, J=8.6 Hz, 1H), 7.63 (t, J=7.8 Hz, 1H), 7.70 (d, J=7.4 Hz, 1H), 7.99 (d, J=8.2 Hz, 1H), 8.05 (s, 1H), 8.83 (dd, J=2.0, 2.3 Hz, 1H), 9.32 (d, J=2.0 Hz, 1H), 9.42 (d, J=2.0 Hz, 1H), 12.74 (s, 1H); MS (APCI-neg mode) m/z (rel intensity): 468 (M−H, 100%).

EXAMPLE 98

Synthesis of 5-(3-((4-acetyl-2-ethyl-3-hydroxyphenoxy)methyl)phenylsulfonyl)nicotinic acid

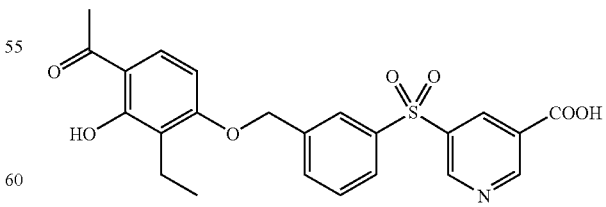

Using the method of Example 96 using 5-(3-((4-acetyl-2-ethyl-3-hydroxyphenoxy)methyl)phenylthio)nicotinic acid (212 mg, 0.50 mmol) affords the title compound (130 mg, 57%): $^1$H NMR (d$_6$-DMSO) δ 1.03 (t, J=7.4 Hz, 3H), 2.57 (s, 3H), 2.60 (q, J=7.4 Hz, 2H), 5.38 (s, 2H), 6.69 (d, J=9.4 Hz, 1H), 7.72 (t, J=7.8 Hz, 1H), 7.79 (d, J=9.0 Hz, 1H), 7.81 (d, J=7.8 Hz, 1H), 8.08 (d, J=7.8 Hz, 1H), 8.15 (s, 1H), 8.62 (dd, J=2.0, 2.3 Hz, 1H), 9.28 (d, J=2.0 Hz, 1H), 9.33 (d, J=2.3 Hz, 1H), 12.84 (s, 1H); MS (APCI-neg mode) m/z (rel intensity): 454 (M–H, 100%).

EXAMPLE 99

Synthesis of 5-(4-((4-acetyl-3-hydroxy-2-methylphenoxy)methyl)phenylsulfonyl) nicotinic acid

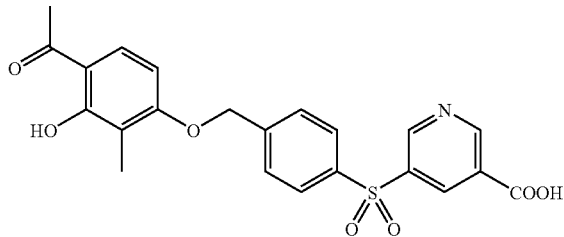

Using the method of Example 96 using 5-(4-((4-acetyl-3-hydroxy-2-methylphenoxy)methyl)phenylthio)nicotinic acid (205 mg, 0.50 mmol) affords the title compound (145 mg, 66%): $^1$H NMR (d$_6$-DMSO) δ 2.06 (s, 3H), 2.57 (s, 3H), 5.38 (s, 2H), 6.68 (d, J=9.0 Hz, 1H), 7.72 (d, J=8.2 Hz, 2H), 7.79 (d, J=9.0 Hz, 1H), 8.14 (d, J=8.2 Hz, 2H), 8.63 (t, J=2.0 Hz, 1H), 9.28 (d, J=2.0 Hz, 1H), 9.38 (d, J=2.3 Hz, 1H), 12.84 (s, 1H), 14.01 (s, 1H); MS (APCI-neg mode) m/z (rel intensity): 440 (M–H, 100%).

EXAMPLE 100

Synthesis of 5-(4-((4-acetyl-3-hydroxy-2-propylphenoxy)methyl)phenylsulfonyl) nicotinic acid

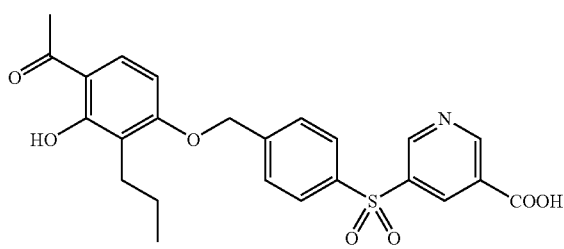

Using the method of Example 96 using 5-(4-((4-acetyl-3-hydroxy-2-propylphenoxy)methyl)phenylthio)nicotinic acid (75 mg, 0.17 mmol) affords the title compound (46 mg, 57%): $^1$H NMR (d$_6$-DMSO) δ0.88 (t, J=7.4 Hz, 3H), 1.44-1.54 (m, 2H), 2.56 (s, 3H), 2.61 (t, J=7.6 Hz, 2H), 5.38 (s, 2H), 6.67 (d, J=9.0 Hz, 1H), 7.70 (d, J=8.2 Hz, 2H), 7.79 (d, J=9.0 Hz, 1H), 8.16 (d, J=8.6 Hz, 2H), 8.64 (t, J=2.0 Hz, 1H), 9.28 (d, J=1.7 Hz, 1H), 9.38 (d, J=2.3 Hz, 1H), 12.84 (s, 1H), 14.02 (s, 1H); MS (APCI-neg mode) m/z (rel intensity): 468 (M–H, 100%).

EXAMPLE 101

Synthesis of 5-(4-((4-acetyl-2-ethyl-3-hydroxyphenoxy)methyl)phenylsulfonyl)nicotinic acid

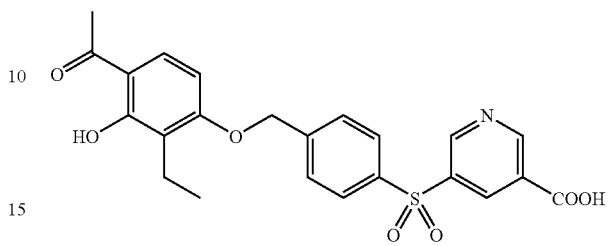

Using the method of Example 96 using 5-(4-((4-acetyl-2-ethyl-3-hydroxyphenoxy)methyl)phenylthio)nicotinic acid (140 mg, 0.33 mmol) affords the title compound (72 mg, 48%): $^1$H NMR (d$_6$-DMSO) δ 1.05 (t, J=7.4 Hz, 3H), 2.56 (s, 3H), 2.63 (q, J=7.4 Hz, 2H), 5.39 (s, 2H), 6.67 (d, J=9.4 Hz, 1H), 7.71 (d, J=8.2 Hz, 2H), 7.79 (d, J=9.0 Hz, 1H), 8.15 (d, J=8.2 Hz, 2H), 8.64 (dd, J=2.0, 2.3 Hz, 1H), 9.28 (d, J=2.0 Hz, 1H), 9.38 (d, J=2.3 Hz, 1H), 12.84 (s, 1H), 14.01 (s, 1H); MS (APCI-neg mode) m/z (rel intensity): 454 (M–H, 100%).

EXAMPLE 102

Synthesis of 5-(3-((4-acetyl-3-hydroxy-2-methylphenoxy)methyl)phenylsulfonyl) picolinic acid

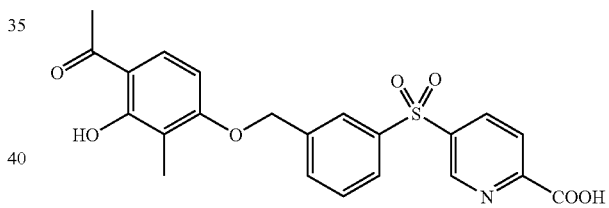

Using the method of Example 96 using 5-(3-((4-acetyl-3-hydroxy-2-methylphenoxy)methyl)phenylthio)picolinic acid (250 mg, 0.61 mmol) affords the title compound (57 mg, 21%): $^1$H NMR (d$_6$-DMSO) δ 2.04 (s, 3H), 2.58 (s, 3H), 5.38 (s, 2H), 6.70 (d, J=9.0 Hz, 1H), 7.72 (t, J=7.8 Hz, 1H), 7.82 (q, J=13.5 Hz, 2H), 8.04 (d, J=8.2 Hz, 1H), 8.15 (s, 1H), 8.21 (d, J=8.2 Hz, 1H), 8.51 (m, 1H), 9.24 (s, 1H), 12.85 (s, 1H); MS (APCI-neg mode) m/z (rel intensity): 440 (M–H, 100%).

EXAMPLE 103

Synthesis of 5-(3-((4-acetyl-2-ethyl-3-hydroxyphenoxy)methyl)phenylsulfonyl)picolinic acid

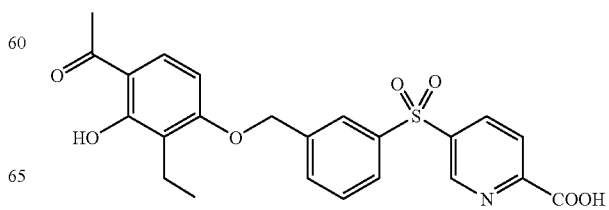

Using the method of Example 96 using 5-(3-((4-acetyl-2-ethyl-3-hydroxyphenoxy)methyl)phenylthio)picolinic acid (250 mg, 0.59 mmol) affords the title compound (160 mg, 59%): $^1$H NMR (d$_6$-DMSO) δ 1.03 (t, J=7.4 Hz, 3H), 2.57 (s, 3H), 2.60 (q, J=10.2 Hz, 2H), 5.38 (s, 2H), 6.69 (d, J=9.0 Hz, 1H), 7.83-7.70 (m, 3H), 8.04 (d, J=7.8 Hz, 1H), 8.13 (s, 1H), 8.20 (d, J=8.2 Hz, 1H), 8.50 (m, 1H), 9.21 (d, J=2.3 Hz, 1H), 12.84 (s, 1H); MS (APCI-neg mode) m/z (rel intensity): 454 (M−H, 100%).

EXAMPLE 104

Synthesis of 5-(3-((4-acetyl-3-hydroxy-2-propylphenoxy)methyl)phenylsulfonyl) picolinic acid

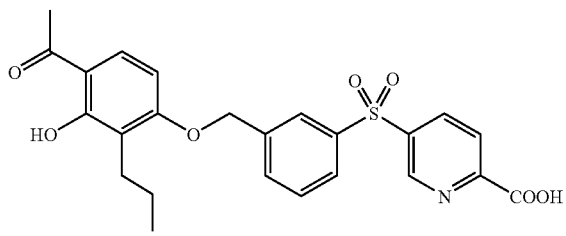

Using the method of Example 96 using 5-(3-((4-acetyl-3-hydroxy-2-propylphenoxy)methyl)phenylthio)picolinic acid (250 mg, 0.57 mmol) affords the title compound (170 mg, 63%): $^1$H NMR (d$_6$-DMSO) δ 0.86 (t, J=7.2 Hz, 3H), 1.47 (m, 2H), 2.58 (s, 3H), 2.58 (t, J=11.9 Hz, 2H), 5.37 (s, 2H), 6.70 (d, J=9.0 Hz, 1H), 7.72 (t, J=7.8 Hz, 1H), 7.80 (d, J=9.0 Hz, 2H), 8.04 (d, J=7.8 Hz, 1H), 8.13 (s, 1H), 8.20 (m, 1H), 8.50 (q, J=7.0 Hz, 1H), 9.21 (m, 1H), 12.85 (s, 2H); MS (APCI-neg mode) m/z (rel intensity): 468 (M−H, 100%).

EXAMPLE 105

Synthesis of 6-(3-((4-acetyl-3-hydroxy-2-methylphenoxy)methyl)phenylsulfonyl) isonicotinic acid

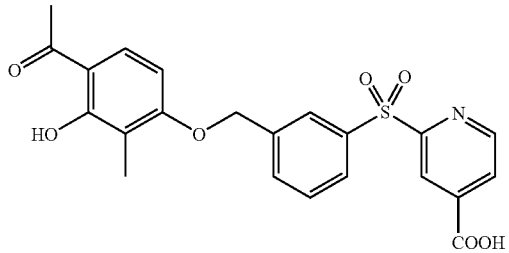

Using the method of Example 96 using 6-(3-((4-acetyl-3-hydroxy-2-methylphenoxy)methyl)phenylthio)isonicotinic acid (100 mg, 0.244 mmol) affords the title compound (23.0 mg, 24%): $^1$H NMR (d$_6$-DMSO) δ 2.03 (s, 3H), 2.58 (s, 3H), 5.38 (s, 2H), 6.69 (d, J=9.0 Hz, 1H), 7.70 (t, J=7.6 Hz, 1H), 7.80 (d, J=9.0 Hz, 1H), 7.83 (d, J=7.8 Hz, 1H), 7.98 (d, J=7.8 Hz, 1H), 8.07 (s, 1H), 8.08 (s, 1H), 8.49 (s, 1H), 8.89 (d, J=4.7 Hz, 1H), 12.85 (s, 1H); MS (APCI-neg mode) m/z (rel intensity): 440 (M−H, 100%).

EXAMPLE 106

Synthesis of 6-(3-((4-acetyl-3-hydroxy-2-propylphenoxy)methyl)phenylsulfonyl) isonicotinic acid

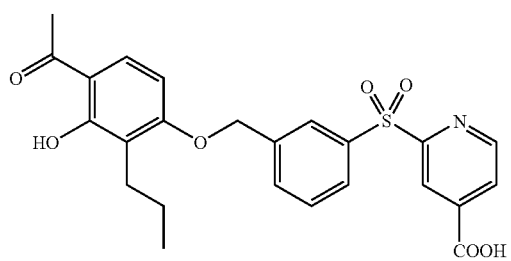

Using the method of Example 96 using 6-(3-((4-acetyl-3-hydroxy-2-propylphenoxy)methyl)phenylthio)isonicotinic acid (200 mg, 0.457 mmol) affords the title compound (87 mg, 41%): $^1$H NMR (d$_6$-DMSO) δ 0.86 (t, J=7.4 Hz, 3H), 1.51-1.42 (2, 1H), 2.58 (m, 2H), 2.58 (s, 3H), 5.37 (s, 1H), 6.69 (d, J=9.0 Hz, 1H), 7.71 (t, J=7.6 Hz, 1H), 7.80 (d, J=9.0 Hz, 2H), 7.99 (d, J=7.8 Hz, 1H), 8.07 (s, 1H), 8.08 (s, 1H), 8.49 (s, 1H), 8.88 (d, J=4.7 Hz, 1H), 12.84 (s, 1H); MS (APCI-neg mode) m/z (rel intensity): 469 ?? (M−H, 100%).

EXAMPLE 107

Synthesis of 6-(3-((4-acetyl-2-ethyl-3-hydroxyphenoxy)methyl)phenylsulfonyl) isonicotinic acid

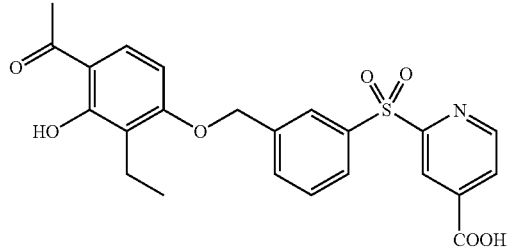

Using the method of Example 96 using 6-(3-((4-acetyl-2-ethyl-3-hydroxyphenoxy)methyl)phenylthio)isonicotinic acid (200 mg, 0.472 mmol) affords the title compound (125 mg, 58%): $^1$H NMR (d$_6$-DMSO) δ 1.02 (t, J=7.4 Hz, 3H), 2.57 (s, 3H), 2.60 (q, J=7.4 Hz, 2H), 5.38 (s, 2H), 6.68 (d, J=9.0 Hz, 1H), 7.71 (t, J=7.6 Hz, 1H), 7.80 (m, 2H), 7.99 (d, J=7.8 Hz, 1H), 8.07 (d, J=6.2 Hz, 2H), 8.49 (s, 1H), 8.88 (d, J=4.7 Hz, 1H), 12.83 (s, 1H); MS (APCI-neg mode) m/z (rel intensity): 454 (M−H, 100%).

EXAMPLE 108

Synthesis of 6-(4-((4-acetyl-3-hydroxy-2-methylphenoxy)methyl)phenylsulfonyl) isonicotinic acid

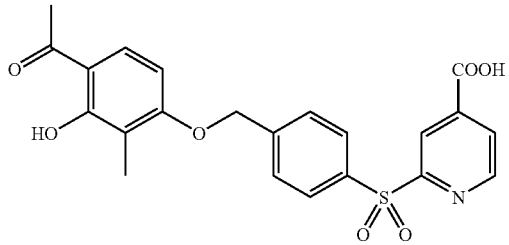

Using the method of Example 96 using 6-(4-((4-acetyl-3-hydroxy-2-methylphenoxy)methyl)phenylthio)isonicotinic acid (200 mg, 0.488 mmol) affords the title compound (163 mg, 76%): $^1$H NMR (d$_6$-DMSO) δ 2.07 (s, 3H), 2.57 (s, 3H), 5.39 (s, 2H), 6.69 (d, J=9.0 Hz, 1H), 7.66 (d, J=8.5 Hz, 2H), 7.80 (d, J=9.0 Hz, 1H), 8.05 (d, J=8.6 Hz, 2H), 8.09 (m, 1H), 8.49 (s, 1H), 8.90 (d, J=4.7 Hz, 1H), 12.84 (s, 1H); MS (APCI-neg mode) m/z (rel intensity): 440 (M–H, 100%).

EXAMPLE 109

Synthesis of 6-(4-((4-acetyl-2-ethyl-3-hydroxyphenoxy)methyl)phenylsulfonyl) isonicotinic acid

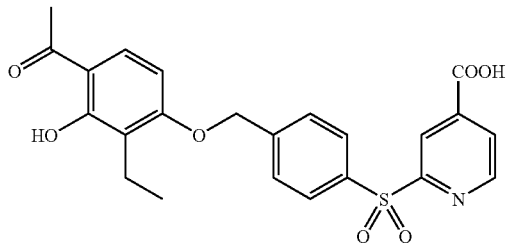

Using the method of Example 96 using 6-(4-((4-acetyl-2-ethyl-3-hydroxyphenoxy)methyl)phenylthio)isonicotinic acid (150 mg, 0.354 mmol) affords the title compound (20 mg, 12%): $^1$H NMR (d$_6$-DMSO) δ 1.05 (t, J=7.6 Hz, 3H), 2.57 (s, 3H), 2.64 (q, J=9.8 Hz, 2H), 5.39 (s, 2H), 6.68 (d, J=9.4 Hz, 1H), 7.70 (s, 1H), 7.72 (s, 1H), 7.80 (d, J=9.0 Hz, 2H), 8.04 (m, 3H), 8.86 (d, J=4.7 Hz, 1H), 12.84 (s, 1H); MS (APCI-neg mode) m/z (rel intensity): 454 (M–H, 100%).

EXAMPLE 110

Synthesis of 6-(4-((4-acetyl-3-hydroxy-2-propylphenoxy)methyl)phenylsulfonyl) isonicotinic acid

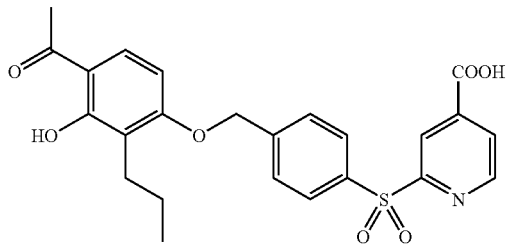

Using the method of Example 96 using 6-(4-((4-acetyl-3-hydroxy-2-propylphenoxy)methyl)phenylthio)isonicotinic acid (100 mg, 0.229 mmol) affords the title compound (2 mg, 2%): $^1$H NMR (d$_6$-DMSO) δ 0.88 (t, J=7.2 Hz, 3H), 1.49 (m, 2H), 2.57 (s, 3H), 2.61 (t, J=7.4 Hz, 2H), 5.38 (s, 2H), 6.68 (d, J=9.0 Hz, 1H), 7.69 (d, J=8.6 Hz, 2H), 7.80 (d, J=9.0 Hz, 1H), 7.99 (d, J=4.7 Hz, 1H), 8.03 (d, J=8.2 Hz, 2H), 8.46 (s, 1H), 8.78 (d, J=4.7 Hz, 1H), 12.84 (s, 1H); MS (APCI-neg mode) m/z (rel intensity): 468 (M–H, 100%).

We claim:
1. A compound of formula I

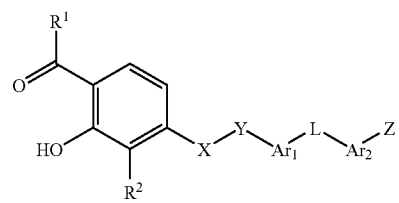

wherein
- $R^1$ is selected from the group consisting of C1-C5 alkyl, C3-C7 cycloalkyl, C4-C8 cycloalkylalkyl, phenyl and substituted phenyl;
- $R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazloyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl, and substituted pyridazinyl;
- X is selected from the group consisting of O, $S(O)_m$, and $NR^3$;
- Y is selected from the group consisting of C1-C3 alkanediyl and substituted C1-C3 alkanediyl;
- $Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;
- L is selected from the group consisting of -G-O-J-, -G-S(O)p-J-, and -G-N($R^4$)-J-;
- G is a bond;
- J is independently selected from the group consisting of a bond and C1-C3 alkanediyl;
- $R^3$ is independently hydrogen or C1-C5 alkyl;
- $R^4$ is independently selected from the group consisting of hydrogen, C1-C5 alkyl, C(=O)$R^3$, C(=O)NR$^3$R$^3$ and $SO_2R^3$;
- Z is selected from the group consisting of $(CH_2)_n$COOH,

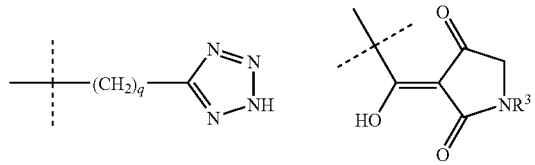

-continued

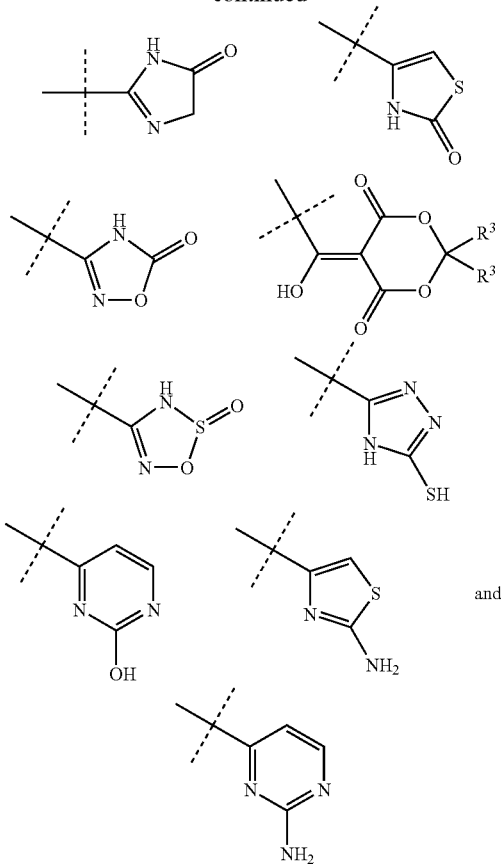

m and p are independently 0, 1, or 2;
n and q are independently 0, 1, 2 or 3; and
pharmaceutically acceptable salts thereof.

2. A compound according to claim 1 wherein X is O.
3. A compound according to claim 2 wherein Y is C1-C3 alkanediyl.
4. A compound according to claim 3 wherein $Ar_1$ and $Ar_2$ are independently phenylene or pyridinediyl.
5. A compound according to claim 4 wherein $R^2$ is selected from the group consisting of C1-C5 alkyl, halo and C1-C3 fluoroalkyl.
6. A compound according to claim 5 wherein L is O.
7. A compound according to claim 5 wherein L is S.
8. A compound according to claim 1 wherein
X is O;
Y is C1-C3 alkanediyl;
$Ar_1$ and $Ar_2$ are independently phenylene or pyridinediyl;
$R^2$ is selected from the group consisting of C1-C5 alkyl, halo and C1-C3 fluoroalkyl;
L is S;
Z is selected from the group consisting of $(CH_2)_n COOH$ and

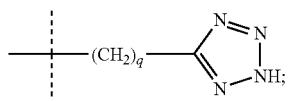

and n and q are 0.

9. A compound according to claim 8 wherein $Ar_1$ is phenylene.
10. A compound according to claim 9 wherein $Ar_2$ is pyridinediyl.
11. A compound according to claim 10 wherein $Ar_2$ is attached at the 1-4 position.
12. A compound according to claim 10 wherein $Ar_2$ is attached at the 1-3 position.
13. A compound according to claim 12 wherein $Ar_1$ is attached at the 1-3 position or 1-4 position.
14. A compound according to claim 8 wherein $R^1$ is methyl.
15. A compound according to claim 1 wherein
$R^1$ is methyl or ethyl;
$R^2$ is selected from the group consisting of hydrogen, methyl, ethyl, propyl, fluoro, chloro, trifluoromethyl, and COOH;
X is O;
Y is methylene;
$Ar_1$ is phenylene or pyridinediyl;
$Ar_2$ is selected from the group consisting of phenylene, trifluoromethylphenylene, and pyridinediyl;
L is selected from the group consisting of O, S, SO, $SO_2$ and NH; and
Z is COOH or

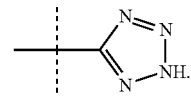

16. A compound according to claim 1 selected from the group consisting of 1-(2-hydroxy-3-methyl-4-{4-[4-(1H-tetrazol-5 -yl)-pyridin-2-yloxy]-benzyloxy}-phenyl)-ethanone, 1-(2-hydroxy-3-methyl-4-{4-[3-(1H-tetrazol-5-yl)-phenoxy]-benzyloxy}-phenyl)-ethanone and 1-(2-hydroxy-4-{3-[4-(2H-tetrazol-5-yl)-pyridin-2-yloxy]-benzyloxy}-3 -trifluoromethyl-phenyl)-ethanone.
17. A compound according to claim 1 which is 6-(3-((4-acetyl-3-hydroxy-2-propylphenoxy)methyl)phenylthio) isonicotinic acid.
18. A pharmaceutical composition comprising a compound of claim 1 and a pharmaceutically acceptable carrier, diluent or excipient.
19. A method of treating migraine, comprising administering to a patient in need thereof an effective amount of a compound of claim 1.
20. A process for preparing the compound of formula I

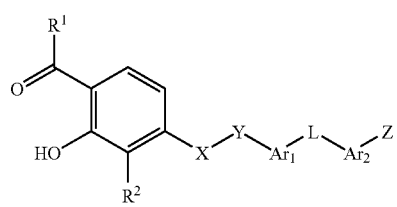

or a pharmaceutically acceptable salt thereof,
wherein
$R^1$ is selected from the group consisting of C1-C5 alkyl, C3-C7 cycloalkyl, C4-C8 cycloalkylalkyl, phenyl and substituted phenyl;

$R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazloyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl, and substituted pyridazinyl;

X is selected from the group consisting of O, $S(O)_m$, and NR3;

Y is selected from the group consisting of C1-C3 alkanediyl and substituted C1-C3 alkanediyl;

$Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;

L is selected from the group consisting of -G-O-J-, -G-S(O)p-J-, and -G-N($R^4$)-J-;

G is a bond;

J is independently selected from the group consisting of a bond and C1-C3 alkanediyl;

$R^3$ is independently hydrogen or C1-C5 alkyl;

$R^4$ is independently selected from the group consisting of hydrogen, C1-C5 alkyl, C(=O)$R^3$, C(=O)$NR^3R^3$ and $SO_2R^3$;

Z is selected from the group consisting of $(CH_2)_n$COOH,

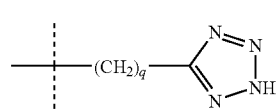
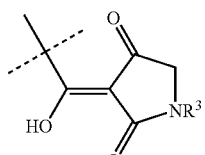
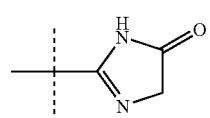
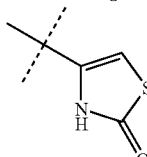
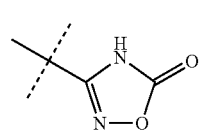
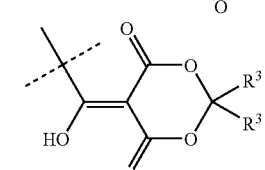
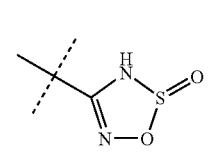
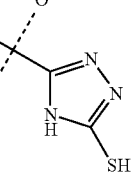
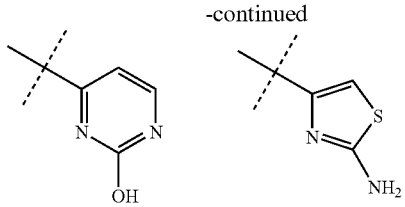
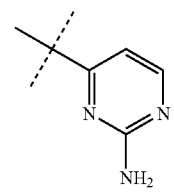

m and p are independently 0, 1, or 2;

n and q are independently 0, 1, 2 or 3;

comprising the step selected from (A) for a compound of formula I where Z is tetrazolyl,

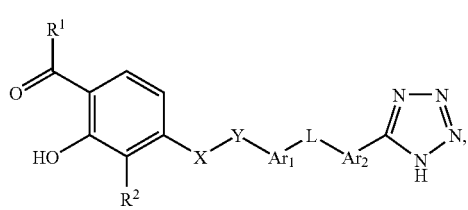

Z is tetrazolyl cycloaddition of a compound of formula II where $R^{10}$ is cyano with an azide reagent;

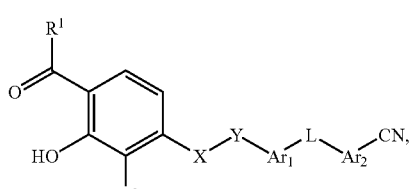

$R^{10}$ is cyano (B) for a compound of formula I where Z is COOH,

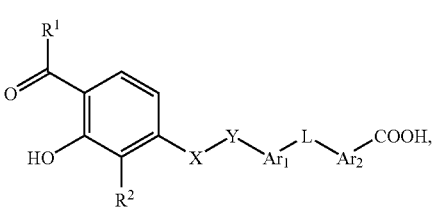

Z is COOH hydrolysis of a compound of formula II wherein $R^{10}$ is $COOR^{14}$ and $R^{14}$ is selected from the group consisting of C1-C5 alkyl, phenyl and benzyl;

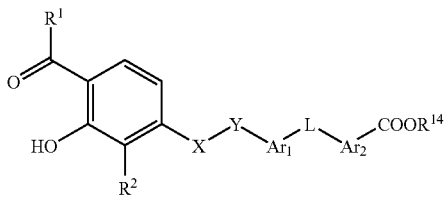

(C) for a compound of formula I where Z is COOH,

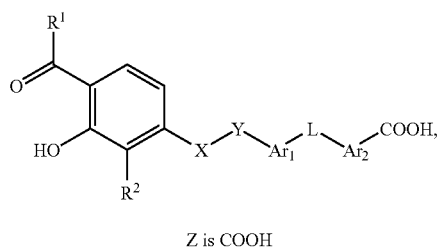

Z is COOH hydrolysis of a compound of formula II where $R^{10}$ is cyano; and

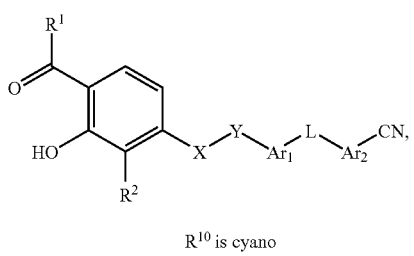

$R^{10}$ is cyano whereafter, when a pharmaceutically acceptable salt of the compound of formula I is required, it is obtained by reacting the acid of formula I with a physiologically acceptable base or by reacting a basic compound of formula I with a physiologically acceptable acid or by any other conventional procedure.

21. A compound of formula II

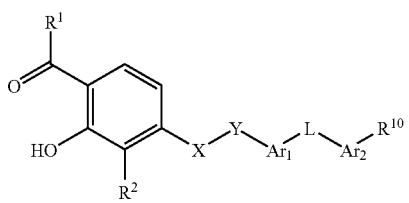

wherein $R^1$ is selected from the group consisting of C1-C5 alkyl, C3-C7 cycloalkyl, C4-C8 cycloalkylalkyl, phenyl and substituted phenyl;

$R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazloyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl, and substituted pyridazinyl;

X is selected from the group consisting of O, $S(O)_m$, and $NR^3$;

Y is selected from the group consisting of C1-C3 alkanediyl and substituted C1-C3 alkanediyl;

$Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;

L is selected from the group consisting of -G-O-J-, -G-S(O)p-J-, and -G-N($R^4$)-J-;

G is a bond;

J is independently selected from the group consisting of a bond and C1-C3 alkanediyl;

$R^3$ is independently hydrogen or C1-C5 alkyl;

$R^4$ is independently selected from the group consisting of hydrogen, C1-C5 alkyl, C(=O)$R^3$, C(=O)NR$^3$R$^3$ and SO$_2$R$^3$;

m and p are independently 0, 1, or 2;

n and q are independently 0, 1, 2 or 3; and $R^{10}$ is CN or $COOR^{14}$ in which $R^{14}$ is selected from the group consisting of C1-C5 alkyl, phenyl and benzyl;

other than 5-[[6-[(4-acetyl-3-hydroxy-2-propylphenoxy)methyl]-2-pyridinyl]-methoxy]-2-butoxybenzoic acid ethyl ester and 5-{3-[4-acetyl-3-hydroxy-propylphenoxy) methyl]phenoxyl}pyridine-2-carbonitrile.

22. A compound according to claim 21 wherein $R^{14}$ is methyl.

23. A compound according to claim 21 wherein $R^{14}$ is C1-C5 alkyl.

* * * * *